United States Patent
Hornberger et al.

(10) Patent No.: US 9,150,553 B2
(45) Date of Patent: Oct. 6, 2015

(54) CARBOXAMIDE COMPOUNDS AND THEIR USE AS CALPAIN INHIBITORS

(75) Inventors: Wilfried Hornberger, Ludwigshafen (DE); Helmut Mack, Ludwigshafen (DE); Andreas Kling, Ludwigshafen (DE); Achim Moeller, Ludwigshafen (DE); Barbara Vogg, Ludwigshafen (DE); Jürgen Delzer, Ludwigshafen (DE); Gisela Backfisch, Ludwigshafen (DE); Armin Beyerbach, Ludwigshafen (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 470 days.

(21) Appl. No.: 12/810,795

(22) PCT Filed: Dec. 29, 2008

(86) PCT No.: PCT/EP2008/068313
§ 371 (c)(1),
(2), (4) Date: Nov. 23, 2010

(87) PCT Pub. No.: WO2009/083581
PCT Pub. Date: Jul. 9, 2009

(65) Prior Publication Data
US 2011/0059968 A1    Mar. 10, 2011

(30) Foreign Application Priority Data

Dec. 28, 2007 (WO) .................. PCT/EP2007/064617
Jun. 25, 2008 (EP) ..................... 08159041

(51) Int. Cl.
*C07D 405/14* (2006.01)
*A61K 31/4439* (2006.01)
*C07D 491/052* (2006.01)

(52) U.S. Cl.
CPC .......... *C07D 405/14* (2013.01); *C07D 491/052* (2013.01)

(58) Field of Classification Search
CPC .......................... C07D 405/14; A61K 31/4439
USPC ........................................ 546/275.4; 514/341
See application file for complete search history.

(56) References Cited

FOREIGN PATENT DOCUMENTS

| WO | 98/16512 | 4/1998 |
| WO | 98/25883 | 6/1998 |

(Continued)

OTHER PUBLICATIONS

Saez, M.E., et al., "Drug Discovery Today," 2006, 11 (19/20), pp. 917-923.

(Continued)

*Primary Examiner* — Patricia L Morris
(74) *Attorney, Agent, or Firm* — Lisa V. Mueller; Michael Best & Friedrich LLP

(57) ABSTRACT

The present invention relates to novel carboxamide compounds of the formula I and their use for the manufacture of a medicament. The carboxamide compounds are prodrugs of inhibitors of calpain (calcium dependant cysteine proteases). The invention therefore also relates to the use of these carboxamide compounds for treating a disorder associated with an elevated calpain activity.

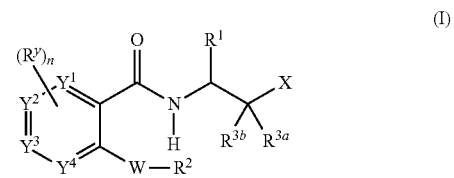

(I)

$R^1$ is $C_1$-$C_{10}$-alkyl, $C_2$-$C_{10}$-alkenyl, $C_2$-$C_{10}$-alkynyl, $C_3$-$C_7$-cycloalkyl, $C_3$-$C_7$-cycloalkyl-$C_1$-$C_4$-alkyl, aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, $R^2$ is $C_3$-$C_7$-cycloalkyl, $C_3$-$C_7$-cycloalkyl-$C_1$-$C_4$-alkyl, aryl, O-aryl, O—$CH_2$-aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, $R^{3a}$ and $R^{3b}$ together form a moiety S-Alk-S, O-Alk-S or O-Alk-O, wherein Alk is linear $C_2$-$C_5$-alkandiyl, which may be unsubstituted or substituted with 1, 2, 3 or 4 radicals selected from $C_1$-$C_4$-alkyl or halogen;

X is a radical of the formulae $C(=O)$—O—$R^{x1}$, $C(=O)$—$NR^{x2}R^{x3}$, $C(=O)$—$N(R^{x4})$—($C_1$-$C_6$-alkylene)-$NR^{x2}R^{x3}$, $C(=O)$—$N(R^{x4})NR^{x2}R^{x3}$, n is 0, 1 or 2, one of the variables $Y^1$, $Y^2$, $Y^3$ or $Y^4$ is a nitrogen atom, and the remaining variables $Y^1$, $Y^2$, $Y^3$ or $Y^4$ are CH;

$R^y$ is e.g. OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio etc.

W is a radical of the formulae W1 or W2 which is linked via nitrogen:

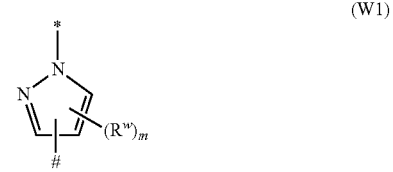

(W1)

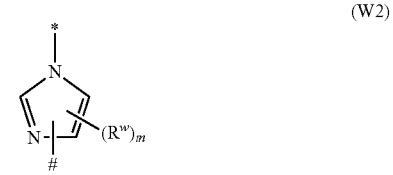

(W2)

in which * means the linkage to the 6-membered heteroaromatic ring, and # means the linkage to $R^2$, m is 0, 1 or 2, and $R^w$ is e.g. OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$.

11 Claims, No Drawings

(56) References Cited

FOREIGN PATENT DOCUMENTS

| | | |
|---|---|---|
| WO | 98/25899 | 6/1998 |
| WO | 99/17775 | 4/1999 |
| WO | 99/54293 | 10/1999 |
| WO | 99/54294 | 10/1999 |
| WO | 99/54304 | 10/1999 |
| WO | 99/54305 | 10/1999 |
| WO | 99/54310 | 10/1999 |
| WO | 99/54320 | 10/1999 |
| WO | 99/61423 | 12/1999 |
| WO | 03/080182 | 10/2003 |
| WO | 2008/080969 | 7/2008 |

OTHER PUBLICATIONS

Suzuki, K., et al., Biol. Chem. Hoppe-Seyler, 1995, 376 (9), pp. 523-529.
Barrett, M.J., et al., Life Sci. 1991, 48, pp. 1659-1669.
Wang, K., et al. Trends in Pharmacol. Sci. 1994, 15, pp. 412-419.
Hong, Seung-Chyul, et al. Stroke 1994, 25(3), pp. 663-669.
Bartus, R.T., et al., Neurological res. 1995, 17, pp. 249-258.
Saatman, K.E., et al., Proc. Natl. Acad. Sci. USA, 1996, 93, pp. 3428-3433.
Edelstein, C.L., et al., Proc. Natl. Acad. Sci. USA, 1995, 92, pp. 7662-7666.
Yoshida, Ken Ischi, et al., Jap. Cir. J. 1995, 59(1), pp. 40-48.
Patrick, G., et al., Nature 1999, 402, pp. 615-622.
Monaco, E.A., et al., Curr. Alzheimer Res. 2004, 1(1), pp. 33-38.
Higuchi, et al., J. Biol. Chem. 2005, 280(15), pp. 15229-15237.
Mokhtarian, F., et al., J. Neuroimmunology 2006, vol. 180, pp. 135-146.
Park, et al., J. Neurosci. 2005, 25, pp. 5365-5375.
Higaki, J., et al., Neuron, 1995, 14, pp. 651-659.
Watanabe, N., et al., Cytokine 1994, 6(6), pp. 597-601.
Shiba, E., et al., 20th Meeting Int. Ass. Breast Cancer Res., Sendai JP, Sep. 25-28, 1994, Into. J. Oncol. S(Suppl.), 1994, 381.
O'Donnell, et al., J. Neurosci. 2006, 26(3), pp. 981-990.
Teranishi, et al., Biochem. Biophys. Res. Comm. 2003, 303(3), pp. 940-946.
Kunz, et al., Pain 2004, 110, pp. 409-418.
Wang, et al., Brain 2004, 127, pp. 671-679.
Cuzzocrea, et al., American Journal of Pathology 2000, 157(6), pp. 2065-2079.
Carrogher, N.O., Curr. Pharm. Design 2006, 12, pp. 615-638.
Wang, K.K., et al., Drugs of the future 1998, 23(7), pp. 741-749.
Fehrentz, J.A., et al., Synthesis 1983, pp. 676-789.
Neffe, A.T., et al., "Developments in the design and synthesis of calpain inhibitors," current opinion in drug discovery and development, Current Drugs, London, GB, vol. 8, No. 6, Oct. 1, 2005 (pp. 684-700).

CARBOXAMIDE COMPOUNDS AND THEIR USE AS CALPAIN INHIBITORS

CROSS-REFERENCE TO RELATED APPLICATIONS

This is the U.S. national stage entry of International Patent Application No. PCT/EP2008/068313, filed on Dec. 29, 2008, which claims priority to European Patent Application No. 08159041.6, filed on Jun. 25, 2008, and International Patent Application No. PCT/EP2007/064617, filed on Dec. 28, 2007, the contents of all of which are hereby incorporated by reference.

The present invention relates to novel carboxamide compounds and their use for the manufacture of a medicament. The carboxamide compounds are prodrugs of inhibitors of calpain (calcium dependant cysteine proteases). The invention therefore also relates to the use of these carboxamide compounds for treating a disorder associated with an elevated calpain activity.

Calpains are intracellular, proteolytic enzymes from the cysteine protease group and are found in many cells. The enzyme calpain is activated by elevated calcium concentration, with a distinction being made between calpain I or μ-calpain, which is activated by μ-molar concentrations of calcium ions, and calpain II or m-calpain, which is activated by μ-molar concentrations of calcium ions. Currently, further calpain isoenzymes are also postulated (M. E. Saez et al.; Drug Discovery Today 2006, 11 (19/20), pp. 917-923; K. Suzuki et al., Biol. Chem. Hoppe-Seyler, 1995, 376 (9), pp. 523-9).

Calpains play an important role in various physiological processes. These processes include the cleavage of different regulatory proteins such as protein kinase C, cytoskeletal proteins such as MAP 2 and spectrin, and muscle proteins, protein degradation in rheumatoid arthritis, proteins in the activation of platelets, neuropeptide metabolism, proteins in mitosis, and others which are listed in: M. J. Barrett et al., Life Sci. 1991, 48, pp. 1659-69; K. Wang et al., Trends in Pharmacol. Sci. 1994, 15, pp. 412-419.

Elevated calpain levels have been measured in various pathophysiological processes, for example: ischemias of the heart (e.g. myocardial infarction), the kidney or the central nervous system (e.g. stroke), inflammations, muscular dystrophies, cataracts of the eyes, diabetes, HIV disorders, injuries to the central nervous system (e.g. brain trauma), Alzheimer's, Huntington's, Parkinson's diseases, multiple sclerosis etc. (see K. K. Wang, above). It is assumed that there is a connection between these diseases and generally or persistently elevated intracellular calcium levels. This results in calcium-dependent processes becoming hyperactivated and no longer being subject to normal physiological control. A corresponding hyperactivation of calpains can also trigger pathophysiological processes.

For this reason, it was postulated that inhibitors of calpain could be of use for treating these diseases. This postulate was confirmed by a variety of investigations. Thus, Seung-Chyul Hong et al., Stroke 1994, 25 (3), pp. 663-669, and R. T. Bartus et al., Neurological Res. 1995, 17, pp. 249-258, have demonstrated that calpain inhibitors have a neuroprotective effect in acute neurodegenerative impairments or ischemias such as occur after cerebral stroke. K. E. Saatman et al., Proc. Natl. Acad. Sci. USA, 1996, 93, pp. 3428-3433 describe that following experimental brain traumas, calpain inhibitors also improved recovery from the memory performance deficits and neuromotor impairments. C. L. Edelstein et al., Proc. Natl. Acad. Sci. USA, 1995, 92, pp. 7662-6, found that calpain inhibitors have a protective effect on hypoxia-damaged kidneys. Yoshida, Ken Ischi et al., Jap. Circ. J. 1995, 59 (1), pp. 40-48, pointed out that calpain inhibitors had favorable effects following cardiac damage which was produced by ischemia or reperfusion.

It has been shown in recent years that both the function and the metabolism of a number of important proteins involved in the development of Alzheimer's disease are modulated by calpain. Various external influences such as, for example, excitotoxins, oxidative stress or else the action of amyloid protein lead to hyperactivation of calpain in the nerve cell, causing, as cascade, a dysregulation of the CNS-specific kinase cdk5 and subsequently a hyperphosphorylation of the so-called tau protein. Whereas the actual task of the tau protein consists of stabilizing the microtubules and thus the cytoskeleton, phosphorylated tau is no longer able to fulfil this function; the cytoskeleton collapses, axonal transport of matter is impaired and thus eventually the nerve cell degenerates (G. Patrick et al., Nature 1999, 402, pp. 615-622; E. A. Monaco et al.; Curr. Alzheimer Res. 2004, 1 (1), pp. 33-38). Accumulation of phosphorylated tau additionally leads to the formation of so-called neurofibrillary tangles (NFTs) which, together with the well-known amyloid plaques, represent an important feature of Alzheimer's disease. Similar changes in the tau protein, generally referred to as tauopathies are also observed in other (neuro) degenerative disorders such as, for example, following stroke, inflammations of the brain, Parkinsonism, in normal-pressure hydrocephalus and Creutzfeldt-Jakob disease.

It has been possible to demonstrate the involvement of calpain in neurodegenerative processes in transgenic mice with the aid of appropriate inhibitors (Higuchi et al.; J. Biol. Chem. 2005, 280 (15), pp. 15229-15237). It was possible with the aid of a calpain inhibitor to reduce markedly the clinical signs of acute autoimmune encephalomyelitis in a mouse model of multiple sclerosis (F. Mokhtarian et al.; J. Neuroimmunology 2006, Vol. 180, pp. 135-146). It has further been shown that calpain inhibitors on the one hand block the Aβ-induced degeneration of neurons (Park et al.; J. Neurosci. 2005, 25, pp. 5365-5375), and in addition reduce the release of the β-amyloid precursor protein (β APP) (J. Higaki et al., Neuron, 1995, 14, pp. 651-659). With this background, calpain inhibitors having sufficient CNS availability represent a novel therapeutic principle for the treatment of neurodegenerative disorders in general and in particular also of Alzheimer's disease.

The release of interleukin-1α is likewise inhibited by calpain inhibitors (N. Watanabe et al., Cytokine 1994, 6(6), pp. 597-601). It has additionally been found that calpain inhibitors show cytotoxic effects on tumor cells (E. Shiba et al. 20th Meeting Int. Ass. Breast Cancer Res., Sendai Jp, 1994, 25.-28.Sep., Int. J. Oncol. S(Suppl.), 1994, 381).

The involvement of calpain in HIV disorders has only recently been shown. Thus, it has been demonstrated that the HIV-induced neurotoxicity is mediated by calpain (O'Donnell et al.; J. Neurosci. 2006, 26 (3), pp. 981-990). Calpain involvement in the replication of the HIV virus has also been shown (Teranishi et al.; Biochem. Biophys. Res. Comm. 2003, 303 (3), pp. 940-946).

Recent investigations indicate that calpain plays a part in so-called nociception, the perception of pain. Calpain inhibitors showed a distinctly beneficial effect in various preclinically relevant models of pain, e.g. in the thermally induced hyperalgesia in rats (Kunz et al.; Pain 2004, 110, pp. 409-418), in Taxol-induced neuropathy (Wang et al.; Brain 2004, 127, pp. 671-679) and in acute and chronic inflammatory processes (Cuzzocrea et al.; American Journal of Pathololgy 2000, 157 (6), pp. 2065-2079).

Further possible applications of calpain inhibitors are detailed in: M. E. Saez et al.; Drug Discovery Today 2006, 11 (19/20), pp. 917-923; N. O. Carragher, Curr. Pharm. Design 2006, 12, pp. 615-638; K. K. Wang et al.; Drugs of the Future 1998, 23 (7), pp. 741-749; and Trends in Pharmacol. Sci., 1994, 15, pp. 412-419.

With the calpain inhibitors described to date a general distinction is made between irreversible and reversible inhibitors, and peptide and non-peptide inhibitors.

Irreversible inhibitors are usually alkylating substances. They have the disadvantage that they firstly react unselectively and/or are unstable in the body. Thus, corresponding inhibitors often show unwanted side effects such as toxicity, and application thereof is therefore markedly restricted. The irreversible inhibitors include for example epoxides such as E64, α-halo ketones, and disulfides.

A large number of known reversible calpain inhibitors are peptide aldehydes which are derived in particular from di- or tripeptides such as, for example, Z-Val-Phe-H (MDL 28170). Derivatives and prodrugs structurally derived from aldehydes are also described, especially corresponding acetals and hemiacetals (e.g. hydroxytetrahydrofurans, hydroxyoxazolindines, hydroxymorpholines and the like), but also imines or hydrazones. However, under physiological conditions, peptide aldehydes and related compounds usually have the disadvantage that, owing to their reactivity, they are frequently unstable, are rapidly metabolized and are prone to unspecific reactions which may likewise cause toxic effects (J. A. Fehrentz and B. Castro, *Synthesis* 1983, pp. 676-78).

In recent years, a number of non-peptide carboxamides having a β-keto function in the amine moiety and inhibiting calpain have been described. Thus, WO-98/16512 describes 3-amino-2-oxo carboxylic acid derivatives whose amino group is amidated with a 4-piperidinecarboxylic acid compound. WO-99/17775 describes similar compounds which are amidated with a quinolinecarboxylic acid. WO-98/25883, WO-98/25899 and WO-99/54294 describe 3-amino-2-oxo carboxylic acid derivatives whose amino group is amidated with a substituted benzoic acid. WO-99/61423 describes 3-amino-2-oxo carboxylic acid derivatives whose amino group is amidated with an aromatic carboxylic acid carrying a tetrahydroquinoline/isoquinoline and 2,3-dihydroindole/isoindole residue. Similar compounds in which the aromatic carboxylic acid residue carries a heterocyloalkyl radical or (hetero)aryl radical which is optionally connected via a linker are described in WO-99/54320, WO-99/54310, WO-99/54304 and WO-99/54305. WO-99/54293 describes benzamides of 4-amino-3-oxo carboxylic acid derivatives. WO-03/080182 describes the use of the aforementioned amides for the treatment of pulmonary diseases. The nonpeptide calpain inhibitors mentioned therein also have a number of disadvantages, in particular a low or absent selectivity in respect of related cysteine proteases, such as various cathepsins, likewise possibly leading to unwanted side effects.

The present invention is thus based on the object of providing compounds which in vivo inhibit, in particular selectively, calpain even at low serum concentrations. The compounds were intended in particular to display in vivo a high selectivity in relation to the inhibition of calpain, i.e. inhibit other cystein proteases, e.g. cathepsin, not at all or only at higher concentrations.

It has now been found that carboxamide compounds of the general formula I described below, the pharmaceutically suitable salts, and the tautomers thereof are converted in vivo into the compounds of the formula II. The compounds of the formula II, their salts and their hydrates have been described as selective calpain inhibitors in PCT/EP2007/064617 (published as WO2008/080969), to which full reference is made.

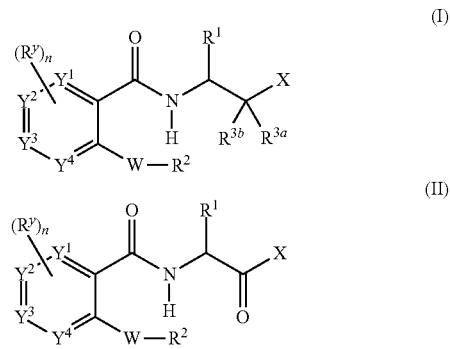

In formula I, and likewise in formula II (where applicable) the variables have the following meanings:

$R^1$ is hydrogen, $C_1$-$C_{10}$-alkyl, $C_2$-$C_{10}$-alkenyl, $C_2$-$C_{10}$-alkynyl, where the last 3 radicals mentioned may be partly or completely halogenated and/or have 1, 2 or 3 substituents $R^{1a}$, $C_3$-$C_7$-cycloalkyl, $C_3$-$C_7$-cycloalkyl-$C_1$-$C_4$-alkyl, where a $CH_2$ group in the cycloalkyl moiety of the last two radicals mentioned may be replaced by O, NH, or S, or two adjacent C atoms may form a double bond, where the cycloalkyl moiety may further have 1, 2, 3 or 4 radicals $R^{1b}$, aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, where aryl and hetaryl in the last 6 radicals mentioned may be unsubstituted or carry 1, 2, 3 or 4 identical or different radicals $R^{1c}$; where $R^{1a}$ is selected independently of one another from OH, SH, COOH, CN, $OCH_2COOH$, $C_1$-$C_6$-alkoxy, $C_1$-$C_6$-halolkoxy, $C_3$-$C_7$-cycloalkyloxy, $C_1$-$C_6$-alkylthio, $C_1$-$C_6$-haloalkylthio, $COOR^{a1}$, $CONR^{a2}R^{a3}$, $SO_2NR^{a2}R^{a3}$, $NR^{a2}$—$SO_2$—$R^{a4}$, $NR^{a2}$—CO—$R^{a5}$, $SO_2$—$R^{a4}$, $NR^{a6}R^{a7}$, $R^{1b}$ is selected independently of one another from OH, SH, COOH, CN, $OCH_2COOH$, halogen, phenyl which optionally has 1, 2 or 3 substituents $R^{1d}$, or $C_1$-$C_6$-alkyl, $C_1$-$C_6$-alkoxy, $C_1$-$C_6$-alkylthio, where the alkyl moieties in the last 3 substituents mentioned may be partly or completely halogenated and/or have 1, 2 or 3 substituents $R^{1a}$, $COOR^{b1}$, $CONR^{b2}R^{b3}$, $SO_2NR^{b2}R^{b3}$, $NR^{b2}$—$SO_2$—$R^{b4}$, $NR^{b2}$—CO—$R^{b5}$, $SO_2$—$R^{b4}$, $NR^{b6}R^{b7}$, in addition two $R^{1b}$ radicals may together form a $C_1$-$C_4$-alkylene group, or 2 $R^{1b}$ radicals bonded to adjacent C atoms of cycloalkyl may form together with the carbon atoms to which they are bonded also a benzene ring, $R^{1c}$ is selected independently of one another from OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the alkyl moieties in the last 4 substituents mentioned may be partly or completely halogenated and/or have 1, 2 or 3 substituents $R^{1a}$, $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 $R^{1b}$ radicals, and where 1 or 2 $CH_2$-groups in the cycloalkyl moiety may be replaced by O, NH or S, aryl, hetaryl, O-aryl, O—CH$_2$-aryl, where the last three radicals mentioned are unsubstituted in the aryl moiety or may carry 1, 2, 3 or 4 R$^{1d}$ radicals, COOR$^{c1}$, CONR$^{c2}$R$^{c3}$, SO$_2$NR$^{c2}$R$^{c3}$, NR$^{c2}$—SO$_2$—R$^{c4}$, NR$^{c2}$—CO—R$^{c5}$, SO$_2$—R$^{c4}$,
—(CH$_2$)$_p$—NR$^{c6}$R$^{c7}$ with p=0, 1, 2, 3, 4, 5 or 6 and O—(CH$_2$)$_q$—NR$^{c6}$R$^{c7}$ with q=2, 3, 4, 5 or 6; where R$^{a1}$, R$^{b1}$ and R$^{c1}$ are independently of one another H, C$_1$-C$_6$-alkyl, C$_1$-C$_6$-haloalkyl, C$_1$-C$_6$-alkyl which has 1, 2 or 3 substituents R$^{1a}$, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{1d}$, R$^{a2}$, R$^{b2}$ and R$^{c2}$ are independently of one another H, C$_1$-C$_6$-alkyl, C$_1$-C$_6$-haloalkyl, C$_1$-C$_6$-alkyl which has 1, 2 or 3 substituents R$^{1a}$, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{1d}$, and R$^{a3}$, R$^{b3}$ and R$^{c3}$ are independently of one another H, C$_1$-C$_6$-alkyl, C$_1$-C$_6$-haloalkyl, C$_1$-C$_6$-alkyl which has 1, 2 or 3 substituents R$^{1a}$, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{1d}$, or the two radicals R$^{a2}$ and R$^{a3}$, or R$^{b2}$ and R$^{b3}$ or R$^{c2}$ and R$^{c3}$ form together with the N atom a 3 to 7-membered, optionally substituted nitrogen heterocycle which may optionally have 1, 2 or 3 further different or identical heteroatoms from the group of O, N, S as ring members, R$^{a4}$, R$^{b4}$ and R$^{c4}$ are independently of one another C$_1$-C$_6$-alkyl, C$_1$-C$_6$-haloalkyl, C$_1$-C$_6$-alkyl which has 1, 2 or 3 substituents R$^{1a}$, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{1d}$, and R$^{a5}$, R$^{b5}$ and R$^{c5}$ have independently of one another one of the meanings mentioned for R$^{a1}$, R$^{b1}$ and R$^{c1}$;

R$^{a6}$, R$^{b6}$ and R$^{c6}$ are independently of one another H, C$_1$-C$_6$-alkyl, C$_1$-C$_6$-alkoxy, C$_1$-C$_6$-haloalkyl, C$_1$-C$_6$-alkyl which has 1, 2 or 3 substituents R$^{1a}$, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, CO—C$_1$-C$_6$-alkyl, CO—O—C$_1$-C$_6$-alkyl, SO$_2$—C$_1$-C$_6$-alkyl, aryl, hetaryl, O-aryl, OCH$_2$-aryl, aryl-C$_1$-C$_4$-alkyl, hetaryl-C$_1$-C$_4$-alkyl, CO-aryl, CO-hetaryl, CO-(aryl-C$_1$-C$_4$-alkyl), CO-(hetaryl-C$_1$-C$_4$-alkyl), CO—O-aryl, CO—O-hetaryl, CO—O-(aryl-C$_1$-C$_4$-alkyl), CO—O-(hetaryl-C$_1$-C$_4$-alkyl), SO$_2$-aryl, SO$_2$-hetaryl, SO$_2$-(aryl-C$_1$-C$_4$-alkyl) or SO$_2$-(hetaryl-C$_1$-C$_4$-alkyl), where aryl and hetaryl in the last 18 radicals mentioned are unsubstituted or have 1, 2 or 3 substituents R$^{1d}$, and R$^{a7}$, R$^{b7}$ and R$^{c7}$ are independently of one another H, C$_1$-C$_6$-alkyl, C$_1$-C$_6$-haloalkyl, C$_1$-C$_6$-alkyl which has 1, 2 or 3 substituents R$^{1a}$, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{1d}$, or the two radicals R$^{a6}$ and R$^{a7}$, or R$^{b6}$ and R$^{b7}$ or R$^{c6}$ and R$^{c7}$ form together with the N atom a 3 to 7-membered, optionally substituted nitrogen heterocycle which may optionally have 1, 2 or 3 further different or identical heteroatoms from the group of O, N and S as ring members, or two radicals R$^{1b}$ or R$^{1c}$ bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms from the group of O, N and S as ring members;

R$^{1d}$ is selected from halogen, OH, SH, NO$_2$, COOH, C(O)NH$_2$, CHO, CN, NH$_2$, OCH$_2$COOH, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, CO—C$_1$-C$_6$-alkyl, CO—O—C$_1$-C$_6$-alkyl, NH—C$_1$-C$_6$-alkyl, NHCHO, NH—C(O)C$_1$-C$_6$-alkyl, and SO$_2$—C$_1$-C$_6$-alkyl;

R$^2$ is C$_3$-C$_7$-cycloalkyl, C$_3$-C$_7$-cycloalkyl-C$_1$-C$_4$-alkyl, where a CH$_2$ group in the cycloalkyl moiety of the last two radicals mentioned may be replaced by O, NH, or S, or two adjacent C atoms may form a double bond, where the cycloalkyl moiety may additionally have 1, 2, 3 or 4 R$^{2a}$ radicals;

aryl, O-aryl, O—CH$_2$-aryl, hetaryl, aryl-C$_1$-C$_6$-alkyl, aryl-C$_2$-C$_6$-alkenyl, hetaryl-C$_1$-C$_4$-alkyl or hetaryl-C$_2$-C$_6$-alkenyl, where aryl and hetaryl in the last 8 radicals mentioned may be unsubstituted or carry 1, 2, 3 or 4 identical or different R$^{2b}$ radicals; where R$^{2a}$ has one of the meanings indicated for R$^{1b}$ and R$^{2b}$ has one of the meanings indicated for R$^{1c}$, R$^{1a}$ and R$^{3b}$ together form a moiety S-Alk-S, O-Alk-S or O-Alk-O, wherein Alk is linear C$_2$-C$_5$-alkandiyl, which may be unsubstituted or substituted with 1, 2, 3 or 4 radicals selected from C$_1$-C$_4$-alkyl or halogen;

X is a radical of the formulae C(=O)—O—R$^{x1}$, C(=O)—NR$^{x2}$R$^{x3}$, C(=O)—N(R$^{x4}$)—(C$_1$-C$_6$-alkylene)-NR$^{x2}$R$^{x3}$ or C(=O)—N(R$^{x4}$)NR$^{x2}$R$^{x3}$, in which R$^{x1}$ is hydrogen, C$_1$-C$_6$-alkyl, C$_1$-C$_6$-haloalkyl, C$_1$-C$_6$-alkyl which has 1, 2 or 3 substituents R$^{xa}$, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, where alkyl, alkenyl, alkoxy, alkynyl, cycloalkyl, heterocycloalkyl in the last 6 radicals mentioned are unsubstituted or have 1, 2 or 3 substituents R$^{xa}$, or aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{xd}$, R$^{x2}$ is H, OH, CN, C$_1$-C$_6$-alkyl, C$_1$-C$_6$-haloalkyl, C$_1$-C$_6$-alkyl which has 1, 2 or 3 substituents R$^{xa}$, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$- alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, O—$C_1$-$C_6$-alkyl, where alkyl, alkoxy, alkenyl, alkynyl, cycloalkyl, heterocycloalkyl in the last 10 radicals mentioned are unsubstituted or have 1, 2 or 3 substituents $R^{xa}$, aryl, O-aryl, O—$CH_2$-aryl, hetaryl, O—$CH_2$-hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$-(hetaryl-$C_1$-$C_4$-alkyl), where aryl and hetaryl in the last 19 radicals mentioned are unsubstituted or have 1, 2 or 3 substituents $R^{xd}$, and $R^{x3}$ is H, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, where alkyl, alkenyl, alkoxy, alkynyl, cycloalkyl, heterocycloalkyl in the last 6 radicals mentioned are unsubstituted or have 1, 2 or 3 substituents $R^{xa}$, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{xd}$, or the two radicals $R^{x2}$ and $R^{x3}$ form together with the N atom a 3 to 7-membered nitrogen heterocycle which may optionally have 1, 2 or 3 further different or identical heteroatoms from the group of O, N, S as ring members, and which may have 1, 2 or 3 substituents $R^{xb}$, $R^{x4}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, where alkyl, alkenyl, alkoxy, alkynyl, cycloalkyl, heterocycloalkyl in the last 9 radicals mentioned are unsubstituted or have 1, 2 or 3 substituents $R^{xa}$, aryl, O-aryl, O—$CH_2$-aryl, hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$-(hetaryl-$C_1$-$C_4$-alkyl), where aryl and hetaryl in the last 18 radicals mentioned are unsubstituted or have 1, 2 or 3 substituents $R^{xd}$, and where $R^{xa}$ has one of the meanings indicated for $R^{1a}$, $R^{xb}$ has one of the meanings indicated for $R^{1b}$, and $R^{xd}$ has one of the meanings indicated for $R^{1d}$;

n is 0, 1 or 2, one of the variables $Y^1$, $Y^2$, $Y^3$ or $Y^4$ is a nitrogen atom, and the remaining variables $Y^1$, $Y^2$, $Y^3$ or $Y^4$ are CH;

$R^y$ is selected independently of one another from OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{ya}$, $C_3$-$C_7$-cycloalkyl, $C_3$-$C_7$-cycloalkyl-$C_1$-$C_4$-alkyl, $C_3$-$C_7$-cycloalkyl-O, where the cycloalkyl moiety in the last three radicals mentioned may have 1, 2, 3 or 4 $R^{yb}$ radicals, aryl, O-aryl, $CH_2$-aryl, O—$CH_2$-aryl, where the last 4 radicals mentioned are unsubstituted in the aryl moiety or may carry 1, 2, 3 or 4 radicals $R^{yd}$, $COOR^{y1}$, $CONR^{y2}R^{y3}$, $SO_2NR^{y2}R^{y3}$, —NH—$SO_2$—$R^{y4}$, NH—CO—$R^{y5}$, $SO_2$—$R^{y4}$, —$(CH_2)_p$—$NR^{y6}R^{y7}$ with p=0, 1, 2, 3, 4, 5 or 6 and O—$(CH_2)_q$—$NR^{y6}R^{y7}$ with q=2, 3, 4, 5 or 6;

or two $R^y$ radicals bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms from the group of O, N, S as ring members, where $R^{ya}$ has one of the meanings indicated for $R^{1a}$,
$R^{yb}$ has one of the meanings indicated for $R^{1b}$,
$R^{yd}$ has one of the meanings indicated for $R^{1d}$,
$R^{y1}$ has one of the meanings indicated for $R^{c1}$,
$R^{y2}$ has one of the meanings indicated for $R^{c2}$,
$R^{y3}$ has one of the meanings indicated for $R^{c3}$,
$R^{y4}$ has one of the meanings indicated for $R^{c4}$,
$R^{y5}$ has one of the meanings indicated for $R^{c5}$,
$R^{y6}$ has one of the meanings indicated for $R^{c6}$, and
$R^{y7}$ has one of the meanings indicated for $R^{c7}$;

W is a radical of the formulae W1 or W2 which is linked via nitrogen:

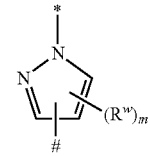

(W1)

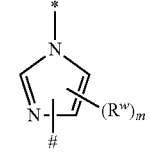

(W2)

in which
* means the linkage to the 6-membered heteroaromatic ring, and # means the linkage to $R^2$,
m is 0, 1 or 2, and
$R^w$ is selected from OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{wa}$, $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 radicals $R^{wb}$, and where 1 or 2 $CH_2$-groups in the cycloalkyl moiety may be replaced by O, NH or S, aryl, hetaryl, O-aryl, O—$CH_2$-aryl, hetaryl, where the last four radicals mentioned are unsubstituted in the aryl moiety or may carry 1, 2, 3 or 4 radicals $R^{wd}$, $COOR^{w1}$, $CONR^{w2}R^{w3}$, $SO_2NR^{w2}R^{w3}$, $NR^{w2}$—$SO_2$—$R^{w4}$, $NR^{w2}$—CO—$R^{w5}$, $SO_2$—$R^{w4}$, —$(CH_2)_p$—$NR^{w6}R^{w7}$ with p=0, 1, 2, 3, 4, 5 or 6 and O—$(CH_2)_q$—$NR^{w6}R^{w7}$ with q=2, 3, 4, 5 or 6;

or two $R^w$ radicals bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms from the group of O, N, S as ring members, where $R^{wa}$ has one of the meanings indicated for $R^{1a}$,
$R^{wb}$ has one of the meanings indicated for $R^{1b}$,
$R^{wd}$ has one of the meanings indicated for $R^{1d}$,
$R^{w1}$ has one of the meanings indicated for $R^{c1}$,
$R^{w2}$ has one of the meanings indicated for $R^{c2}$,
$R^{w3}$ has one of the meanings indicated for $R^{c3}$,
$R^{w4}$ has one of the meanings indicated for $R^{c4}$,
$R^{w5}$ has one of the meanings indicated for $R^{c5}$,
$R^{w6}$ has one of the meanings indicated for $R^{c6}$,
$R^{w7}$ has one of the meanings indicated for $R^{c7}$, or W forms together with $R^2$ a bi- or tricyclic radical of the formulae W3, W4, W5, W6, W7 or W8 which is linked via nitrogen:

(W3)
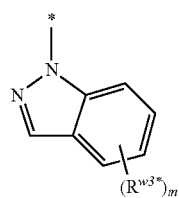

(W4)
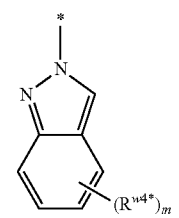

(W5)
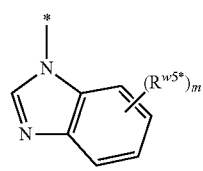

(W6)
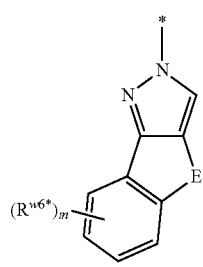

(W7)
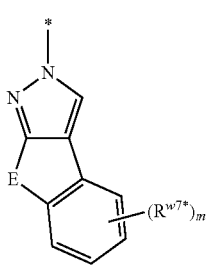

(W8)
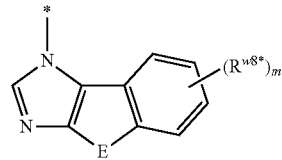

in which
* means the linkage to the 6-membered heteroaromatic ring,
m is 0, 1 or 2, and
$R^{w3*}, R^{w4*}, R^{w5*}, R^{w6*}, R^{w7*}$ and $R^{w8*}$ have independently of one another one of the meanings indicated for $R^w$, E has one of the following meanings: —$CR_E^2R_E^3$—, —$CHR_E^2$—$CHR_E^3$, $CH_2$—$CH_2$—$CH_2$—, —CO—, —CO—$NR_E^1$—, —$NR_E^1$—CO—, —O—, —$CH_2$—O—, —O—$CH_2$—, —S—, —S—$CH_2$—, —$CH_2$—S—, —SO—, $CH_2$—SO—, —SO—$CH_2$—, —$SO_2$—, —$CH_2$—$SO_2$—, —$SO_2$—$CH_2$—, —$NR_E^1$—, —$NR_E^1$—$CH_2$—, —$CH_2$—$NR_E^1$—, —$SO_2$—$NR_E^1$—, —$NR_E^1$—$SO_2$—, —CO—O—, —O—CO—, —(=$CR_E^2R_E^3$)—, —$CR_E^2$=$CR_E^3$—, where $R_E^1$ is H, $C_1$-$C_6$-alkyl, $C_1$-$C_6$-haloalkyl, $C_1$-$C_6$-alkyl which has 1, 2 or 3 substituents $R_E^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, aryl, hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O—aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$-(hetaryl-$C_1$-$C_4$-alkyl), where aryl and hetaryl in the last 16 radicals mentioned are unsubstituted or have 1, 2 or 3 substituents $R_E^{1d}$, and $R_E^2$, $R_E^3$ are independently of one another selected from hydrogen, $C_1$-$C_6$-alkyl, $C_1$-$C_6$-alkoxy, $C_2$-$C_6$-alkenyl, $C_2$-$C_6$-alkynyl, where the last 4 radicals mentioned may be partly or completely halogenated and/or have 1, 2 or 3 substituents $R_E^{1a}$, $C_3$-$C_7$-cycloalkyl, $C_3$-$C_7$-cycloalkyl-O, where a $CH_2$ group in the cycloalkyl moiety of the last three radicals mentioned may be replaced by O, NH, or S, or two adjacent C atoms may form a double bond, where the cycloalkyl moiety may further have 1, 2, 3 or 4 $R_E^{1b}$ radicals, aryl, hetaryl, aryl-$C_1$-$C_6$-alkyl, or hetaryl-$C_1$-$C_4$-alkyl, where aryl and hetaryl in the last 4 radicals mentioned may be unsubstituted or carry 1, 2, 3 or 4 identical or different radicals $R_E^{1d}$; and where $R_E^{1a}$ has one of the meanings indicated for $R^{1a}$, $R_E^{1b}$ has one of the meanings indicated for $R^{1b}$, and $R_E^{1d}$ has one of the meanings indicated for $R^{1d}$.

The present invention therefore relates to the carboxamide compounds of the general formula I, their tautomers and the pharmaceutically suitable salts of the carboxamide compounds I and of the tautomers of I.

The carboxamide compounds of the invention of the formula I, their salts and their tautomers are metabolized in vivo into the compounds of the formula II and thus are prodrugs of the compounds II. The serum levels of the compounds of formula II thereby achieved are comparable or only slightly lower than the serum levels which are achieved by directly administering the compounds of the formula II, a tautomer or a pharmaceutically suitable salt of II.

The compounds of the formula II effectively inhibit calpain even at low concentrations. They are additionally distinguished by a high selectivity in relation to the inhibition of the calpain compared with other cysteine proteases such as cathepsin B, cathepsin K, cathepsin L and cathepsin S.

The carboxamide compounds of the invention of the formula I, their salts and their tautomers are therefore particularly suitable for treating disorders and conditions in creatures, especially human creatures, which are associated with an elevated calpain activity.

The invention therefore also relates to the use of carboxamide compounds of the formula I, their tautomers and their pharmaceutically suitable salts for the manufacture of a medicament, in particular of a medicament which is suitable for the treatment of a disorder or a condition which is associated with an elevated calpain activity.

The invention further relates to a medicament, in particular a medicament which is suitable for the treatment of a disorder or a condition which is associated with an elevated calpain activity. The medicament comprises at least one carboxamide compound of the formula I, as described herein, a tautomer or a pharmaceutically suitable salt of the compound I or of the tautomer of I.

Under physiological conditions, the carboxamide compounds of the formula II may be in the form of β-keto compounds as depicted in formula II or in the form of its hydrate as depicted in the formula II-H.

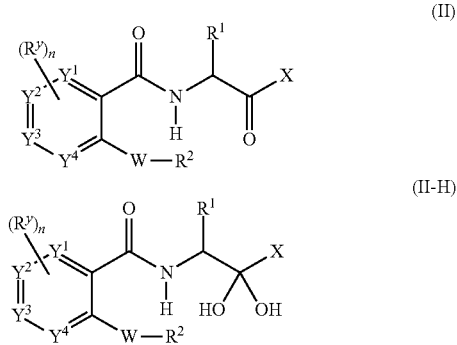

In the presence of water, especially under physiological conditions, usually both the β-keto form II and the hydrate form II may be present in a mixture.

It is equally possible to use pharmaceutically suitable salts of the carboxamide compounds of the formula I or of their tautomers, especially acid addition salts with physiologically tolerated organic or inorganic acids. Examples of suitable physiologically tolerated organic and inorganic acids are hydrochloric acid, hydrobromic acid, phosphoric acid, nitric acid, sulfuric acid, organic sulfonic acids having 1 to 12 carbon atoms, e.g. $C_1$-$C_4$-alkylsulfonic acids such as methanesulfonic acid, cycloaliphatic sulfonic acids such as S-(+)-10-camphorsulfonic acids, and aromatic sulfonic acids such as benzenesulfonic acid and toluenesulfonic acid, di- and tricarboxylic acids and hydroxy carboxylic acids having 2 to 10 carbon atoms, such as oxalic acid, malonic acid, maleic acid, fumaric acid, mucic acid, lactic acid, tartaric acid, citric acid, glycolic acid and adipic acid, as well as cis- and trans-cinnamic acid, furan-2-carboxylic acid and benzoic acid. Further suitable acids are described in Fortschritte der Arzneimittelforschung, Volume 10, pages 224 et seq., Birkhäuser Verlag, Basel and Stuttgart, 1966. The physiologically tolerated salts of the compounds of the formula I may be in the form of mono-, di-, tri- or tetrasalts, meaning that they may comprise 1, 2, 3 or 4 of the aforementioned acid molecules per molecule of the formula I. The acid molecules may be present in their acidic form or as anion.

The compounds of the invention may be in the form of a mixture of diastereomers, or of a mixture of diastereomers in which one of the two diastereomers is enriched, or of essentially diastereomerically pure compounds (diastereomeric excess de >90%). The compounds are preferably in the form of essentially diastereomerically pure compounds (diastereomeric excess de >90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee >90%). However, the compounds of the invention are frequently prone to racemization in relation to the stereochemistry of the carbon atom which carries the radical $R^1$, so that mixtures are frequently obtained in relation to this carbon atom, or compounds which exhibit a uniform stereochemistry in relation to this C atom form mixtures under physiological conditions. However, in relation to other stereocenters and the occurrence, associatied therewith, of enantiomers and diastereomers, it is preferred to employ the compounds enantiomerically pure or diastereomerically pure.

In the context of the present description, unless stated otherwise, the terms "alkyl", "alkoxy", "alkylthio", "haloalkyl", "haloalkoxy", "haloalkylthio", "alkenyl", "alkynyl", "alkylene" and radicals derived therefrom always include both unbranched and branched "alkyl", "alkoxy", "alkylthio", "haloalkyl", "haloalkoxy", "haloalkylthio", "alkenyl", "alkynyl" and "alkylene", respectively.

The prefix $C_n$-$C_m$- indicates the respective number of carbons in the hydrocarbon unit. Unless indicated otherwise, halogenated substituents preferably have one to five identical or different halogen atoms, especially fluorine atoms or chlorine atoms. $C_0$-Alkylene or $(CH_2)_0$ or similar expressions in the context of the description designate, unless indicated otherwise, a single bond.

The term "halogen" designates in each case, fluorine, bromine, chlorine or iodine, specifically fluorine, chlorine or bromine.

Examples of other meanings are:

Alkyl, and the alkyl moieties for example in alkoxy, alkylthio, arylalkyl, hetarylalkyl, cycloalkylalkyl or alkoxyalkyl: saturated, straight-chain or branched hydrocarbon radicals having one or more C atoms, e.g. 1 to 4, 1 to 6 or 1 to 10 carbon atoms, e.g. $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. In one embodiment of the invention, alkyl stands for small alkyl groups such as $C_1$-$C_4$-alkyl. In another embodiment of the invention, alkyl stands for larger alkyl groups such as $C_5$-$C_{10}$-alkyl.

Haloalkyl: an alkyl radical having ordinarily 1 to 6 or 1 to 4 C atoms as mentioned above, whose hydrogen atoms are partly or completely replaced by halogen atoms such as fluorine, chlorine, bromine and/or iodine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl.

Cycloalkyl, and the cycloalkyl moieties for example in cycloalkoxy or cycloalkyl-$C_1$-$C_6$-alkyl: monocyclic, saturated hydrocarbon groups having three or more C atoms, e.g. 3 to 7 carbon ring members, such as cyclopropyl, cyclobutyl, cyclopentyl, cyclohexyl.

Alkenyl, and alkenyl moieties for example in aryl-($C_2$-$C_6$)-alkenyl: monounsaturated, straight-chain or branched hydrocarbon radicals having two or more C atoms, e.g. 2 to 4, 2 to 6 or 2 to 10 carbon atoms and one double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl.

Alkynyl: straight-chain or branched hydrocarbon groups having two or more C atoms, e.g. 2 to 4, 2 to 6 or 2 to 10 carbon atoms and one or two triple bonds in any position but nonadjacent, e.g. $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl.

Alkoxy or alkoxy moieties for example in alkoxyalkyl:
Alkyl as defined above having preferably 1 to 6 or 1 to 4 C atoms, which is linked via an O atom: e.g. methoxy, ethoxy, n-propoxy, 1-methylethoxy, butoxy, 1-methylpropoxy, 2-methylpropoxy or 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

Haloalkoxy: alkoxy as described above, in which the hydrogen atoms of these groups are partly or completely replaced by halogen atoms, i.e. for example $C_1$-$C_6$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, specifically chloromethoxy, fluoromethoxy, difluoromethoxy, trifluoromethoxy, 2-fluoroethoxy, 2-chloroethoxy or 2,2,2-trifluoroethoxy.

Alkoxyalkyl: an alkyl radical ordinarily having 1 to 4 C atoms, in which one hydrogen atom is replaced by an alkoxy radical ordinarily having 1 to 6 or 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)-butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkylthio: alkyl as defined above preferably having 1 to 6 or 1 to 4 C atoms, which is linked via an S atom, e.g. methylthio, ethylthio, n-propylthio and the like.

Haloalkylthio: haloalkyl as defined above preferably having 1 to 6 or 1 to 4 C atoms, which is linked via an S atom, e.g. fluoromethylthio, difluoromethylthio, trifluoromethylthio, 2-fluoroethylthio, 2,2-difluoroethylthio, 2,2,2-trifluoroethylthio, pentafluoroethylthio, 2-fluoropropylthio, 3-fluoropylthio, 2,2-difluoropropylthio, 2,3-difluoropropylthio, and heptafluoropropylthio.

Aryl: a mono-, bi- or tricyclic aromatic hydrocarbon radical such as phenyl or naphthyl, especially phenyl.

Heterocyclyl: a heterocyclic radical which may be saturated, partly unsaturated or aromatic and which ordinarily has 3, 4, 5, 6, 7 or 8 ring atoms, where ordinarily 1, 2, 3 or 4, in particular 1, 2 or 3, of the ring atoms are heteroatoms such as N, S or O, besides carbon atoms as ring members.

Examples of saturated heterocycles are in particular:

Heterocycloalkyl: i.e. a saturated heterocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:

C-bonded, 3-4-membered saturated rings such as 2-oxiranyl, 2-oxetanyl, 3-oxetanyl, 2-aziridinyl, 3-thiethanyl, 1-azetidinyl, 2-azetidinyl.

C-bonded, 5-membered saturated rings such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as:

tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as:

tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as:

piperidin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heterocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as:

2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as:

2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran- 2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as:
2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as:
1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Hetaryl: a 5- or 6-membered aromatic heterocyclic radical which ordinarily has 1, 2, 3 or 4 nitrogen atoms or a heteroatom selected from oxygen and sulfur and, if appropriate, 1, 2 or 3 nitrogen atoms as ring members besides carbon atoms as ring members: for example C-bonded, 5-membered heteroaromatic radicals having 1, 2, 3 or 4 nitrogen atoms or a heteroatom selected from oxygen and sulfur and, if appropriate, having 1, 2 or 3 nitrogen atoms as ring members, such as:
2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered heteroaromatic radicals having 1, 2, 3 or 4 nitrogen atoms as ring members, such as:
pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:
pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles which have one of the aforementioned 5- or 6-membered heterocyclic rings and a further saturated, unsaturated or aromatic carbocycle fused thereto, for example a benzene, cyclohexane, cyclohexene or cyclohexadiene ring, or a further 5- or 6-membered heterocyclic ring fused thereto, where the latter may likewise be saturated, unsaturated or aromatic. These include for example quinolinyl, isoquinolinyl, indolyl, indolizinyl, isoindolyl, indazolyl, benzofuryl, benzothienyl, benzo[b]thiazolyl, benzoxazolyl, benzthiazolyl and benzimidazolyl. Examples of 5- to 6-membered heterocyclic radicals comprising a fused benzene ring include dihydroindolyl, dihydroindolizynyl, dihydroisoindolyl, dihydroquinolinyl, dihydroisoquinolinyl, chromenyl and chromanyl.

Arylalkyl: an aryl radical as defined above which is linked via an alkylene group, in particular via a methylene, 1,1-ethylene or 1,2-ethylene group, e.g. benzyl, 1-phenylethyl and 2-phenylethyl.

Arylalkenyl: an aryl radical as defined above, which is linked via an alkenylene group, in particular via a 1,1-ethenyl, 1,2-ethenyl or 1,3-propenyl group, e.g. 2-phenylethen-1-yl and 1-phenylethen-1-yl.

Cycloalkoxy: a cycloalkyl radical as defined above which is linked via an oxygen atom, e.g. cyclopropyloxy, cyclobutyloxy, cyclopentyloxy or cyclohexyloxy.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl or cyclohexylmethyl.

Heterocyclylalkyl and hetarylalkyl: a heterocyclyl or hetaryl radical as defined above which is linked via an alkylene group, in particular via a methylene, 1,1-ethylene or 1,2-ethylene group.

The expression "optionally substituted" means in the context of the present invention that the respective moiety is substituted or has 1, 2 or 3, in particular 1, substituents which are selected from halogen, $C_1$-$C_4$-alkyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl and NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

A skilled person will readily understand that the sulfur or oxygen atoms, respectively, in the moieties S-Alk-S, O-Alk-S or O-Alk-O, which are formed by the radicals $R^{1a}$ and $R^{3b}$ in formula I, are connected with the carbon atom carrying the $R^{1a}$ and $R^{3b}$. In relation to their use as prodrugs of selective calpain inhibitors the moiety Alk in the moieties S-Alk-S, O-Alk-S or O-Alk-O is preferably selected from 1,2-ethandiyl and 1,3-propandiyl, which are unsubstituted or substituted by 1 or 2 $C_1$-$C_4$-alkyl groups. Particular preference is given to compounds of the formula I, wherein the radicals $R^{1a}$ and $R^{3b}$ together form a moiety of the formula O-Alk-O, wherein Alk is as defined above, in particular 1,2-ethandiyl or 1,3-propandiyl, which are unsubstituted or substituted by 1 or 2 $C_1$-$C_4$-alkyl groups. More preferably the radicals $R^{1a}$ and $R^{3b}$ together form a moiety of the formula O—$CH_2$—$CHR^3$—O, wherein $R^3$ is hydrogen or $C_1$-$C_4$-alkyl. Thus a preferred embodiment of the invention relates to compounds of the formula I', to the tautomers thereof and to the pharmaceutically suitable salts thereof

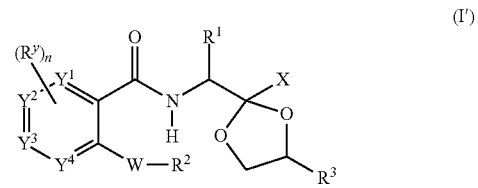

(I')

in which n, X, $Y^1$, $Y^2$, $Y^3$, $Y^4$, W, $R^1$, $R^2$ and $R^y$ have the aforementioned meanings and $R^3$ is hydrogen or $C_1$-$C_4$-alkyl.

As regards the variables $Y^1$, $Y^2$, $Y^3$, $Y^4$ a skilled person will readily recognize that for n=1 or 2, one or two of the moieties $Y^1$, $Y^2$, $Y^3$, $Y^4$ (depending on the number of n) are C—$R^y$ instead of C—H. Apart from that, a preferred embodiment of the invention relates to compounds of the formulae I and I' (and likewise to compounds of formula II) to the tautomers thereof and to the pharmaceutically suitable salts thereof, wherein $Y^4$ is nitrogen, while $Y^1$, $Y^2$, $Y^3$ are CH (or C—$R^y$, respectively, if n is 1 or 2). These compounds can be described by the following formulae I-a and I-a'

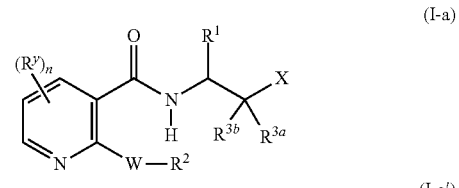

(I-a)

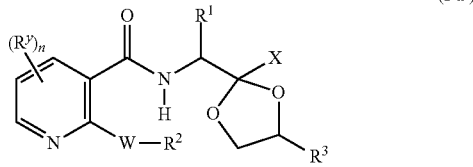

(I-a')

in which n, X, W, $R^1$, $R^2$, $R^{3a}$, $R^{3b}$, $R^y$ have the meaning given herein.

In relation to their use as prodrugs of selective calpain inhibitors the variables m, n, $R^1$, $R^2$, W, X in formulae I, I', I-a and I-a' (and likewise in formula II) preferably have the following meanings, where these represent, both considered on their own and in combination with one other, special embodiments of the compounds of the formulae I, I-a, I-a' and II:

m is 0 or 1, in particular 0;

n is 0 or 1, in particular 0;

$R^1$ $C_1$-$C_{10}$-alkyl, preferably $C_3$-$C_8$-alkyl, which may be partly or completely halogenated and/or have 1, 2 or 3 substituents $R^{1a}$, in particular unsubstituted $C_1$-$C_{10}$-alkyl, specifically unsubstituted $C_3$-$C_8$-alkyl, $C_3$-$C_7$-cycloalkyl-$C_1$-$C_4$-alkyl, specifically $C_3$-$C_7$-cycloalkylmethyl, 1-($C_3$-$C_7$-cycloalkyl)ethyl or 2-($C_3$-$C_7$-cycloalkyl)ethyl, where the cycloalkyl moiety may have 1, 2, 3 or 4 radicals $R^{1b}$, very specifically cyclohexylmethyl, phenyl-$C_1$-$C_4$-alkyl and hetaryl-$C_1$-$C_4$-alkyl, in particular benzyl, 1-phenylethyl, 2-phenylethyl, hetarylmethyl, 1-hetarylethyl, 2-hetarylethyl such as thienylmethyl, pyridinylmethyl, where phenyl and hetaryl in the last radicals mentioned may be unsubstituted or carry 1, 2, 3 or 4 identical or different radicals $R^{1c}$.

Preferred among these are those compounds of the general formulae I, I', I-a and I-a' in which $R^1$ is phenyl-$C_1$-$C_4$-alkyl, in particular benzyl, where phenyl may be unsubstituted or carry 1, 2, 3 or 4 identical or different radicals $R^{1c}$.

In this connection, $R^{1a}$, $R^{1b}$ and $R^{1c}$ where present have the aforementioned meanings. In particular:

$R^{1a}$ is $C_1$-$C_4$-alkoxy or $C_1$-$C_4$-haloalkoxy;

$R^{1b}$ is halogen, $C_1$-$C_4$-alkyl, $C_1$-$C_4$-haloalkyl, $C_1$-$C_4$-alkoxy or $C_1$-$C_4$-haloalkoxy; and $R^{1c}$ is halogen, $C_1$-$C_4$-alkyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2$NH—$C_1$-$C_6$-alkyl, CON—($C_1$-$C_6$-alkyl)$_2$, $SO_2$N—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2$NH-phenyl, CONH-hetaryl, $SO_2$NH-hetaryl, $SO_2$-phenyl, NH—$SO_2$-phenyl, NH—CO-phenyl, NH—$SO_2$-hetaryl, NH—CO-hetaryl where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy, —($CH_2$)$_p$—$NR^{c6}R^{c7}$ with p=0, 1, 2, 3, 4, 5 or 6, in particular 0, and —O—($CH_2$)$_q$—$NR^{c6}R^{c7}$ with q=2, 3, 4, 5 or 6, in particular 2, where $R^{c6}$, $R^{c7}$ are independently of one another hydrogen or $C_1$-$C_6$-alkyl, or together with the nitrogen atom to which they are bonded, are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy. $R^{1c}$ is in particular halogen, $C_1$-$C_4$-alkyl, $C_1$-$C_4$-haloalkyl, $C_1$-$C_4$-alkoxy or $C_1$-$C_4$-haloalkoxy.

$R^2$ aryl or hetaryl, where aryl and hetaryl in the last 2 radicals mentioned may be unsubstituted or carry 1, 2, 3 or 4 identical or different radicals $R^{2b}$, aryl-$C_1$-$C_6$-alkyl, aryl-$C_2$-$C_6$-alkenyl or hetaryl-$C_1$-$C_4$-alkyl, where aryl and hetaryl in the last 3 radicals mentioned may be unsubstituted or carry 1, 2, 3 or 4 identical or different radicals $R^{2b}$.

Preferred among these are those compounds of the general formulae I, I', I-a and I-a' in which $R^2$ is selected from aryl and hetaryl, specifically from phenyl, thienyl and pyridyl, where aryl and hetaryl (or phenyl, thienyl and pyridyl) may be unsubstituted or carry 1, 2, 3 or 4, in particular 1 or 2, identical or different radicals $R^{2b}$. Most preference is given to compounds of the general formulae I, I', I-a and I-a' in which $R^2$ is phenyl which is unsubstituted or carries 1, 2, 3 or 4, in particular 1 or 2, identical or different radicals $R^{2b}$.

In this connection, $R^{2a}$ and $R^{2b}$ where present have the aforementioned meanings. In particular:

$R^{2a}$ is halogen, $C_1$-$C_4$-alkyl, OH, CN, $CF_3$, O—$CF_3$, COOH, O—$CH_2$—COOH, $C_1$-$C_6$-alkoxy, $C_1$-$C_6$-alkylthio, COO—$C_1$-$C_6$-alkyl, $CONH_2$, CONH—$C_1$-$C_6$-alkyl, $SO_2$NH—$C_1$-$C_6$-alkyl, CONH-phenyl, $SO_2$NH-phenyl, CONH-hetaryl, $SO_2$NH-hetaryl, CON—($C_1$-$C_6$-alkyl)$_2$, $SO_2$N—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, $SO_2$-phenyl, NH—$SO_2$-phenyl, NH—CO-phenyl, NH—$SO_2$-hetaryl, NH—CO-hetaryl or $NR^{b6}R^{b7}$, where $R^{b6}$, $R^{b7}$ are independently of one another hydrogen or $C_1$-$C_6$-alkyl, or together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy; and $R^{2b}$ is halogen, $C_1$-$C_4$-alkyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2$NH—$C_1$-$C_6$-alkyl, CON—($C_1$-$C_6$-alkyl)$_2$, $SO_2$N—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2$NH-phenyl, CONH-hetaryl, $SO_2$NH-hetaryl, $SO_2$-phenyl, NH—$SO_2$-phenyl, NH—CO-phenyl, NH—$SO_2$-hetaryl, NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy, —($CH_2$)$_p$—$NR^{c6}R^{c7}$ with p=0, 1, 2, 3, 4, 5 or 6, in particular 0, and —O—($CH_2$)$_q$—$NR^{c6}R^{c7}$ with q=2, 3, 4, 5 or 6, in particular 2, where $R^{c6}$, $R^{c7}$ are independently of one another hydrogen or $C_1$-$C_6$-alkyl, or together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

X is a radical C(=O)—$NR^{x2}R^{x3}$ in which $R^{x2}$ and $R^{x3}$ have one of the aforementioned meanings. Compounds preferred among these are those in which:

$R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$. In particular, $R^{x2}$ is hydrogen, $C_1$-$C_6$-alkyl, $C_1$-$C_6$-haloalkyl, $C_1$-$C_6$-alkyl which has 1 or 2 substituents $R^{xa}$, $C_3$-$C_7$-cycloalkyl-$C_1$-$C_4$-alkyl, $C_3$-$C_7$-heterocycloalkyl-$C_1$-$C_4$-alkyl, aryl, hetaryl, aryl-$C_1$-$C_4$-alkyl or hetaryl-$C_1$-$C_4$-alkyl. $R^{x2}$ is very particularly preferably hydrogen.

$R^{x3}$ is H, $C_1$-$C_6$-alkyl, $C_1$-$C_6$-haloalkyl or $C_1$-$C_6$-alkyl which has 1, 2 or 3 substituents $R^{xa}$. In particular, $R^{x3}$ is hydrogen, $C_1$-$C_6$-alkyl, $C_1$-$C_6$-haloalkyl, $C_1$-$C_6$-alkyl which has 1 or 2 substituents $R^{xa}$. $R^{x3}$ is very particularly preferably hydrogen.

Compounds of the formulae I, I', I-a and I-a' which are likewise preferred are those in which the group $NR^{x2}R^{x3}$ is a nitrogen heterocycle of the following formulae:

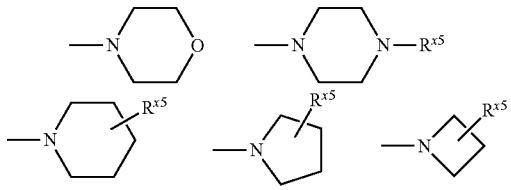

in which $R^{x5}$ is hydrogen or has the meaning indicated for $R^{xb}$. In particular, $R^{x5}$ is $C_1$-$C_6$-alkyl, $C_1$-$C_6$-haloalkyl, $C_1$-$C_6$-alkyl which has 1, 2 or 3 substituents $R^{xa}$, or $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl-$C_1$-$C_4$-alkyl or hetaryl-$C_1$-$C_4$-alkyl, where aryl and hetaryl in the last 2 radicals mentioned are unsubstituted or have 1, 2 or 3 substituents $R^{xd}$, or COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, CONH-phenyl, $SO_2NH$-phenyl, CONH-hetaryl, $SO_2NH$-hetaryl, where phenyl and hetaryl in the last 4 radicals mentioned are unsubstituted or may have 1, 2 or 3 substituents which are selected from the halogen, $C_1$-$C_4$-alkyl, $C_1$-$C_4$-haloalkyl, $C_1$-$C_4$-alkoxy and $C_1$-$C_4$-haloalkoxy. In particular, $R^{x5}$ is hydrogen or $C_1$-$C_4$-alkyl.

In a particularly preferred embodiment of the invention, X in formulae I, I', I-a and I-a' is $C(O)$—$NH_2$.

In another embodiment of the invention, X is $C(O)OR^{x1}$ in which $R^{x1}$ has the aforementioned meanings. In particular, $R^{x1}$ is $C_1$-$C_6$-alkyl, $C_1$-$C_6$-haloalkyl, $C_1$-$C_6$-alkyl which has 1, 2 or 3 substituents $R^{xa}$, or $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl stands, where aryl and hetaryl in the last 4 radicals mentioned are unsubstituted or have 1, 2 or 3 substituents $R^{xd}$.

In this connection, $R^{xa}$ has the aforementioned meanings and is in particular $C_1$-$C_4$-alkoxy or $C_1$-$C_4$-haloalkoxy. In this connection, $R^{xd}$ has the aforementioned meanings and is preferably F, Cl, OH, COOH, $C(O)NH_2$, CN, $NH_2$, $OCH_2COOH$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, CO—$C_1$-$C_4$-alkyl, CO—O—$C_1$-$C_4$-alkyl, NH—$C_1$-$C_4$-alkyl, NH—$C(O)C_1$-$C_4$-alkyl or $SO_2$—$C_1$-$C_4$-alkyl.

W a radical of the formulae W1 or W2 or the group W—$R^2$ is a radical of the formula W6.

In the formulae W1 and W2, $R^2$ is preferably bonded to the carbon in position 3 or 4, as shown in the following formulae W1a, W1b and W2a:

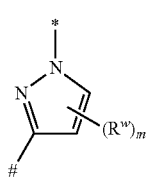

W1a

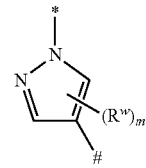

W1b

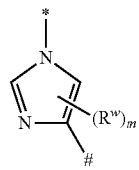

W2a

In the formulae W1a, W1b and W2a, the meanings of *, #, m and $R^w$ are those mentioned above. In particular, m is 0 or 1 and specifically 0. Where m is 1, $R^w$ is preferably selected from halogen, $C_1$-$C_6$-alkyl, $C_1$-$C_6$-alkyl which is substituted by 1, 2 or 3 substituents $R^{wa}$, or OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl, NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy. $R^w$ is in particular selected from OH, F, Cl, CN, $CF_3$, $C_1$-$C_6$-alkyl which is unsubstituted or may have 1, 2 or 3 substituents $R^{wa}$, or $C_1$-$C_6$-haloalkyl, $C_1$-$C_6$-alkoxy, $C_1$-$C_6$-haloalkoxy and $C_3$-$C_7$-cycloalkyl. In this connection, $R^{xa}$ has the aforementioned meanings and is in particular $C_1$-$C_4$-alkoxy or $C_1$-$C_4$-haloalkoxy. $R^w$ is particularly preferably selected from F, Cl, CN, $CF_3$, $CH_3$, $C_2H_5$ and $OCH_3$.

Where the group W—$R^2$ is a radical of the formula W6, m is preferably 0 or 1 and specifically 0. Where m is 1, $R^{w6*}$ is preferably selected from halogen, $C_1$-$C_6$-alkyl, $C_1$-$C_6$-alkyl which is substituted by 1, 2 or 3 substituents $R^{wa}$, or OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl, NH—CO-hetaryl where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy. $R^{w6*}$ is in particular selected from OH, F, Cl, CN, $CF_3$, $C_1$-$C_6$-alkyl which is unsubstituted or may have 1, 2 or 3 substituents $R^{wa}$, or $C_1$-$C_6$-haloalkyl, $C_1$-$C_6$-alkoxy, $C_1$-$C_6$-haloalkoxy and $C_3$-$C_7$-cycloalkyl. In this connection, $R^w$ has the aforementioned meanings and is in particular $C_1$-$C_4$-alkoxy or $C_1$-$C_4$-haloalkoxy. E in W6 preferably has one of the following meanings: $CH_2$, $CH_2CH_2$, CO, CO—NH, O, CH=CH, $CH_2O$, $OCH_2$, $SO_2$, $SO_2NR_E^1$ or $NR_E^1SO_2$, and is in particular $CH_2$, $CH_2CH_2$, O, CH=CH, $CH_2O$, $OCH_2$, $SO_2$, $SO_2NR_E^1$ or $NR_E^1SO_2$. In this connection, $R_E^1$ has one of the aforementioned meanings and is in particular hydrogen or $C_1$-$C_4$-alkyl.

Compounds of the formulae I, I', I-a and I-a' which are particularly preferred among the compounds of the invention of the general formulae I, I', I-a and I-a' are those in which W is a radical W1a, and particularly preferred among these are those in which m is 0 or 1 and specifically 0. More preference is given to compounds of the formulae I, I', I-a and I-a', wherein W is a radical W1, wherein $R^2$ is bound to the 3-position of the pyrazole ring. The compounds of this particular preferred embodiment can be described by the following formulae I-A, I-A', I-A.a and I-A.a'

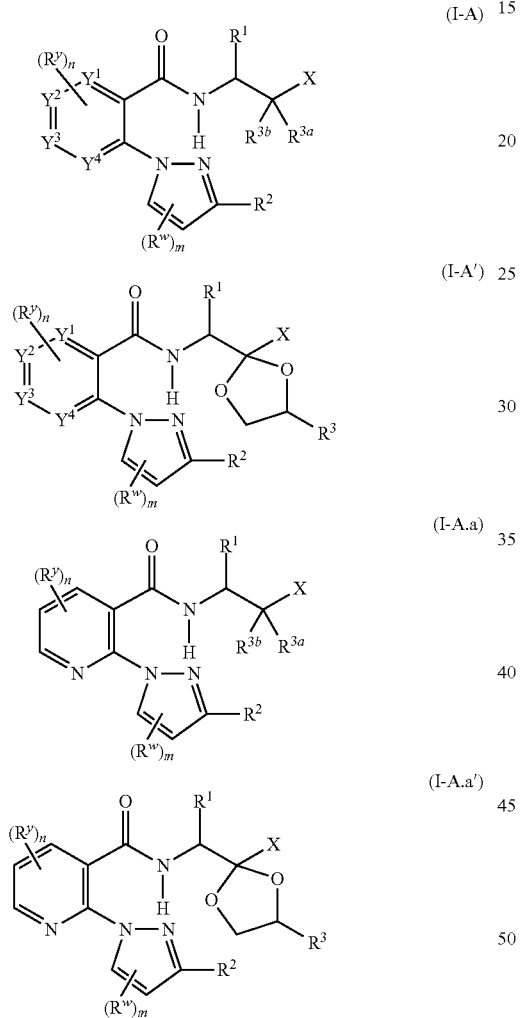

in which m, n, X, $Y^1$, $Y^2$, $Y^3$, $Y^4$, $R^1$, $R^2$, $R^3$, $R^{3a}$, $R^{3b}$, $R^y$ and $R^w$ have the aforementioned meanings, in particular the preferred meanings.

Amongst the compounds of the formulae I-A, I-A', I-A.a and I-A.a' particular preference is given to those, wherein the variables m, n, $R^1$, $R^2$, X in formulae I-A, I-A', I-A.a and I-A.a' individually or preferably in combination have the following meanings:

m is 0 or 1, in particular 0;
n is 0 or 1, in particular 0;
$R^1$ is phenyl-$C_1$-$C_4$-alkyl, in particular benzyl, where phenyl may be unsubstituted or carry 1, 2, 3 or 4 identical or different radicals $R^{1c}$;

$R^2$ is selected from aryl and hetaryl, specifically from phenyl, thienyl and pyridyl, where aryl and hetaryl (or phenyl, thienyl and pyridyl) may be unsubstituted or carry 1, 2, 3 or 4, in particular 1 or 2, identical or different radicals $R^{2b}$. Most preference is given to compounds of the general formulae I-A, I-A', I-A.a and I-A.a' in which $R^2$ is phenyl which is unsubstituted or carries 1, 2, 3 or 4, in particular 1 or 2, identical or different radicals $R^{2b}$;

X is a radical $C(=O)$—$NR^{x2}R^{x3}$ in which $R^{x2}$ and $R^{x3}$ have one of the aforementioned meanings. Compounds preferred among these are those in which:

$R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$. In particular, $R^{x2}$ is hydrogen, $C_1$-$C_6$-alkyl, $C_1$-$C_6$-haloalkyl, $C_1$-$C_6$-alkyl which has 1 or 2 substituents $R^{xa}$, $C_3$-$C_7$-cycloalkyl-$C_1$-$C_4$-alkyl, $C_3$-$C_7$-heterocycloalkyl-$C_1$-$C_4$-alkyl, aryl, hetaryl, aryl-$C_1$-$C_4$-alkyl or hetaryl-$C_1$-$C_4$-alkyl. $R^{x2}$ is very particularly preferably hydrogen.

$R^{x3}$ is H, $C_1$-$C_6$-alkyl, $C_1$-$C_6$-haloalkyl or $C_1$-$C_6$-alkyl which has 1, 2 or 3 substituents $R^{xa}$. In particular, $R^{x3}$ is hydrogen, $C_1$-$C_6$-alkyl, $C_1$-$C_6$-haloalkyl, $C_1$-$C_6$-alkyl which has 1 or 2 substituents $R^{xa}$. $R^{x3}$ is very particularly preferably hydrogen.

Compounds of the formulae I-A, I-A', I-A.a and I-A.a' which are likewise preferred are those in which the group $NR^{x2}R^{x3}$ is a nitrogen heterocycle of the following formulae:

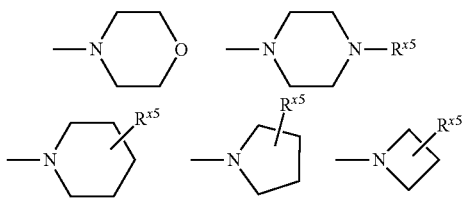

in which $R^{x5}$ is hydrogen or has the meaning indicated for $R^{xb}$. In particular, $R^{x5}$ is $C_1$-$C_6$-alkyl, $C_1$-$C_6$-haloalkyl, $C_1$-$C_6$-alkyl which has 1, 2 or 3 substituents $R^{xa}$, or $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl-$C_1$-$C_4$-alkyl or hetaryl-$C_1$-$C_4$-alkyl, where aryl and hetaryl in the last 2 radicals mentioned are unsubstituted or have 1, 2 or 3 substituents $R^{xd}$, or COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_6$-alkyl, CONH-phenyl, $SO_2NH$-phenyl, CONH-hetaryl, $SO_2NH$-hetaryl, where phenyl and hetaryl in the last 4 radicals mentioned are unsubstituted or may have 1, 2 or 3 substituents which are selected from the halogen, $C_1$-$C_4$-alkyl, $C_1$-$C_4$-haloalkyl, $C_1$-$C_4$-alkoxy and $C_1$-$C_4$-haloalkoxy. In particular, $R^{x5}$ is hydrogen or $C_1$-$C_4$-alkyl.

In a particularly preferred embodiment of the invention, X in formulae I-A, I-A', I-A.a and I-A.a' is $C(O)$—$NH_2$.

Likewise preferred are compounds of the formulae I, I', I-a and I-a' wherein W—$R^2$ is a radical W6, and particularly preferred among these are those in which m is 0 or 1 and specifically 0. The compounds of this particular preferred embodiment can be described by the following formulae I-B, I-B', I-B.a and I-B.a'

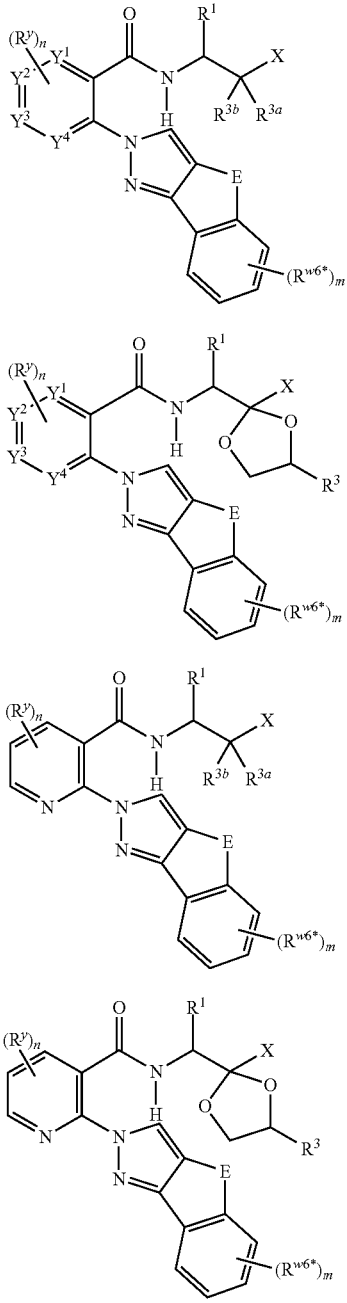

in which m, n, X, $Y^1$, $Y^2$, $Y^3$, $Y^4$, E, $R^1$, $R^2$, $R^3$, $R^{3a}$, $R^{3b}$, $R^y$ and $R^{w6*}$ have the aforementioned meanings, in particular the preferred meanings.

Amongst the compounds of the formulae I-B, I-B', I-B.a and I-B.a' particular preference is given to those, wherein the variables m, n, E, $R^1$, $R^2$, X in formulae I-B, I-B', I-B.a and I-B.a' individually or preferably in combination have the following meanings:

m is 0 or 1, in particular 0;
n is 0 or 1, in particular 0;

$R^1$ is phenyl-$C_1$-$C_4$-alkyl, in particular benzyl, where phenyl may be unsubstituted or carry 1, 2, 3 or 4 identical or different radicals $R^{1c}$;

$R^2$ is selected from aryl and hetaryl, specifically from phenyl, thienyl and pyridyl, where aryl and hetaryl (or phenyl, thienyl and pyridyl) may be unsubstituted or carry 1, 2, 3 or 4, in particular 1 or 2, identical or different radicals $R^{2b}$. Most preference is given to compounds of the general formulae I-B, I-B', I-B.a and I-B.a' in which $R^2$ is phenyl which is unsubstituted or carries 1, 2, 3 or 4, in particular 1 or 2, identical or different radicals $R^{2b}$;

X is a radical C(=O)—$NR^{x2}R^{x3}$ in which $R^{x2}$ and $R^{x3}$ have one of the aforementioned meanings. Compounds preferred among these are those in which:

$R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$. In particular, $R^{x2}$ is hydrogen, $C_1$-$C_6$-alkyl, $C_1$-$C_6$-haloalkyl, $C_1$-$C_6$-alkyl which has 1 or 2 substituents $R^{xa}$, $C_3$-$C_7$-cycloalkyl-$C_1$-$C_4$-alkyl, $C_3$-$C_7$-heterocycloalkyl-$C_1$-$C_4$-alkyl, aryl, hetaryl, aryl-$C_1$-$C_4$-alkyl or hetaryl-$C_1$-$C_4$-alkyl. $R^{x2}$ is very particularly preferably hydrogen.

$R^{x3}$ is H, $C_1$-$C_6$-alkyl, $C_1$-$C_6$-haloalkyl or $C_1$-$C_6$-alkyl which has 1, 2 or 3 substituents $R^{xa}$. In particular, $R^{x3}$ is hydrogen, $C_1$-$C_6$-alkyl, $C_1$-$C_6$-haloalkyl, $C_1$-$C_6$-alkyl which has 1 or 2 substituents $R^{xa}$. $R^{x3}$ is very particularly preferably hydrogen.

Compounds of the formulae I-B, I-B', I-B.a and I-B.a' which are likewise preferred are those in which the group $NR^{x2}R^{x3}$ is a nitrogen heterocycle of the following formulae:

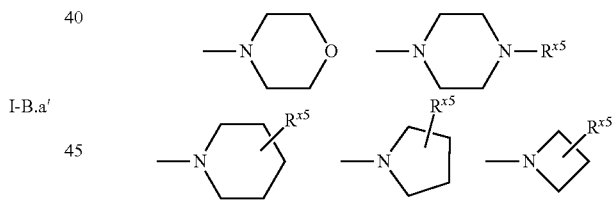

in which $R^{x5}$ is hydrogen or has the meaning indicated for $R^{xb}$. In particular, $R^{x5}$ is $C_1$-$C_6$-alkyl, $C_1$-$C_6$-haloalkyl, $C_1$-$C_6$-alkyl which has 1, 2 or 3 substituents $R^{xa}$, or $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl-$C_1$-$C_4$-alkyl or hetaryl-$C_1$-$C_4$-alkyl, where aryl and hetaryl in the last 2 radicals mentioned are unsubstituted or have 1, 2 or 3 substituents $R^{xd}$, or COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_6$-alkyl, CONH-phenyl, $SO_2NH$-phenyl, CONH-hetaryl, $SO_2NH$-hetaryl, where phenyl and hetaryl in the last 4 radicals mentioned are unsubstituted or may have 1, 2 or 3 substituents which are selected from the halogen, $C_1$-$C_4$-alkyl, $C_1$-$C_4$-haloalkyl, $C_1$-$C_4$-alkoxy and $C_1$-$C_4$-haloalkoxy. In particular, $R^{x5}$ is hydrogen or $C_1$-$C_4$-alkyl.

In a particularly preferred embodiment of the invention, X in formulae I-B, I-B', I-B.a and I-B.a' is C(O)—$NH_2$.

Where $R^y$ is present, $R^y$ is preferably selected from OH, F, Cl, $NH_2$, CN, $CF_3$, $CHF_2$, O—$CF_3$, O—$CHF_2$, O—$CH_2F$, $C_1$-$C_6$-alkyl, $C_3$-$C_7$-cycloalkyl, $C_1$-$C_6$-alkylamino, $C_1$-$C_6$-dialkylamino, pyrrolidinyl, piperidinyl, morpholinyl, imidazolyl, $C_1$-$C_4$-alkoxy, $C_1$-$C_4$-alkoxy-$C_1$-$C_4$-alkyl, $CONR^{y2}R^{y3}$, $SO_2NR^{y2}R^{y3}$, NH—$SO_2$—$R^{y4}$, —$(CH_2)_p$—$NR^{y6}R^{y7}$, NH—CO—$R^{y5}$, in which p is 0, 1, 2, 3, 4, or 5, and in which $R^{y2}$, $R^{y3}$, $R^{y4}$, $R^{y5}$, $R^{y6}$, $R^{y1}$ have the aforementioned meanings, preferably the meanings mentioned as preferred below, and are in particular H and $C_1$-$C_6$-alkyl, phenyl, benzyl and O-benzyl, where the phenyl ring in the last 3 groups mentioned may have 1, 2 or 3 substituents selected from halogen, OH, SH, $NO_2$, COOH, $C(O)NH_2$, CHO, CN, $NH_2$, $OCH_2COOH$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—$C(O)C_1$-$C_6$-alkyl, and $SO_2$—$C_1$-$C_6$-alkyl.

In particular, $R^y$ is OH, F, Cl, $NH_2$, CN, $CF_3$, $CHF_2$, O—$CF_3$, O—$CHF_2$, O—$CH_2F$, $C_1$-$C_6$-alkyl, $C_3$-$C_7$-cycloalkyl, $C_1$-$C_6$-alkylamino, $C_1$-$C_6$-dialkylamino, pyrrolidinyl, piperidinyl, morpholinyl, imidazolyl, $C_1$-$C_4$-alkoxy, $C_1$-$C_4$-alkoxy-$C_1$-$C_4$-alkyl, CONH—$C_1$-$C_6$-alkyl, $SO_2N(C_1$-$C_6$-alkyl$)_2$, NH—$SO_2$—$C_1$-$C_6$-alkyl, NH—CO—$C_1$-$C_6$-alkyl, $(CH_2)_p$—$N(C_1$-$C_6$-alkyl$)_2$, in which p is 2, 3 or 4.

$R^y$ is particularly preferably F, Cl, CN, $CF_3$, $CHF_2$, O—$CF_3$, O—$CHF_2$, O—$CH_2F$ or $C_1$-$C_3$-alkyl.

Otherwise, the radicals $R^{x4}$, $R^{ya}$, $R^{wa}$, $R_E^{1a}$, $R^{yb}$, $R^{wb}$, $R_E^{1b}$, $R^{yd}$, $R^{wd}$, $R_E^{1d}$, $R^{a1}$, $R^{b1}$, $R^{c1}$, $R^{y1}$, $R^{w1}$, $R^{a2}$, $R^{b2}$, $R^{c2}$, $R^{y2}$, $R^{w2}$, $R^{a3}$, $R^{b3}$, $R^{c3}$, $R^{y3}$, $R^{w3}$, $R^{a4}$, $R^{b4}$, $R^{c4}$, $R^{y4}$, $R^{w4}$, $R^{a5}$, $R^{b5}$, $R^{c5}$, $R^{y5}$, $R^{w5}$, $R^{a6}$, $R^{b6}$, $R^{c6}$, $R^{y6}$, $R^{w6}$, $R^{a7}$, $R^{b7}$, $R^{c7}$, $R^{y1}$ and $R^{w7}$ have, unless otherwise indicated, independently of one another preferably one of the following meanings:

$R^{x4}$: hydrogen or $C_1$-$C_6$-alkyl.

$R^{ya}$, $R^{wa}$, $R_E^{1a}$ independently of one another: $C_1$-$C_4$-alkoxy or $C_1$-$C_4$-haloalkoxy.

$R^{yb}$, $R^{wb}$, $R_E^{1b}$ independently of one another: halogen, $C_1$-$C_4$-alkyl, $C_1$-$C_4$-haloalkyl, $C_1$-$C_4$alkoxy or $C_1$-$C_4$-haloalkoxy.

$R^{yd}$, $R^{wd}$, $R_E^{1d}$ independently of one another: F, Cl, OH, COOH, $C(O)NH_2$, CN, $NH_2$, $OCH_2COOH$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, CO—$C_1$-$C_4$-alkyl, CO—O—$C_1$-$C_4$-alkyl, NH—$C_1$-$C_4$-alkyl, NH—$C(O)C_1$-$C_4$-alkyl or $SO_2$—$C_1$-$C_4$-alkyl.

$R^{a1}$, $R^{b1}$, $R^{c1}$, $R^{y1}$, $R^{w1}$ independently of one another: hydrogen, $C_1$-$C_6$-alkyl, $C_1$-$C_6$-haloalkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a2}$, $R^{b2}$, $R^{c2}$, $R^{y2}$, $R^{w2}$ independently of one another: hydrogen, $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a3}$, $R^{b3}$, $R^{c3}$, $R^{y3}$, $R^{w3}$ independently of one another: hydrogen or $C_1$-$C_6$-alkyl, or $R^{a2}$ with $R^{a3}$ (and likewise $R^{b2}$ with $R^{b3}$, $R^{c2}$ with $R^{c3}$, $R^{y2}$ with $R^{y3}$ and $R^{w2}$ with $R^{w3}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

$R^{a4}$, $R^{b4}$, $R^{c4}$, $R^{y4}$, $R^{w4}$ independently of one another: hydrogen, $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a5}$, $R^{b5}$, $R^{c5}$, $R^{y5}$, $R^{w5}$ independently of one another: hydrogen, $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a6}$, $R^{b6}$, $R^{c6}$, $R^{y6}$, $R^{w6}$ independently of one another: hydrogen, $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a7}$, $R^{b7}$, $R^{c7}$, $R^{y7}$, $R^{w7}$ independently of one another: hydrogen or $C_1$-$C_6$-alkyl, or $R^{a6}$ with $R^{a7}$ (and likewise $R^{b6}$ with $R^{b7}$, $R^{c6}$ with $R^{c7}$, $R^{y6}$ with $R^{y7}$ and $R^{w6}$ with $R^{w7}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

The compounds of the general formula I-a' which are indicated in Tables 1 to 20 below, and their tautomers and pharmaceutically acceptable salts, represent per se preferred embodiments of the present invention. The meanings for $R^1$, $R^2$ and W indicated in Table A below represent embodiments of the invention which are likewise preferred independently of one another and especially in combination.

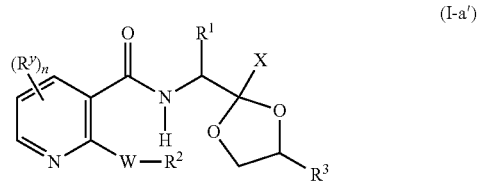

(I-a')

Table 1

Compounds of the formula I-a' in which n=0, i.e. $(R^y)_n$ is absent, X is carbamoyl, $R^3$ is hydrogen and the combination of $R^1$, $R^2$ and W for a compound in each case corresponds to one line of Table A.

Table 2

Compounds of the formula I-a' in which X is carbamoyl, $R^3$ is hydrogen, $(R^y)_n$ is 5-F, and the combination of $R^1$, $R^2$ and W for a compound in each case corresponds to one line of Table A.

Table 3

Compounds of the formula I-a' in which X is carbamoyl, $R^3$ is hydrogen, $(R^y)_n$ is 5-Cl, and the combination of $R^1$, $R^2$ and W for a compound in each case corresponds to one line of Table A.

Table 4

Compounds of the formula I-a' in which X is carbamoyl, $R^3$ is hydrogen, $(R^y)_n$ is 5-CN, and the combination of $R^1$, $R^2$ and W for a compound in each case corresponds to one line of Table A.

Table 5
Compounds of the formula I-a' in which X is carbamoyl, $R^3$ is hydrogen, $(R^y)_n$ is 5-CH$_3$, and the combination of $R^1$, $R^2$ and W for a compound in each case corresponds to one line of Table A.

Table 6
Compounds of the formula I-a' in which $R^3$ is hydrogen, X is —C(O)NHCH$_3$, n=0, i.e. $(R^y)_n$ is absent, and the combination of $R^1$, $R^2$ and W for a compound in each case corresponds to one line of Table A.

Table 7
Compounds of the formula I-a' in which $R^3$ is hydrogen, X is —C(O)NHCH$_3$, $(R^y)_n$ is 5-F, and the combination of $R^1$, $R^2$ and W for a compound in each case corresponds to one line of Table A.

Table 8
Compounds of the formula I-a' in which $R^3$ is hydrogen, X is —C(O)NHCH$_3$, $(R^y)_n$ is 5-Cl, and the combination of $R^1$, $R^2$ and W for a compound in each case corresponds to one line of Table A.

Table 9
Compounds of the formula I-a' in which $R^3$ is hydrogen, X is —C(O)NHCH$_3$, $(R^y)_n$ is 5-CN, and the combination of $R^1$, $R^2$ and W for a compound in each case corresponds to one line of Table A.

Table 10
Compounds of the formula I-a' in which $R^3$ is hydrogen, X is —C(O)NHCH$_3$, $(R^y)_n$ is 5-CH$_3$, and the combination of $R^1$, $R^2$ and W for a compound in each case corresponds to one line of Table A.

Table 11
Compounds of the formula I-a' in which the $R^3$ is methyl, X is carbamoyl, n=0, i.e. $(R^y)_n$ is absent, and the combination of $R^1$, $R^2$ and W for a compound in each case corresponds to one line of Table A.

Table 12
Compounds of the formula I-a' in which the $R^3$ is methyl, X is carbamoyl, $(R^y)_n$ is 5-F, and the combination of $R^1$, $R^2$ and W for a compound in each case corresponds to one line of Table A.

Table 13
Compounds of the formula I-a' in which the $R^3$ is methyl, X is carbamoyl, $(R^y)_n$ is 5-Cl, and the combination of $R^1$, $R^2$ and W for a compound in each case corresponds to one line of Table A.

Table 14
Compounds of the formula I-a' in which the $R^3$ is methyl, X is carbamoyl, $(R^y)_n$ is 5-CN, and the combination of $R^1$, $R^2$ and W for a compound in each case corresponds to one line of Table A.

Table 15
Compounds of the formula I-a' in which the $R^3$ is methyl, X is carbamoyl, $(R^y)_n$ is 5-CH$_3$, and the combination of $R^1$, $R^2$ and W for a compound in each case corresponds to one line of Table A.

Table 16
Compounds of the formula I-a' in which the $R^3$ is methyl, X is —C(O)NHCH$_3$, n=0, i.e. $(R^y)_n$ is absent, and the combination of $R^1$, $R^2$ and W for a compound in each case corresponds to one line of Table A.

Table 17
Compounds of the formula I-a' in which the $R^3$ is methyl, X is —C(O)NHCH$_3$, $(R^y)_n$ is 5-F, and the combination of $R^1$, $R^2$ and W for a compound in each case corresponds to one line of Table A.

Table 18
Compounds of the formula I-a' in which the $R^3$ is methyl, X is —C(O)NHCH$_3$, $(R^y)_n$ is 5-Cl, and the combination of $R^1$, $R^2$ and W for a compound in each case corresponds to one line of Table A.

Table 19
Compounds of the formula I-a' in which the $R^3$ is methyl, X is —C(O)NHCH$_3$, $(R^y)_n$ is 5-CN, and the combination of $R^1$, $R^2$ and W for a compound in each case corresponds to one line of Table A.

Table 20
Compounds of the formula I-a' in which the $R^3$ is methyl, X is —C(O)NHCH$_3$, $(R^y)_n$ is 5-CH$_3$, and the combination of $R^1$, $R^2$ and W for a compound in each case corresponds to one line of Table A.

TABLE A

| No. | $R^1$ | $R^2$ | W |
|---|---|---|---|
| A-1 | n-Butyl | Phenyl | W1a (m = 0) |
| A-2 | n-Butyl | 2-Methylphenyl | W1a (m = 0) |
| A-3 | n-Butyl | 2-Methoxyphenyl | W1a (m = 0) |
| A-4 | n-Butyl | 2-Chlorophenyl | W1a (m = 0) |
| A-5 | n-Butyl | 2-Fluorophenyl | W1a (m = 0) |
| A-6 | n-Butyl | 2-Trifluoromethylphenyl | W1a (m = 0) |
| A-7 | n-Butyl | 3-Methylphenyl | W1a (m = 0) |
| A-8 | n-Butyl | 3-Methoxyphenyl | W1a (m = 0) |
| A-9 | n-Butyl | 3-Chlorophenyl | W1a (m = 0) |
| A-10 | n-Butyl | 3-Fluorophenyl | W1a (m = 0) |
| A-11 | n-Butyl | 3-Trifluoromethylphenyl | W1a (m = 0) |
| A-12 | n-Butyl | 3-[(Phenylmethyl)oxy]phenyl | W1a (m = 0) |
| A-13 | n-Butyl | 3-Morpholin-4-ylphenyl | W1a (m = 0) |
| A-14 | n-Butyl | 3-(Morpholin-4-ylmethyl)phenyl | W1a (m = 0) |
| A-15 | n-Butyl | 3-Pyrrolidin-1-ylphenyl | W1a (m = 0) |
| A-16 | n-Butyl | 4-Methylphenyl | W1a (m = 0) |
| A-17 | n-Butyl | 4-(1-Methylethyl)phenyl | W1a (m = 0) |
| A-18 | n-Butyl | 4-Methoxyphenyl | W1a (m = 0) |
| A-19 | n-Butyl | 4-Chlorophenyl | W1a (m = 0) |
| A-20 | n-Butyl | 4-Fluorophenyl | W1a (m = 0) |
| A-21 | n-Butyl | 4-Trifluoromethylphenyl | W1a (m = 0) |
| A-22 | n-Butyl | 4-Diethylaminophenyl | W1a (m = 0) |
| A-23 | n-Butyl | 4-[(Diethylamino)methyl]phenyl | W1a (m = 0) |
| A-24 | n-Butyl | 4-Cyanophenyl | W1a (m = 0) |
| A-25 | n-Butyl | 4-(Piperidin-1-yl)phenyl | W1a (m = 0) |
| A-26 | n-Butyl | 4-(4-Methylpiperazin-1-yl)phenyl | W1a (m = 0) |
| A-27 | n-Butyl | 4-Pyrrolidin-1-ylphenyl | W1a (m = 0) |

TABLE A-continued

| No. | R¹ | R² | W |
|---|---|---|---|
| A-28 | n-Butyl | 4-(1H-Imidazol-1-yl)phenyl | W1a (m = 0) |
| A-29 | n-Butyl | 4-Morpholin-4-ylphenyl | W1a (m = 0) |
| A-30 | n-Butyl | 4-(Morpholin-4-ylmethyl)phenyl | W1a (m = 0) |
| A-31 | n-Butyl | 2,4-Difluorophenyl | W1a (m = 0) |
| A-32 | n-Butyl | 2,6-Difluorophenyl | W1a (m = 0) |
| A-33 | n-Butyl | 3,5-Difluorophenyl | W1a (m = 0) |
| A-34 | n-Butyl | 2,4-Dichlorophenyl | W1a (m = 0) |
| A-35 | n-Butyl | 2,6-Dichlorophenyl | W1a (m = 0) |
| A-36 | n-Butyl | 3,5-Dichlorophenyl | W1a (m = 0) |
| A-37 | n-Butyl | 2-Chloro-4-fluorophenyl | W1a (m = 0) |
| A-38 | n-Butyl | 2-Chloro-4-morpholin-4-ylphenyl | W1a (m = 0) |
| A-39 | n-Butyl | 2-Fluoro-4-morpholin-4-ylphenyl | W1a (m = 0) |
| A-40 | n-Butyl | Pyridin-2-yl | W1a (m = 0) |
| A-41 | n-Butyl | Pyridin-4-yl | W1a (m = 0) |
| A-42 | n-Butyl | Thien-2-yl | W1a (m = 0) |
| A-43 | n-Butyl | 2,3-Dihydrobenzo[b]furan-5-yl | W1a (m = 0) |
| A-44 | Isobutyl | Phenyl | W1a (m = 0) |
| A-45 | Isobutyl | 2-Methylphenyl | W1a (m = 0) |
| A-46 | Isobutyl | 2-Methoxyphenyl | W1a (m = 0) |
| A-47 | Isobutyl | 2-Chlorophenyl | W1a (m = 0) |
| A-48 | Isobutyl | 2-Fluorophenyl | W1a (m = 0) |
| A-49 | Isobutyl | 2-Trifluoromethylphenyl | W1a (m = 0) |
| A-50 | Isobutyl | 3-Methylphenyl | W1a (m = 0) |
| A-51 | Isobutyl | 3-Methoxyphenyl | W1a (m = 0) |
| A-52 | Isobutyl | 3-Chlorophenyl | W1a (m = 0) |
| A-53 | Isobutyl | 3-Fluorophenyl | W1a (m = 0) |
| A-54 | Isobutyl | 3-Trifluoromethylphenyl | W1a (m = 0) |
| A-55 | Isobutyl | 3-[(Phenylmethyl)oxy]phenyl | W1a (m = 0) |
| A-56 | Isobutyl | 3-Morpholin-4-ylphenyl | W1a (m = 0) |
| A-57 | Isobutyl | 3-(Morpholin-4-ylmethyl)phenyl | W1a (m = 0) |
| A-58 | Isobutyl | 3-Pyrrolidin-1-ylphenyl | W1a (m = 0) |
| A-59 | Isobutyl | 4-Methylphenyl | W1a (m = 0) |
| A-60 | Isobutyl | 4-(1-Methylethyl)phenyl | W1a (m = 0) |
| A-61 | Isobutyl | 4-Methoxyphenyl | W1a (m = 0) |
| A-62 | Isobutyl | 4-Chlorophenyl | W1a (m = 0) |
| A-63 | Isobutyl | 4-Fluorophenyl | W1a (m = 0) |
| A-64 | Isobutyl | 4-Trifluoromethylphenyl | W1a (m = 0) |
| A-65 | Isobutyl | 4-Diethylaminophenyl | W1a (m = 0) |
| A-66 | Isobutyl | 4-[(Diethylamino)methyl]phenyl | W1a (m = 0) |
| A-67 | Isobutyl | 4-Cyanophenyl | W1a (m = 0) |
| A-68 | Isobutyl | 4-(Piperidin-1-yl)phenyl | W1a (m = 0) |
| A-69 | Isobutyl | 4-(4-Methylpiperazin-1-yl)phenyl | W1a (m = 0) |
| A-70 | Isobutyl | 4-Pyrrolidin-1-ylphenyl | W1a (m = 0) |
| A-71 | Isobutyl | 4-(1H-Imidazol-1-yl)phenyl | W1a (m = 0) |
| A-72 | Isobutyl | 4-Morpholin-4-ylphenyl | W1a (m = 0) |
| A-73 | Isobutyl | 4-(Morpholin-4-ylmethyl)phenyl | W1a (m = 0) |
| A-74 | Isobutyl | 2,4-Difluorophenyl | W1a (m = 0) |
| A-75 | Isobutyl | 2,6-Difluorophenyl | W1a (m = 0) |
| A-76 | Isobutyl | 3,5-Difluorophenyl | W1a (m = 0) |
| A-77 | Isobutyl | 2,4-Dichlorophenyl | W1a (m = 0) |
| A-78 | Isobutyl | 2,6-Dichlorophenyl | W1a (m = 0) |
| A-79 | Isobutyl | 3,5-Dichlorophenyl | W1a (m = 0) |
| A-80 | Isobutyl | 2-Chloro-4-fluorophenyl | W1a (m = 0) |
| A-81 | Isobutyl | 2-Chloro-4-morpholin-4-ylphenyl | W1a (m = 0) |
| A-82 | Isobutyl | 2-Fluoro-4-morpholin-4-ylphenyl | W1a (m = 0) |
| A-83 | Isobutyl | Pyridin-2-yl | W1a (m = 0) |
| A-84 | Isobutyl | Pyridin-4-yl | W1a (m = 0) |
| A-85 | Isobutyl | Thien-2-yl | W1a (m = 0) |
| A-86 | Isobutyl | 2,3-Dihydrobenzo[b]furan-5-yl | W1a (m = 0) |
| A-87 | Benzyl | Phenyl | W1a (m = 0) |
| A-88 | Benzyl | 2-Methylphenyl | W1a (m = 0) |
| A-89 | Benzyl | 2-Methoxyphenyl | W1a (m = 0) |
| A-90 | Benzyl | 2-Chlorophenyl | W1a (m = 0) |
| A-91 | Benzyl | 2-Fluorophenyl | W1a (m = 0) |
| A-92 | Benzyl | 2-Trifluoromethylphenyl | W1a (m = 0) |
| A-93 | Benzyl | 3-Methylphenyl | W1a (m = 0) |
| A-94 | Benzyl | 3-Methoxyphenyl | W1a (m = 0) |
| A-95 | Benzyl | 3-Chlorophenyl | W1a (m = 0) |
| A-96 | Benzyl | 3-Fluorophenyl | W1a (m = 0) |
| A-97 | Benzyl | 3-Trifluoromethylphenyl | W1a (m = 0) |
| A-98 | Benzyl | 3-[(Phenylmethyl)oxy]phenyl | W1a (m = 0) |
| A-99 | Benzyl | 3-Morpholin-4-ylphenyl | W1a (m = 0) |
| A-100 | Benzyl | 3-(Morpholin-4-ylmethyl)phenyl | W1a (m = 0) |
| A-101 | Benzyl | 3-Pyrrolidin-1-ylphenyl | W1a (m = 0) |
| A-102 | Benzyl | 4-Methylphenyl | W1a (m = 0) |
| A-103 | Benzyl | 4-(1-Methylethyl)phenyl | W1a (m = 0) |
| A-104 | Benzyl | 4-Methoxyphenyl | W1a (m = 0) |
| A-105 | Benzyl | 4-Chlorophenyl | W1a (m = 0) |

TABLE A-continued

| No. | R¹ | R² | W |
|---|---|---|---|
| A-106 | Benzyl | 4-Fluorophenyl | W1a (m = 0) |
| A-107 | Benzyl | 4-Trifluoromethylphenyl | W1a (m = 0) |
| A-108 | Benzyl | 4-Diethylaminophenyl | W1a (m = 0) |
| A-109 | Benzyl | 4-[(Diethylamino)methyl]phenyl | W1a (m = 0) |
| A-110 | Benzyl | 4-Cyanophenyl | W1a (m = 0) |
| A-111 | Benzyl | 4-(Piperidin-1-yl)phenyl | W1a (m = 0) |
| A-112 | Benzyl | 4-(4-Methylpiperazin-1-yl)phenyl | W1a (m = 0) |
| A-113 | Benzyl | 4-Pyrrolidin-1-ylphenyl | W1a (m = 0) |
| A-114 | Benzyl | 4-(1H-Imidazol-1-yl)phenyl | W1a (m = 0) |
| A-115 | Benzyl | 4-Morpholin-4-ylphenyl | W1a (m = 0) |
| A-116 | Benzyl | 4-(Morpholin-4-ylmethyl)phenyl | W1a (m = 0) |
| A-117 | Benzyl | 2,4-Difluorophenyl | W1a (m = 0) |
| A-118 | Benzyl | 2,6-Difluorophenyl | W1a (m = 0) |
| A-119 | Benzyl | 3,5-Difluorophenyl | W1a (m = 0) |
| A-120 | Benzyl | 2,4-Dichlorophenyl | W1a (m = 0) |
| A-121 | Benzyl | 2,6-Dichlorophenyl | W1a (m = 0) |
| A-122 | Benzyl | 3,5-Dichlorophenyl | W1a (m = 0) |
| A-123 | Benzyl | 2-Chloro-4-fluorophenyl | W1a (m = 0) |
| A-124 | Benzyl | 2-Chloro-4-morpholin-4-ylphenyl | W1a (m = 0) |
| A-125 | Benzyl | 2-Fluoro-4-morpholin-4-ylphenyl | W1a (m = 0) |
| A-126 | Benzyl | Pyridin-2-yl | W1a (m = 0) |
| A-127 | Benzyl | Pyridin-4-yl | W1a (m = 0) |
| A-128 | Benzyl | Thien-2-yl | W1a (m = 0) |
| A-129 | Benzyl | 2,3-Dihydrobenzo[b]furan-5-yl | W1a (m = 0) |
| A-130 | 4-Chlorobenzyl | Phenyl | W1a (m = 0) |
| A-131 | 4-Chlorobenzyl | 2-Methylphenyl | W1a (m = 0) |
| A-132 | 4-Chlorobenzyl | 2-Methoxyphenyl | W1a (m = 0) |
| A-133 | 4-Chlorobenzyl | 2-Chlorophenyl | W1a (m = 0) |
| A-134 | 4-Chlorobenzyl | 2-Fluorophenyl | W1a (m = 0) |
| A-135 | 4-Chlorobenzyl | 2-Trifluoromethylphenyl | W1a (m = 0) |
| A-136 | 4-Chlorobenzyl | 3-Methylphenyl | W1a (m = 0) |
| A-137 | 4-Chlorobenzyl | 3-Methoxyphenyl | W1a (m = 0) |
| A-138 | 4-Chlorobenzyl | 3-Chlorophenyl | W1a (m = 0) |
| A-139 | 4-Chlorobenzyl | 3-Fluorophenyl | W1a (m = 0) |
| A-140 | 4-Chlorobenzyl | 3-Trifluoromethylphenyl | W1a (m = 0) |
| A-141 | 4-Chlorobenzyl | 3-[(Phenylmethyl)oxy]phenyl | W1a (m = 0) |
| A-142 | 4-Chlorobenzyl | 3-Morpholin-4-ylphenyl | W1a (m = 0) |
| A-143 | 4-Chlorobenzyl | 3-(Morpholin-4-ylmethyl)phenyl | W1a (m = 0) |
| A-144 | 4-Chlorobenzyl | 3-Pyrrolidin-1-ylphenyl | W1a (m = 0) |
| A-145 | 4-Chlorobenzyl | 4-Methylphenyl | W1a (m = 0) |
| A-146 | 4-Chlorobenzyl | 4-(1-Methylethyl)phenyl | W1a (m = 0) |
| A-147 | 4-Chlorobenzyl | 4-Methoxyphenyl | W1a (m = 0) |
| A-148 | 4-Chlorobenzyl | 4-Chlorophenyl | W1a (m = 0) |
| A-149 | 4-Chlorobenzyl | 4-Fluorophenyl | W1a (m = 0) |
| A-150 | 4-Chlorobenzyl | 4-Trifluoromethylphenyl | W1a (m = 0) |
| A-151 | 4-Chlorobenzyl | 4-Diethylaminophenyl | W1a (m = 0) |
| A-152 | 4-Chlorobenzyl | 4-[(Diethylamino)methyl]phenyl | W1a (m = 0) |
| A-153 | 4-Chlorobenzyl | 4-Cyanophenyl | W1a (m = 0) |
| A-154 | 4-Chlorobenzyl | 4-(Piperidin-1-yl)phenyl | W1a (m = 0) |
| A-155 | 4-Chlorobenzyl | 4-(4-Methylpiperazin-1-yl)phenyl | W1a (m = 0) |
| A-156 | 4-Chlorobenzyl | 4-Pyrrolidin-1-ylphenyl | W1a (m = 0) |
| A-157 | 4-Chlorobenzyl | 4-(1H-Imidazol-1-yl)phenyl | W1a (m = 0) |
| A-158 | 4-Chlorobenzyl | 4-Morpholin-4-ylphenyl | W1a (m = 0) |
| A-159 | 4-Chlorobenzyl | 4-(Morpholin-4-ylmethyl)phenyl | W1a (m = 0) |
| A-160 | 4-Chlorobenzyl | 2,4-Difluorophenyl | W1a (m = 0) |
| A-161 | 4-Chlorobenzyl | 2,6-Difluorophenyl | W1a (m = 0) |
| A-162 | 4-Chlorobenzyl | 3,5-Difluorophenyl | W1a (m = 0) |
| A-163 | 4-Chlorobenzyl | 2,4-Dichlorophenyl | W1a (m = 0) |
| A-164 | 4-Chlorobenzyl | 2,6-Dichlorophenyl | W1a (m = 0) |
| A-165 | 4-Chlorobenzyl | 3,5-Dichlorophenyl | W1a (m = 0) |
| A-166 | 4-Chlorobenzyl | 2-Chloro-4-fluorophenyl | W1a (m = 0) |
| A-167 | 4-Chlorobenzyl | 2-Chloro-4-morpholin-4-ylphenyl | W1a (m = 0) |
| A-168 | 4-Chlorobenzyl | 2-Fluoro-4-morpholin-4-ylphenyl | W1a (m = 0) |
| A-169 | 4-Chlorobenzyl | Pyridin-2-yl | W1a (m = 0) |
| A-170 | 4-Chlorobenzyl | Pyridin-4-yl | W1a (m = 0) |
| A-171 | 4-Chlorobenzyl | Thien-2-yl | W1a (m = 0) |
| A-172 | 4-Chlorobenzyl | 2,3-Dihydrobenzo[b]furan-5-yl | W1a (m = 0) |
| A-173 | 4-Fluorbenzyl | Phenyl | W1a (m = 0) |
| A-174 | 4-Fluorbenzyl | 2-Methylphenyl | W1a (m = 0) |
| A-175 | 4-Fluorbenzyl | 2-Methoxyphenyl | W1a (m = 0) |
| A-176 | 4-Fluorbenzyl | 2-Chlorophenyl | W1a (m = 0) |
| A-177 | 4-Fluorbenzyl | 2-Fluorophenyl | W1a (m = 0) |
| A-178 | 4-Fluorbenzyl | 2-Trifluoromethylphenyl | W1a (m = 0) |
| A-179 | 4-Fluorbenzyl | 3-Methylphenyl | W1a (m = 0) |
| A-180 | 4-Fluorbenzyl | 3-Methoxyphenyl | W1a (m = 0) |
| A-181 | 4-Fluorbenzyl | 3-Chlorophenyl | W1a (m = 0) |
| A-182 | 4-Fluorbenzyl | 3-Fluorophenyl | W1a (m = 0) |
| A-183 | 4-Fluorbenzyl | 3-Trifluoromethylphenyl | W1a (m = 0) |

TABLE A-continued

| No. | R¹ | R² | W |
|---|---|---|---|
| A-184 | 4-Fluorbenzyl | 3-[(Phenylmethyl)oxy]phenyl | W1a (m = 0) |
| A-185 | 4-Fluorbenzyl | 3-Morpholin-4-ylphenyl | W1a (m = 0) |
| A-186 | 4-Fluorbenzyl | 3-(Morpholin-4-ylmethyl)phenyl | W1a (m = 0) |
| A-187 | 4-Fluorbenzyl | 3-Pyrrolidin-1-ylphenyl | W1a (m = 0) |
| A-188 | 4-Fluorbenzyl | 4-Methylphenyl | W1a (m = 0) |
| A-189 | 4-Fluorbenzyl | 4-(1-Methylethyl)phenyl | W1a (m = 0) |
| A-190 | 4-Fluorbenzyl | 4-Methoxyphenyl | W1a (m = 0) |
| A-191 | 4-Fluorbenzyl | 4-Chlorophenyl | W1a (m = 0) |
| A-192 | 4-Fluorbenzyl | 4-Fluorophenyl | W1a (m = 0) |
| A-193 | 4-Fluorbenzyl | 4-Trifluoromethylphenyl | W1a (m = 0) |
| A-194 | 4-Fluorbenzyl | 4-Diethylaminophenyl | W1a (m = 0) |
| A-195 | 4-Fluorbenzyl | 4-[(Diethylamino)methyl]phenyl | W1a (m = 0) |
| A-196 | 4-Fluorbenzyl | 4-Cyanophenyl | W1a (m = 0) |
| A-197 | 4-Fluorbenzyl | 4-(Piperidin-1-yl)phenyl | W1a (m = 0) |
| A-198 | 4-Fluorbenzyl | 4-(4-Methylpiperazin-1-yl)phenyl | W1a (m = 0) |
| A-199 | 4-Fluorbenzyl | 4-Pyrrolidin-1-ylphenyl | W1a (m = 0) |
| A-200 | 4-Fluorbenzyl | 4-(1H-Imidazol-1-yl)phenyl | W1a (m = 0) |
| A-201 | 4-Fluorbenzyl | 4-Morpholin-4-ylphenyl | W1a (m = 0) |
| A-202 | 4-Fluorbenzyl | 4-(Morpholin-4-ylmethyl)phenyl | W1a (m = 0) |
| A-203 | 4-Fluorbenzyl | 2,4-Difluorophenyl | W1a (m = 0) |
| A-204 | 4-Fluorbenzyl | 2,6-Difluorophenyl | W1a (m = 0) |
| A-205 | 4-Fluorbenzyl | 3,5-Difluorophenyl | W1a (m = 0) |
| A-206 | 4-Fluorbenzyl | 2,4-Dichlorophenyl | W1a (m = 0) |
| A-207 | 4-Fluorbenzyl | 2,6-Dichlorophenyl | W1a (m = 0) |
| A-208 | 4-Fluorbenzyl | 3,5-Dichlorophenyl | W1a (m = 0) |
| A-209 | 4-Fluorbenzyl | 2-Chloro-4-fluorophenyl | W1a (m = 0) |
| A-210 | 4-Fluorbenzyl | 2-Chloro-4-morpholin-4-ylphenyl | W1a (m = 0) |
| A-211 | 4-Fluorbenzyl | 2-Fluoro-4-morpholin-4-ylphenyl | W1a (m = 0) |
| A-212 | 4-Fluorbenzyl | Pyridin-2-yl | W1a (m = 0) |
| A-213 | 4-Fluorbenzyl | Pyridin-4-yl | W1a (m = 0) |
| A-214 | 4-Fluorbenzyl | Thien-2-yl | W1a (m = 0) |
| A-215 | 4-Fluorbenzyl | 2,3-Dihydrobenzo[b]furan-5-yl | W1a (m = 0) |
| A-216 | 4-Methoxybenzyl | Phenyl | W1a (m = 0) |
| A-217 | 4-Methoxybenzyl | 2-Methylphenyl | W1a (m = 0) |
| A-218 | 4-Methoxybenzyl | 2-Methoxyphenyl | W1a (m = 0) |
| A-219 | 4-Methoxybenzyl | 2-Chlorophenyl | W1a (m = 0) |
| A-220 | 4-Methoxybenzyl | 2-Fluorophenyl | W1a (m = 0) |
| A-221 | 4-Methoxybenzyl | 2-Trifluoromethylphenyl | W1a (m = 0) |
| A-222 | 4-Methoxybenzyl | 3-Methylphenyl | W1a (m = 0) |
| A-223 | 4-Methoxybenzyl | 3-Methoxyphenyl | W1a (m = 0) |
| A-224 | 4-Methoxybenzyl | 3-Chlorophenyl | W1a (m = 0) |
| A-225 | 4-Methoxybenzyl | 3-Fluorophenyl | W1a (m = 0) |
| A-226 | 4-Methoxybenzyl | 3-Trifluoromethylphenyl | W1a (m = 0) |
| A-227 | 4-Methoxybenzyl | 3-[(Phenylmethyl)oxy]phenyl | W1a (m = 0) |
| A-228 | 4-Methoxybenzyl | 3-Morpholin-4-ylphenyl | W1a (m = 0) |
| A-229 | 4-Methoxybenzyl | 3-(Morpholin-4-ylmethyl)phenyl | W1a (m = 0) |
| A-230 | 4-Methoxybenzyl | 3-Pyrrolidin-1-ylphenyl | W1a (m = 0) |
| A-231 | 4-Methoxybenzyl | 4-Methylphenyl | W1a (m = 0) |
| A-232 | 4-Methoxybenzyl | 4-(1-Methylethyl)phenyl | W1a (m = 0) |
| A-233 | 4-Methoxybenzyl | 4-Methoxyphenyl | W1a (m = 0) |
| A-234 | 4-Methoxybenzyl | 4-Chlorophenyl | W1a (m = 0) |
| A-235 | 4-Methoxybenzyl | 4-Fluorophenyl | W1a (m = 0) |
| A-236 | 4-Methoxybenzyl | 4-Trifluoromethylphenyl | W1a (m = 0) |
| A-237 | 4-Methoxybenzyl | 4-Diethylaminophenyl | W1a (m = 0) |
| A-238 | 4-Methoxybenzyl | 4-[(Diethylamino)methyl]phenyl | W1a (m = 0) |
| A-239 | 4-Methoxybenzyl | 4-Cyanophenyl | W1a (m = 0) |
| A-240 | 4-Methoxybenzyl | 4-(Piperidin-1-yl)phenyl | W1a (m = 0) |
| A-241 | 4-Methoxybenzyl | 4-(4-Methylpiperazin-1-yl)phenyl | W1a (m = 0) |
| A-242 | 4-Methoxybenzyl | 4-Pyrrolidin-1-ylphenyl | W1a (m = 0) |
| A-243 | 4-Methoxybenzyl | 4-(1H-Imidazol-1-yl)phenyl | W1a (m = 0) |
| A-244 | 4-Methoxybenzyl | 4-Morpholin-4-ylphenyl | W1a (m = 0) |
| A-245 | 4-Methoxybenzyl | 4-(Morpholin-4-ylmethyl)phenyl | W1a (m = 0) |
| A-246 | 4-Methoxybenzyl | 2,4-Difluorophenyl | W1a (m = 0) |
| A-247 | 4-Methoxybenzyl | 2,6-Difluorophenyl | W1a (m = 0) |
| A-248 | 4-Methoxybenzyl | 3,5-Difluorophenyl | W1a (m = 0) |
| A-249 | 4-Methoxybenzyl | 2,4-Dichlorophenyl | W1a (m = 0) |
| A-250 | 4-Methoxybenzyl | 2,6-Dichlorophenyl | W1a (m = 0) |
| A-251 | 4-Methoxybenzyl | 3,5-Dichlorophenyl | W1a (m = 0) |
| A-252 | 4-Methoxybenzyl | 2-Chloro-4-fluorophenyl | W1a (m = 0) |
| A-253 | 4-Methoxybenzyl | 2-Chloro-4-morpholin-4-ylphenyl | W1a (m = 0) |
| A-254 | 4-Methoxybenzyl | 2-Fluoro-4-morpholin-4-ylphenyl | W1a (m = 0) |
| A-255 | 4-Methoxybenzyl | Pyridin-2-yl | W1a (m = 0) |
| A-256 | 4-Methoxybenzyl | Pyridin-4-yl | W1a (m = 0) |
| A-257 | 4-Methoxybenzyl | Thien-2-yl | W1a (m = 0) |
| A-258 | 4-Methoxybenzyl | 2,3-Dihydrobenzo[b]furan-5-yl | W1a (m = 0) |
| A-259 | Cyclohexylmethyl | Phenyl | W1a (m = 0) |
| A-260 | Cyclohexylmethyl | 2-Methylphenyl | W1a (m = 0) |
| A-261 | Cyclohexylmethyl | 2-Methoxyphenyl | W1a (m = 0) |

TABLE A-continued

| No. | R¹ | R² | W |
|---|---|---|---|
| A-262 | Cyclohexylmethyl | 2-Chlorophenyl | W1a (m = 0) |
| A-263 | Cyclohexylmethyl | 2-Fluorophenyl | W1a (m = 0) |
| A-264 | Cyclohexylmethyl | 2-Trifluoromethylphenyl | W1a (m = 0) |
| A-265 | Cyclohexylmethyl | 3-Methylphenyl | W1a (m = 0) |
| A-266 | Cyclohexylmethyl | 3-Methoxyphenyl | W1a (m = 0) |
| A-267 | Cyclohexylmethyl | 3-Chlorophenyl | W1a (m = 0) |
| A-268 | Cyclohexylmethyl | 3-Fluorophenyl | W1a (m = 0) |
| A-269 | Cyclohexylmethyl | 3-Trifluoromethylphenyl | W1a (m = 0) |
| A-270 | Cyclohexylmethyl | 3-[(Phenylmethyl)oxy]phenyl | W1a (m = 0) |
| A-271 | Cyclohexylmethyl | 3-Morpholin-4-ylphenyl | W1a (m = 0) |
| A-272 | Cyclohexylmethyl | 3-(Morpholin-4-ylmethyl)phenyl | W1a (m = 0) |
| A-273 | Cyclohexylmethyl | 3-Pyrrolidin-1-ylphenyl | W1a (m = 0) |
| A-274 | Cyclohexylmethyl | 4-Methylphenyl | W1a (m = 0) |
| A-275 | Cyclohexylmethyl | 4-(1-Methylethyl)phenyl | W1a (m = 0) |
| A-276 | Cyclohexylmethyl | 4-Methoxyphenyl | W1a (m = 0) |
| A-277 | Cyclohexylmethyl | 4-Chlorophenyl | W1a (m = 0) |
| A-278 | Cyclohexylmethyl | 4-Fluorophenyl | W1a (m = 0) |
| A-279 | Cyclohexylmethyl | 4-Trifluoromethylphenyl | W1a (m = 0) |
| A-280 | Cyclohexylmethyl | 4-Diethylaminophenyl | W1a (m = 0) |
| A-281 | Cyclohexylmethyl | 4-[(Diethylamino)methyl]phenyl | W1a (m = 0) |
| A-282 | Cyclohexylmethyl | 4-Cyanophenyl | W1a (m = 0) |
| A-283 | Cyclohexylmethyl | 4-(Piperidin-1-yl)phenyl | W1a (m = 0) |
| A-284 | Cyclohexylmethyl | 4-(4-Methylpiperazin-1-yl)phenyl | W1a (m = 0) |
| A-285 | Cyclohexylmethyl | 4-Pyrrolidin-1-ylphenyl | W1a (m = 0) |
| A-286 | Cyclohexylmethyl | 4-(1H-Imidazol-1-yl)phenyl | W1a (m = 0) |
| A-287 | Cyclohexylmethyl | 4-Morpholin-4-ylphenyl | W1a (m = 0) |
| A-288 | Cyclohexylmethyl | 4-(Morpholin-4-ylmethyl)phenyl | W1a (m = 0) |
| A-289 | Cyclohexylmethyl | 2,4-Difluorophenyl | W1a (m = 0) |
| A-290 | Cyclohexylmethyl | 2,6-Difluorophenyl | W1a (m = 0) |
| A-291 | Cyclohexylmethyl | 3,5-Difluorophenyl | W1a (m = 0) |
| A-292 | Cyclohexylmethyl | 2,4-Dichlorophenyl | W1a (m = 0) |
| A-293 | Cyclohexylmethyl | 2,6-Dichlorophenyl | W1a (m = 0) |
| A-294 | Cyclohexylmethyl | 3,5-Dichlorophenyl | W1a (m = 0) |
| A-295 | Cyclohexylmethyl | 2-Chloro-4-fluorophenyl | W1a (m = 0) |
| A-296 | Cyclohexylmethyl | 2-Chloro-4-morpholin-4-ylphenyl | W1a (m = 0) |
| A-297 | Cyclohexylmethyl | 2-Fluoro-4-morpholin-4-ylphenyl | W1a (m = 0) |
| A-298 | Cyclohexylmethyl | Pyridin-2-yl | W1a (m = 0) |
| A-299 | Cyclohexylmethyl | Pyridin-4-yl | W1a (m = 0) |
| A-300 | Cyclohexylmethyl | Thien-2-yl | W1a (m = 0) |
| A-301 | Cyclohexylmethyl | 2,3-Dihydrobenzo[b]furan-5-yl | W1a (m = 0) |
| A-302 | 2-Thienylmethyl | Phenyl | W1a (m = 0) |
| A-303 | 2-Thienylmethyl | 2-Methylphenyl | W1a (m = 0) |
| A-304 | 2-Thienylmethyl | 2-Methoxyphenyl | W1a (m = 0) |
| A-305 | 2-Thienylmethyl | 2-Chlorophenyl | W1a (m = 0) |
| A-306 | 2-Thienylmethyl | 2-Fluorophenyl | W1a (m = 0) |
| A-307 | 2-Thienylmethyl | 2-Trifluoromethylphenyl | W1a (m = 0) |
| A-308 | 2-Thienylmethyl | 3-Methylphenyl | W1a (m = 0) |
| A-309 | 2-Thienylmethyl | 3-Methoxyphenyl | W1a (m = 0) |
| A-310 | 2-Thienylmethyl | 3-Chlorophenyl | W1a (m = 0) |
| A-311 | 2-Thienylmethyl | 3-Fluorophenyl | W1a (m = 0) |
| A-312 | 2-Thienylmethyl | 3-Trifluoromethylphenyl | W1a (m = 0) |
| A-313 | 2-Thienylmethyl | 3-[(Phenylmethyl)oxy]phenyl | W1a (m = 0) |
| A-314 | 2-Thienylmethyl | 3-Morpholin-4-ylphenyl | W1a (m = 0) |
| A-315 | 2-Thienylmethyl | 3-(Morpholin-4-ylmethyl)phenyl | W1a (m = 0) |
| A-316 | 2-Thienylmethyl | 3-Pyrrolidin-1-ylphenyl | W1a (m = 0) |
| A-317 | 2-Thienylmethyl | 4-Methylphenyl | W1a (m = 0) |
| A-318 | 2-Thienylmethyl | 4-(1-Methylethyl)phenyl | W1a (m = 0) |
| A-319 | 2-Thienylmethyl | 4-Methoxyphenyl | W1a (m = 0) |
| A-320 | 2-Thienylmethyl | 4-Chlorophenyl | W1a (m = 0) |
| A-321 | 2-Thienylmethyl | 4-Fluorophenyl | W1a (m = 0) |
| A-322 | 2-Thienylmethyl | 4-Trifluoromethylphenyl | W1a (m = 0) |
| A-323 | 2-Thienylmethyl | 4-Diethylaminophenyl | W1a (m = 0) |
| A-324 | 2-Thienylmethyl | 4-[(Diethylamino)methyl]phenyl | W1a (m = 0) |
| A-325 | 2-Thienylmethyl | 4-Cyanophenyl | W1a (m = 0) |
| A-326 | 2-Thienylmethyl | 4-(Piperidin-1-yl)phenyl | W1a (m = 0) |
| A-327 | 2-Thienylmethyl | 4-(4-Methylpiperazin-1-yl)phenyl | W1a (m = 0) |
| A-328 | 2-Thienylmethyl | 4-Pyrrolidin-1-ylphenyl | W1a (m = 0) |
| A-329 | 2-Thienylmethyl | 4-(1H-Imidazol-1-yl)phenyl | W1a (m = 0) |
| A-330 | 2-Thienylmethyl | 4-Morpholin-4-ylphenyl | W1a (m = 0) |
| A-331 | 2-Thienylmethyl | 4-(Morpholin-4-ylmethyl)phenyl | W1a (m = 0) |
| A-332 | 2-Thienylmethyl | 2,4-Difluorophenyl | W1a (m = 0) |
| A-333 | 2-Thienylmethyl | 2,6-Difluorophenyl | W1a (m = 0) |
| A-334 | 2-Thienylmethyl | 3,5-Difluorophenyl | W1a (m = 0) |
| A-335 | 2-Thienylmethyl | 2,4-Dichlorophenyl | W1a (m = 0) |
| A-336 | 2-Thienylmethyl | 2,6-Dichlorophenyl | W1a (m = 0) |
| A-337 | 2-Thienylmethyl | 3,5-Dichlorophenyl | W1a (m = 0) |
| A-338 | 2-Thienylmethyl | 2-Chloro-4-fluorophenyl | W1a (m = 0) |
| A-339 | 2-Thienylmethyl | 2-Chloro-4-morpholin-4-ylphenyl | W1a (m = 0) |

TABLE A-continued

| No. | R¹ | R² | W |
|---|---|---|---|
| A-340 | 2-Thienylmethyl | 2-Fluoro-4-morpholin-4-ylphenyl | W1a (m = 0) |
| A-341 | 2-Thienylmethyl | Pyridin-2-yl | W1a (m = 0) |
| A-342 | 2-Thienylmethyl | Pyridin-4-yl | W1a (m = 0) |
| A-343 | 2-Thienylmethyl | Thien-2-yl | W1a (m = 0) |
| A-344 | 2-Thienylmethyl | 2,3-Dihydrobenzo[b]furan-5-yl | W1a (m = 0) |
| A-345 | Pyridin-3-ylmethyl | Phenyl | W1a (m = 0) |
| A-346 | Pyridin-3-ylmethyl | 2-Methylphenyl | W1a (m = 0) |
| A-347 | Pyridin-3-ylmethyl | 2-Methoxyphenyl | W1a (m = 0) |
| A-348 | Pyridin-3-ylmethyl | 2-Chlorophenyl | W1a (m = 0) |
| A-349 | Pyridin-3-ylmethyl | 2-Fluorophenyl | W1a (m = 0) |
| A-350 | Pyridin-3-ylmethyl | 2-Trifluoromethylphenyl | W1a (m = 0) |
| A-351 | Pyridin-3-ylmethyl | 3-Methylphenyl | W1a (m = 0) |
| A-352 | Pyridin-3-ylmethyl | 3-Methoxyphenyl | W1a (m = 0) |
| A-353 | Pyridin-3-ylmethyl | 3-Chlorophenyl | W1a (m = 0) |
| A-354 | Pyridin-3-ylmethyl | 3-Fluorophenyl | W1a (m = 0) |
| A-355 | Pyridin-3-ylmethyl | 3-Trifluoromethylphenyl | W1a (m = 0) |
| A-356 | Pyridin-3-ylmethyl | 3-[(Phenylmethyl)oxy]phenyl | W1a (m = 0) |
| A-357 | Pyridin-3-ylmethyl | 3-Morpholin-4-ylphenyl | W1a (m = 0) |
| A-358 | Pyridin-3-ylmethyl | 3-(Morpholin-4-ylmethyl)phenyl | W1a (m = 0) |
| A-359 | Pyridin-3-ylmethyl | 3-Pyrrolidin-1-ylphenyl | W1a (m = 0) |
| A-360 | Pyridin-3-ylmethyl | 4-Methylphenyl | W1a (m = 0) |
| A-361 | Pyridin-3-ylmethyl | 4-(1-Methylethyl)phenyl | W1a (m = 0) |
| A-362 | Pyridin-3-ylmethyl | 4-Methoxyphenyl | W1a (m = 0) |
| A-363 | Pyridin-3-ylmethyl | 4-Chlorophenyl | W1a (m = 0) |
| A-364 | Pyridin-3-ylmethyl | 4-Fluorophenyl | W1a (m = 0) |
| A-365 | Pyridin-3-ylmethyl | 4-Trifluoromethylphenyl | W1a (m = 0) |
| A-366 | Pyridin-3-ylmethyl | 4-Diethylaminophenyl | W1a (m = 0) |
| A-367 | Pyridin-3-ylmethyl | 4-[(Diethylamino)methyl]phenyl | W1a (m = 0) |
| A-368 | Pyridin-3-ylmethyl | 4-Cyanophenyl | W1a (m = 0) |
| A-369 | Pyridin-3-ylmethyl | 4-(Piperidin-1-yl)phenyl | W1a (m = 0) |
| A-370 | Pyridin-3-ylmethyl | 4-(4-Methylpiperazin-1-yl)phenyl | W1a (m = 0) |
| A-371 | Pyridin-3-ylmethyl | 4-Pyrrolidin-1-ylphenyl | W1a (m = 0) |
| A-372 | Pyridin-3-ylmethyl | 4-(1H-Imidazol-1-yl)phenyl | W1a (m = 0) |
| A-373 | Pyridin-3-ylmethyl | 4-Morpholin-4-ylphenyl | W1a (m = 0) |
| A-374 | Pyridin-3-ylmethyl | 4-(Morpholin-4-ylmethyl)phenyl | W1a (m = 0) |
| A-375 | Pyridin-3-ylmethyl | 2,4-Difluorophenyl | W1a (m = 0) |
| A-376 | Pyridin-3-ylmethyl | 2,6-Difluorophenyl | W1a (m = 0) |
| A-377 | Pyridin-3-ylmethyl | 3,5-Difluorophenyl | W1a (m = 0) |
| A-378 | Pyridin-3-ylmethyl | 2,4-Dichlorophenyl | W1a (m = 0) |
| A-379 | Pyridin-3-ylmethyl | 2,6-Dichlorophenyl | W1a (m = 0) |
| A-380 | Pyridin-3-ylmethyl | 3,5-Dichlorophenyl | W1a (m = 0) |
| A-381 | Pyridin-3-ylmethyl | 2-Chloro-4-fluorophenyl | W1a (m = 0) |
| A-382 | Pyridin-3-ylmethyl | 2-Chloro-4-morpholin-4-ylphenyl | W1a (m = 0) |
| A-383 | Pyridin-3-ylmethyl | 2-Fluoro-4-morpholin-4-ylphenyl | W1a (m = 0) |
| A-384 | Pyridin-3-ylmethyl | Pyridin-2-yl | W1a (m = 0) |
| A-385 | Pyridin-3-ylmethyl | Pyridin-4-yl | W1a (m = 0) |
| A-386 | Pyridin-3-ylmethyl | Thien-2-yl | W1a (m = 0) |
| A-387 | Pyridin-3-ylmethyl | 2,3-Dihydrobenzo[b]furan-5-yl | W1a (m = 0) |
| A-388 | n-Butyl | Phenyl | W1b (m = 0) |
| A-389 | n-Butyl | 2-Methylphenyl | W1b (m = 0) |
| A-390 | n-Butyl | 2-Methoxyphenyl | W1b (m = 0) |
| A-391 | n-Butyl | 2-Chlorophenyl | W1b (m = 0) |
| A-392 | n-Butyl | 2-Fluorophenyl | W1b (m = 0) |
| A-393 | n-Butyl | 2-Trifluoromethylphenyl | W1b (m = 0) |
| A-394 | n-Butyl | 3-Methylphenyl | W1b (m = 0) |
| A-395 | n-Butyl | 3-Methoxyphenyl | W1b (m = 0) |
| A-396 | n-Butyl | 3-Chlorophenyl | W1b (m = 0) |
| A-397 | n-Butyl | 3-Fluorophenyl | W1b (m = 0) |
| A-398 | n-Butyl | 3-Trifluoromethylphenyl | W1b (m = 0) |
| A-399 | n-Butyl | 3-[(Phenylmethyl)oxy]phenyl | W1b (m = 0) |
| A-400 | n-Butyl | 3-Morpholin-4-ylphenyl | W1b (m = 0) |
| A-401 | n-Butyl | 3-(Morpholin-4-ylmethyl)phenyl | W1b (m = 0) |
| A-402 | n-Butyl | 3-Pyrrolidin-1-ylphenyl | W1b (m = 0) |
| A-403 | n-Butyl | 4-Methylphenyl | W1b (m = 0) |
| A-404 | n-Butyl | 4-(1-Methylethyl)phenyl | W1b (m = 0) |
| A-405 | n-Butyl | 4-Methoxyphenyl | W1b (m = 0) |
| A-406 | n-Butyl | 4-Chlorophenyl | W1b (m = 0) |
| A-407 | n-Butyl | 4-Fluorophenyl | W1b (m = 0) |
| A-408 | n-Butyl | 4-Trifluoromethylphenyl | W1b (m = 0) |
| A-409 | n-Butyl | 4-Diethylaminophenyl | W1b (m = 0) |
| A-410 | n-Butyl | 4-[(Diethylamino)methyl]phenyl | W1b (m = 0) |
| A-411 | n-Butyl | 4-Cyanophenyl | W1b (m = 0) |
| A-412 | n-Butyl | 4-(Piperidin-1-yl)phenyl | W1b (m = 0) |
| A-413 | n-Butyl | 4-(4-Methylpiperazin-1-yl)phenyl | W1b (m = 0) |
| A-414 | n-Butyl | 4-Pyrrolidin-1-ylphenyl | W1b (m = 0) |
| A-415 | n-Butyl | 4-(1H-Imidazol-1-yl)phenyl | W1b (m = 0) |
| A-416 | n-Butyl | 4-Morpholin-4-ylphenyl | W1b (m = 0) |
| A-417 | n-Butyl | 4-(Morpholin-4-ylmethyl)phenyl | W1b (m = 0) |

TABLE A-continued

| No. | R¹ | R² | W |
|---|---|---|---|
| A-418 | n-Butyl | 2,4-Difluorophenyl | W1b (m = 0) |
| A-419 | n-Butyl | 2,6-Difluorophenyl | W1b (m = 0) |
| A-420 | n-Butyl | 3,5-Difluorophenyl | W1b (m = 0) |
| A-421 | n-Butyl | 2,4-Dichlorophenyl | W1b (m = 0) |
| A-422 | n-Butyl | 2,6-Dichlorophenyl | W1b (m = 0) |
| A-423 | n-Butyl | 3,5-Dichlorophenyl | W1b (m = 0) |
| A-424 | n-Butyl | 2-Chloro-4-fluorophenyl | W1b (m = 0) |
| A-425 | n-Butyl | 2-Chloro-4-morpholin-4-ylphenyl | W1b (m = 0) |
| A-426 | n-Butyl | 2-Fluoro-4-morpholin-4-ylphenyl | W1b (m = 0) |
| A-427 | n-Butyl | Pyridin-2-yl | W1b (m = 0) |
| A-428 | n-Butyl | Pyridin-4-yl | W1b (m = 0) |
| A-429 | n-Butyl | Thien-2-yl | W1b (m = 0) |
| A-430 | n-Butyl | 2,3-Dihydrobenzo[b]furan-5-yl | W1b (m = 0) |
| A-431 | Isobutyl | Phenyl | W1b (m = 0) |
| A-432 | Isobutyl | 2-Methylphenyl | W1b (m = 0) |
| A-433 | Isobutyl | 2-Methoxyphenyl | W1b (m = 0) |
| A-434 | Isobutyl | 2-Chlorophenyl | W1b (m = 0) |
| A-435 | Isobutyl | 2-Fluorophenyl | W1b (m = 0) |
| A-436 | Isobutyl | 2-Trifluoromethylphenyl | W1b (m = 0) |
| A-437 | Isobutyl | 3-Methylphenyl | W1b (m = 0) |
| A-438 | Isobutyl | 3-Methoxyphenyl | W1b (m = 0) |
| A-439 | Isobutyl | 3-Chlorophenyl | W1b (m = 0) |
| A-440 | Isobutyl | 3-Fluorophenyl | W1b (m = 0) |
| A-441 | Isobutyl | 3-Trifluoromethylphenyl | W1b (m = 0) |
| A-442 | Isobutyl | 3-[(Phenylmethyl)oxy]phenyl | W1b (m = 0) |
| A-443 | Isobutyl | 3-Morpholin-4-ylphenyl | W1b (m = 0) |
| A-444 | Isobutyl | 3-(Morpholin-4-ylmethyl)phenyl | W1b (m = 0) |
| A-445 | Isobutyl | 3-Pyrrolidin-1-ylphenyl | W1b (m = 0) |
| A-446 | Isobutyl | 4-Methylphenyl | W1b (m = 0) |
| A-447 | Isobutyl | 4-(1-Methylethyl)phenyl | W1b (m = 0) |
| A-448 | Isobutyl | 4-Methoxyphenyl | W1b (m = 0) |
| A-449 | Isobutyl | 4-Chlorophenyl | W1b (m = 0) |
| A-450 | Isobutyl | 4-Fluorophenyl | W1b (m = 0) |
| A-451 | Isobutyl | 4-Trifluoromethylphenyl | W1b (m = 0) |
| A-452 | Isobutyl | 4-Diethylaminophenyl | W1b (m = 0) |
| A-453 | Isobutyl | 4-[(Diethylamino)methyl]phenyl | W1b (m = 0) |
| A-454 | Isobutyl | 4-Cyanophenyl | W1b (m = 0) |
| A-455 | Isobutyl | 4-(Piperidin-1-yl)phenyl | W1b (m = 0) |
| A-456 | Isobutyl | 4-(4-Methylpiperazin-1-yl)phenyl | W1b (m = 0) |
| A-457 | Isobutyl | 4-Pyrrolidin-1-ylphenyl | W1b (m = 0) |
| A-458 | Isobutyl | 4-(1H-Imidazol-1-yl)phenyl | W1b (m = 0) |
| A-459 | Isobutyl | 4-Morpholin-4-ylphenyl | W1b (m = 0) |
| A-460 | Isobutyl | 4-(Morpholin-4-ylmethyl)phenyl | W1b (m = 0) |
| A-461 | Isobutyl | 2,4-Difluorophenyl | W1b (m = 0) |
| A-462 | Isobutyl | 2,6-Difluorophenyl | W1b (m = 0) |
| A-463 | Isobutyl | 3,5-Difluorophenyl | W1b (m = 0) |
| A-464 | Isobutyl | 2,4-Dichlorophenyl | W1b (m = 0) |
| A-465 | Isobutyl | 2,6-Dichlorophenyl | W1b (m = 0) |
| A-466 | Isobutyl | 3,5-Dichlorophenyl | W1b (m = 0) |
| A-467 | Isobutyl | 2-Chloro-4-fluorophenyl | W1b (m = 0) |
| A-468 | Isobutyl | 2-Chloro-4-morpholin-4-ylphenyl | W1b (m = 0) |
| A-469 | Isobutyl | 2-Fluoro-4-morpholin-4-ylphenyl | W1b (m = 0) |
| A-470 | Isobutyl | Pyridin-2-yl | W1b (m = 0) |
| A-471 | Isobutyl | Pyridin-4-yl | W1b (m = 0) |
| A-472 | Isobutyl | Thien-2-yl | W1b (m = 0) |
| A-473 | Isobutyl | 2,3-Dihydrobenzo[b]furan-5-yl | W1b (m = 0) |
| A-474 | Benzyl | Phenyl | W1b (m = 0) |
| A-475 | Benzyl | 2-Methylphenyl | W1b (m = 0) |
| A-476 | Benzyl | 2-Methoxyphenyl | W1b (m = 0) |
| A-477 | Benzyl | 2-Chlorophenyl | W1b (m = 0) |
| A-478 | Benzyl | 2-Fluorophenyl | W1b (m = 0) |
| A-479 | Benzyl | 2-Trifluoromethylphenyl | W1b (m = 0) |
| A-480 | Benzyl | 3-Methylphenyl | W1b (m = 0) |
| A-481 | Benzyl | 3-Methoxyphenyl | W1b (m = 0) |
| A-482 | Benzyl | 3-Chlorophenyl | W1b (m = 0) |
| A-483 | Benzyl | 3-Fluorophenyl | W1b (m = 0) |
| A-484 | Benzyl | 3-Trifluoromethylphenyl | W1b (m = 0) |
| A-485 | Benzyl | 3-[(Phenylmethyl)oxy]phenyl | W1b (m = 0) |
| A-486 | Benzyl | 3-Morpholin-4-ylphenyl | W1b (m = 0) |
| A-487 | Benzyl | 3-(Morpholin-4-ylmethyl)phenyl | W1b (m = 0) |
| A-488 | Benzyl | 3-Pyrrolidin-1-ylphenyl | W1b (m = 0) |
| A-489 | Benzyl | 4-Methylphenyl | W1b (m = 0) |
| A-490 | Benzyl | 4-(1-Methylethyl)phenyl | W1b (m = 0) |
| A-491 | Benzyl | 4-Methoxyphenyl | W1b (m = 0) |
| A-492 | Benzyl | 4-Chlorophenyl | W1b (m = 0) |
| A-493 | Benzyl | 4-Fluorophenyl | W1b (m = 0) |
| A-494 | Benzyl | 4-Trifluoromethylphenyl | W1b (m = 0) |
| A-495 | Benzyl | 4-Diethylaminophenyl | W1b (m = 0) |

TABLE A-continued

| No. | R¹ | R² | W |
|---|---|---|---|
| A-496 | Benzyl | 4-[(Diethylamino)methyl]phenyl | W1b (m = 0) |
| A-497 | Benzyl | 4-Cyanophenyl | W1b (m = 0) |
| A-498 | Benzyl | 4-(Piperidin-1-yl)phenyl | W1b (m = 0) |
| A-499 | Benzyl | 4-(4-Methylpiperazin-1-yl)phenyl | W1b (m = 0) |
| A-500 | Benzyl | 4-Pyrrolidin-1-ylphenyl | W1b (m = 0) |
| A-501 | Benzyl | 4-(1H-Imidazol-1-yl)phenyl | W1b (m = 0) |
| A-502 | Benzyl | 4-Morpholin-4-ylphenyl | W1b (m = 0) |
| A-503 | Benzyl | 4-(Morpholin-4-ylmethyl)phenyl | W1b (m = 0) |
| A-504 | Benzyl | 2,4-Difluorophenyl | W1b (m = 0) |
| A-505 | Benzyl | 2,6-Difluorophenyl | W1b (m = 0) |
| A-506 | Benzyl | 3,5-Difluorophenyl | W1b (m = 0) |
| A-507 | Benzyl | 2,4-Dichlorophenyl | W1b (m = 0) |
| A-508 | Benzyl | 2,6-Dichlorophenyl | W1b (m = 0) |
| A-509 | Benzyl | 3,5-Dichlorophenyl | W1b (m = 0) |
| A-510 | Benzyl | 2-Chloro-4-fluorophenyl | W1b (m = 0) |
| A-511 | Benzyl | 2-Chloro-4-morpholin-4-ylphenyl | W1b (m = 0) |
| A-512 | Benzyl | 2-Fluoro-4-morpholin-4-ylphenyl | W1b (m = 0) |
| A-513 | Benzyl | Pyridin-2-yl | W1b (m = 0) |
| A-514 | Benzyl | Pyridin-4-yl | W1b (m = 0) |
| A-515 | Benzyl | Thien-2-yl | W1b (m = 0) |
| A-516 | Benzyl | 2,3-Dihydrobenzo[b]furan-5-yl | W1b (m = 0) |
| A-517 | 4-Chlorobenzyl | Phenyl | W1b (m = 0) |
| A-518 | 4-Chlorobenzyl | 2-Methylphenyl | W1b (m = 0) |
| A-519 | 4-Chlorobenzyl | 2-Methoxyphenyl | W1b (m = 0) |
| A-520 | 4-Chlorobenzyl | 2-Chlorophenyl | W1b (m = 0) |
| A-521 | 4-Chlorobenzyl | 2-Fluorophenyl | W1b (m = 0) |
| A-522 | 4-Chlorobenzyl | 2-Trifluoromethylphenyl | W1b (m = 0) |
| A-523 | 4-Chlorobenzyl | 3-Methylphenyl | W1b (m = 0) |
| A-524 | 4-Chlorobenzyl | 3-Methoxyphenyl | W1b (m = 0) |
| A-525 | 4-Chlorobenzyl | 3-Chlorophenyl | W1b (m = 0) |
| A-526 | 4-Chlorobenzyl | 3-Fluorophenyl | W1b (m = 0) |
| A-527 | 4-Chlorobenzyl | 3-Trifluoromethylphenyl | W1b (m = 0) |
| A-528 | 4-Chlorobenzyl | 3-[(Phenylmethyl)oxy]phenyl | W1b (m = 0) |
| A-529 | 4-Chlorobenzyl | 3-Morpholin-4-ylphenyl | W1b (m = 0) |
| A-530 | 4-Chlorobenzyl | 3-(Morpholin-4-ylmethyl)phenyl | W1b (m = 0) |
| A-531 | 4-Chlorobenzyl | 3-Pyrrolidin-1-ylphenyl | W1b (m = 0) |
| A-532 | 4-Chlorobenzyl | 4-Methylphenyl | W1b (m = 0) |
| A-533 | 4-Chlorobenzyl | 4-(1-Methylethyl)phenyl | W1b (m = 0) |
| A-534 | 4-Chlorobenzyl | 4-Methoxyphenyl | W1b (m = 0) |
| A-535 | 4-Chlorobenzyl | 4-Chlorophenyl | W1b (m = 0) |
| A-536 | 4-Chlorobenzyl | 4-Fluorophenyl | W1b (m = 0) |
| A-537 | 4-Chlorobenzyl | 4-Trifluoromethylphenyl | W1b (m = 0) |
| A-538 | 4-Chlorobenzyl | 4-Diethylaminophenyl | W1b (m = 0) |
| A-539 | 4-Chlorobenzyl | 4-[(Diethylamino)methyl]phenyl | W1b (m = 0) |
| A-540 | 4-Chlorobenzyl | 4-Cyanophenyl | W1b (m = 0) |
| A-541 | 4-Chlorobenzyl | 4-(Piperidin-1-yl)phenyl | W1b (m = 0) |
| A-542 | 4-Chlorobenzyl | 4-(4-Methylpiperazin-1-yl)phenyl | W1b (m = 0) |
| A-543 | 4-Chlorobenzyl | 4-Pyrrolidin-1-ylphenyl | W1b (m = 0) |
| A-544 | 4-Chlorobenzyl | 4-(1H-Imidazol-1-yl)phenyl | W1b (m = 0) |
| A-545 | 4-Chlorobenzyl | 4-Morpholin-4-ylphenyl | W1b (m = 0) |
| A-546 | 4-Chlorobenzyl | 4-(Morpholin-4-ylmethyl)phenyl | W1b (m = 0) |
| A-547 | 4-Chlorobenzyl | 2,4-Difluorophenyl | W1b (m = 0) |
| A-548 | 4-Chlorobenzyl | 2,6-Difluorophenyl | W1b (m = 0) |
| A-549 | 4-Chlorobenzyl | 3,5-Difluorophenyl | W1b (m = 0) |
| A-550 | 4-Chlorobenzyl | 2,4-Dichlorophenyl | W1b (m = 0) |
| A-551 | 4-Chlorobenzyl | 2,6-Dichlorophenyl | W1b (m = 0) |
| A-552 | 4-Chlorobenzyl | 3,5-Dichlorophenyl | W1b (m = 0) |
| A-553 | 4-Chlorobenzyl | 2-Chloro-4-fluorophenyl | W1b (m = 0) |
| A-554 | 4-Chlorobenzyl | 2-Chloro-4-morpholin-4-ylphenyl | W1b (m = 0) |
| A-555 | 4-Chlorobenzyl | 2-Fluoro-4-morpholin-4-ylphenyl | W1b (m = 0) |
| A-556 | 4-Chlorobenzyl | Pyridin-2-yl | W1b (m = 0) |
| A-557 | 4-Chlorobenzyl | Pyridin-4-yl | W1b (m = 0) |
| A-558 | 4-Chlorobenzyl | Thien-2-yl | W1b (m = 0) |
| A-559 | 4-Chlorobenzyl | 2,3-Dihydrobenzo[b]furan-5-yl | W1b (m = 0) |
| A-560 | 4-Methoxybenzyl | Phenyl | W1b (m = 0) |
| A-561 | 4-Methoxybenzyl | 2-Methylphenyl | W1b (m = 0) |
| A-562 | 4-Methoxybenzyl | 2-Methoxyphenyl | W1b (m = 0) |
| A-563 | 4-Methoxybenzyl | 2-Chlorophenyl | W1b (m = 0) |
| A-564 | 4-Methoxybenzyl | 2-Fluorophenyl | W1b (m = 0) |
| A-565 | 4-Methoxybenzyl | 2-Trifluoromethylphenyl | W1b (m = 0) |
| A-566 | 4-Methoxybenzyl | 3-Methylphenyl | W1b (m = 0) |
| A-567 | 4-Methoxybenzyl | 3-Methoxyphenyl | W1b (m = 0) |
| A-568 | 4-Methoxybenzyl | 3-Chlorophenyl | W1b (m = 0) |
| A-569 | 4-Methoxybenzyl | 3-Fluorophenyl | W1b (m = 0) |
| A-570 | 4-Methoxybenzyl | 3-Trifluoromethylphenyl | W1b (m = 0) |
| A-571 | 4-Methoxybenzyl | 3-[(Phenylmethyl)oxy]phenyl | W1b (m = 0) |
| A-572 | 4-Methoxybenzyl | 3-Morpholin-4-ylphenyl | W1b (m = 0) |
| A-573 | 4-Methoxybenzyl | 3-(Morpholin-4-ylmethyl)phenyl | W1b (m = 0) |

TABLE A-continued

| No. | R¹ | R² | W |
|---|---|---|---|
| A-574 | 4-Methoxybenzyl | 3-Pyrrolidin-1-ylphenyl | W1b (m = 0) |
| A-575 | 4-Methoxybenzyl | 4-Methylphenyl | W1b (m = 0) |
| A-576 | 4-Methoxybenzyl | 4-(1-Methylethyl)phenyl | W1b (m = 0) |
| A-577 | 4-Methoxybenzyl | 4-Methoxyphenyl | W1b (m = 0) |
| A-578 | 4-Methoxybenzyl | 4-Chlorophenyl | W1b (m = 0) |
| A-579 | 4-Methoxybenzyl | 4-Fluorophenyl | W1b (m = 0) |
| A-580 | 4-Methoxybenzyl | 4-Trifluoromethylphenyl | W1b (m = 0) |
| A-581 | 4-Methoxybenzyl | 4-Diethylaminophenyl | W1b (m = 0) |
| A-582 | 4-Methoxybenzyl | 4-[(Diethylamino)methyl]phenyl | W1b (m = 0) |
| A-583 | 4-Methoxybenzyl | 4-Cyanophenyl | W1b (m = 0) |
| A-584 | 4-Methoxybenzyl | 4-(Piperidin-1-yl)phenyl | W1b (m = 0) |
| A-585 | 4-Methoxybenzyl | 4-(4-Methylpiperazin-1-yl)phenyl | W1b (m = 0) |
| A-586 | 4-Methoxybenzyl | 4-Pyrrolidin-1-ylphenyl | W1b (m = 0) |
| A-587 | 4-Methoxybenzyl | 4-(1H-Imidazol-1-yl)phenyl | W1b (m = 0) |
| A-588 | 4-Methoxybenzyl | 4-Morpholin-4-ylphenyl | W1b (m = 0) |
| A-589 | 4-Methoxybenzyl | 4-(Morpholin-4-ylmethyl)phenyl | W1b (m = 0) |
| A-590 | 4-Methoxybenzyl | 2,4-Difluorophenyl | W1b (m = 0) |
| A-591 | 4-Methoxybenzyl | 2,6-Difluorophenyl | W1b (m = 0) |
| A-592 | 4-Methoxybenzyl | 3,5-Difluorophenyl | W1b (m = 0) |
| A-593 | 4-Methoxybenzyl | 2,4-Dichlorophenyl | W1b (m = 0) |
| A-594 | 4-Methoxybenzyl | 2,6-Dichlorophenyl | W1b (m = 0) |
| A-595 | 4-Methoxybenzyl | 3,5-Dichlorophenyl | W1b (m = 0) |
| A-596 | 4-Methoxybenzyl | 2-Chloro-4-fluorophenyl | W1b (m = 0) |
| A-597 | 4-Methoxybenzyl | 2-Chloro-4-morpholin-4-ylphenyl | W1b (m = 0) |
| A-598 | 4-Methoxybenzyl | 2-Fluoro-4-morpholin-4-ylphenyl | W1b (m = 0) |
| A-599 | 4-Methoxybenzyl | Pyridin-2-yl | W1b (m = 0) |
| A-600 | 4-Methoxybenzyl | Pyridin-4-yl | W1b (m = 0) |
| A-601 | 4-Methoxybenzyl | Thien-2-yl | W1b (m = 0) |
| A-602 | 4-Methoxybenzyl | 2,3-Dihydrobenzo[b]furan-5-yl | W1b (m = 0) |
| A-603 | Cyclohexylmethyl | Phenyl | W1b (m = 0) |
| A-604 | Cyclohexylmethyl | 2-Methylphenyl | W1b (m = 0) |
| A-605 | Cyclohexylmethyl | 2-Methoxyphenyl | W1b (m = 0) |
| A-606 | Cyclohexylmethyl | 2-Chlorophenyl | W1b (m = 0) |
| A-607 | Cyclohexylmethyl | 2-Fluorophenyl | W1b (m = 0) |
| A-608 | Cyclohexylmethyl | 2-Trifluoromethylphenyl | W1b (m = 0) |
| A-609 | Cyclohexylmethyl | 3-Methylphenyl | W1b (m = 0) |
| A-610 | Cyclohexylmethyl | 3-Methoxyphenyl | W1b (m = 0) |
| A-611 | Cyclohexylmethyl | 3-Chlorophenyl | W1b (m = 0) |
| A-612 | Cyclohexylmethyl | 3-Fluorophenyl | W1b (m = 0) |
| A-613 | Cyclohexylmethyl | 3-Trifluoromethylphenyl | W1b (m = 0) |
| A-614 | Cyclohexylmethyl | 3-[(Phenylmethyl)oxy]phenyl | W1b (m = 0) |
| A-615 | Cyclohexylmethyl | 3-Morpholin-4-ylphenyl | W1b (m = 0) |
| A-616 | Cyclohexylmethyl | 3-(Morpholin-4-ylmethyl)phenyl | W1b (m = 0) |
| A-617 | Cyclohexylmethyl | 3-Pyrrolidin-1-ylphenyl | W1b (m = 0) |
| A-618 | Cyclohexylmethyl | 4-Methylphenyl | W1b (m = 0) |
| A-619 | Cyclohexylmethyl | 4-(1-Methylethyl)phenyl | W1b (m = 0) |
| A-620 | Cyclohexylmethyl | 4-Methoxyphenyl | W1b (m = 0) |
| A-621 | Cyclohexylmethyl | 4-Chlorophenyl | W1b (m = 0) |
| A-622 | Cyclohexylmethyl | 4-Fluorophenyl | W1b (m = 0) |
| A-623 | Cyclohexylmethyl | 4-Trifluoromethylphenyl | W1b (m = 0) |
| A-624 | Cyclohexylmethyl | 4-Diethylaminophenyl | W1b (m = 0) |
| A-625 | Cyclohexylmethyl | 4-[(Diethylamino)methyl]phenyl | W1b (m = 0) |
| A-626 | Cyclohexylmethyl | 4-Cyanophenyl | W1b (m = 0) |
| A-627 | Cyclohexylmethyl | 4-(Piperidin-1-yl)phenyl | W1b (m = 0) |
| A-628 | Cyclohexylmethyl | 4-(4-Methylpiperazin-1-yl)phenyl | W1b (m = 0) |
| A-629 | Cyclohexylmethyl | 4-Pyrrolidin-1-ylphenyl | W1b (m = 0) |
| A-630 | Cyclohexylmethyl | 4-(1H-Imidazol-1-yl)phenyl | W1b (m = 0) |
| A-631 | Cyclohexylmethyl | 4-Morpholin-4-ylphenyl | W1b (m = 0) |
| A-632 | Cyclohexylmethyl | 4-(Morpholin-4-ylmethyl)phenyl | W1b (m = 0) |
| A-633 | Cyclohexylmethyl | 2,4-Difluorophenyl | W1b (m = 0) |
| A-634 | Cyclohexylmethyl | 2,6-Difluorophenyl | W1b (m = 0) |
| A-635 | Cyclohexylmethyl | 3,5-Difluorophenyl | W1b (m = 0) |
| A-636 | Cyclohexylmethyl | 2,4-Dichlorophenyl | W1b (m = 0) |
| A-637 | Cyclohexylmethyl | 2,6-Dichlorophenyl | W1b (m = 0) |
| A-638 | Cyclohexylmethyl | 3,5-Dichlorophenyl | W1b (m = 0) |
| A-639 | Cyclohexylmethyl | 2-Chloro-4-fluorophenyl | W1b (m = 0) |
| A-640 | Cyclohexylmethyl | 2-Chloro-4-morpholin-4-ylphenyl | W1b (m = 0) |
| A-641 | Cyclohexylmethyl | 2-Fluoro-4-morpholin-4-ylphenyl | W1b (m = 0) |
| A-642 | Cyclohexylmethyl | Pyridin-2-yl | W1b (m = 0) |
| A-643 | Cyclohexylmethyl | Pyridin-4-yl | W1b (m = 0) |
| A-644 | Cyclohexylmethyl | Thien-2-yl | W1b (m = 0) |
| A-645 | Cyclohexylmethyl | 2,3-Dihydrobenzo[b]furan-5-yl | W1b (m = 0) |
| A-646 | 2-Thienylmethyl | Phenyl | W1b (m = 0) |
| A-647 | 2-Thienylmethyl | 2-Methylphenyl | W1b (m = 0) |
| A-648 | 2-Thienylmethyl | 2-Methoxyphenyl | W1b (m = 0) |
| A-649 | 2-Thienylmethyl | 2-Chlorophenyl | W1b (m = 0) |
| A-650 | 2-Thienylmethyl | 2-Fluorophenyl | W1b (m = 0) |
| A-651 | 2-Thienylmethyl | 2-Trifluoromethylphenyl | W1b (m = 0) |

TABLE A-continued

| No. | R¹ | R² | W |
|---|---|---|---|
| A-652 | 2-Thienylmethyl | 3-Methylphenyl | W1b (m = 0) |
| A-653 | 2-Thienylmethyl | 3-Methoxyphenyl | W1b (m = 0) |
| A-654 | 2-Thienylmethyl | 3-Chlorophenyl | W1b (m = 0) |
| A-655 | 2-Thienylmethyl | 3-Fluorophenyl | W1b (m = 0) |
| A-656 | 2-Thienylmethyl | 3-Trifluoromethylphenyl | W1b (m = 0) |
| A-657 | 2-Thienylmethyl | 3-[(Phenylmethyl)oxy]phenyl | W1b (m = 0) |
| A-658 | 2-Thienylmethyl | 3-Morpholin-4-ylphenyl | W1b (m = 0) |
| A-659 | 2-Thienylmethyl | 3-(Morpholin-4-ylmethyl)phenyl | W1b (m = 0) |
| A-660 | 2-Thienylmethyl | 3-Pyrrolidin-1-ylphenyl | W1b (m = 0) |
| A-661 | 2-Thienylmethyl | 4-Methylphenyl | W1b (m = 0) |
| A-662 | 2-Thienylmethyl | 4-(1-Methylethyl)phenyl | W1b (m = 0) |
| A-663 | 2-Thienylmethyl | 4-Methoxyphenyl | W1b (m = 0) |
| A-664 | 2-Thienylmethyl | 4-Chlorophenyl | W1b (m = 0) |
| A-665 | 2-Thienylmethyl | 4-Fluorophenyl | W1b (m = 0) |
| A-666 | 2-Thienylmethyl | 4-Trifluoromethylphenyl | W1b (m = 0) |
| A-667 | 2-Thienylmethyl | 4-Diethylaminophenyl | W1b (m = 0) |
| A-668 | 2-Thienylmethyl | 4-[(Diethylamino)methyl]phenyl | W1b (m = 0) |
| A-669 | 2-Thienylmethyl | 4-Cyanophenyl | W1b (m = 0) |
| A-670 | 2-Thienylmethyl | 4-(Piperidin-1-yl)phenyl | W1b (m = 0) |
| A-671 | 2-Thienylmethyl | 4-(4-Methylpiperazin-1-yl)phenyl | W1b (m = 0) |
| A-672 | 2-Thienylmethyl | 4-Pyrrolidin-1-ylphenyl | W1b (m = 0) |
| A-673 | 2-Thienylmethyl | 4-(1H-Imidazol-1-yl)phenyl | W1b (m = 0) |
| A-674 | 2-Thienylmethyl | 4-Morpholin-4-ylphenyl | W1b (m = 0) |
| A-675 | 2-Thienylmethyl | 4-(Morpholin-4-ylmethyl)phenyl | W1b (m = 0) |
| A-676 | 2-Thienylmethyl | 2,4-Difluorophenyl | W1b (m = 0) |
| A-677 | 2-Thienylmethyl | 2,6-Difluorophenyl | W1b (m = 0) |
| A-678 | 2-Thienylmethyl | 3,5-Difluorophenyl | W1b (m = 0) |
| A-679 | 2-Thienylmethyl | 2,4-Dichlorophenyl | W1b (m = 0) |
| A-680 | 2-Thienylmethyl | 2,6-Dichlorophenyl | W1b (m = 0) |
| A-681 | 2-Thienylmethyl | 3,5-Dichlorophenyl | W1b (m = 0) |
| A-682 | 2-Thienylmethyl | 2-Chloro-4-fluorophenyl | W1b (m = 0) |
| A-683 | 2-Thienylmethyl | 2-Chloro-4-morpholin-4-ylphenyl | W1b (m = 0) |
| A-684 | 2-Thienylmethyl | 2-Fluoro-4-morpholin-4-ylphenyl | W1b (m = 0) |
| A-685 | 2-Thienylmethyl | Pyridin-2-yl | W1b (m = 0) |
| A-686 | 2-Thienylmethyl | Pyridin-4-yl | W1b (m = 0) |
| A-687 | 2-Thienylmethyl | Thien-2-yl | W1b (m = 0) |
| A-688 | 2-Thienylmethyl | 2,3-Dihydrobenzo[b]furan-5-yl | W1b (m = 0) |
| A-689 | Pyridin-3-ylmethyl | Phenyl | W1b (m = 0) |
| A-690 | Pyridin-3-ylmethyl | 2-Methylphenyl | W1b (m = 0) |
| A-691 | Pyridin-3-ylmethyl | 2-Methoxyphenyl | W1b (m = 0) |
| A-692 | Pyridin-3-ylmethyl | 2-Chlorophenyl | W1b (m = 0) |
| A-693 | Pyridin-3-ylmethyl | 2-Fluorophenyl | W1b (m = 0) |
| A-694 | Pyridin-3-ylmethyl | 2-Trifluoromethylphenyl | W1b (m = 0) |
| A-695 | Pyridin-3-ylmethyl | 3-Methylphenyl | W1b (m = 0) |
| A-696 | Pyridin-3-ylmethyl | 3-Methoxyphenyl | W1b (m = 0) |
| A-697 | Pyridin-3-ylmethyl | 3-Chlorophenyl | W1b (m = 0) |
| A-698 | Pyridin-3-ylmethyl | 3-Fluorophenyl | W1b (m = 0) |
| A-699 | Pyridin-3-ylmethyl | 3-Trifluoromethylphenyl | W1b (m = 0) |
| A-700 | Pyridin-3-ylmethyl | 3-[(Phenylmethyl)oxy]phenyl | W1b (m = 0) |
| A-701 | Pyridin-3-ylmethyl | 3-Morpholin-4-ylphenyl | W1b (m = 0) |
| A-702 | Pyridin-3-ylmethyl | 3-(Morpholin-4-ylmethyl)phenyl | W1b (m = 0) |
| A-703 | Pyridin-3-ylmethyl | 3-Pyrrolidin-1-ylphenyl | W1b (m = 0) |
| A-704 | Pyridin-3-ylmethyl | 4-Methylphenyl | W1b (m = 0) |
| A-705 | Pyridin-3-ylmethyl | 4-(1-Methylethyl)phenyl | W1b (m = 0) |
| A-706 | Pyridin-3-ylmethyl | 4-Methoxyphenyl | W1b (m = 0) |
| A-707 | Pyridin-3-ylmethyl | 4-Chlorophenyl | W1b (m = 0) |
| A-708 | Pyridin-3-ylmethyl | 4-Fluorophenyl | W1b (m = 0) |
| A-709 | Pyridin-3-ylmethyl | 4-Trifluoromethylphenyl | W1b (m = 0) |
| A-710 | Pyridin-3-ylmethyl | 4-Diethylaminophenyl | W1b (m = 0) |
| A-711 | Pyridin-3-ylmethyl | 4-[(Diethylamino)methyl]phenyl | W1b (m = 0) |
| A-712 | Pyridin-3-ylmethyl | 4-Cyanophenyl | W1b (m = 0) |
| A-713 | Pyridin-3-ylmethyl | 4-(Piperidin-1-yl)phenyl | W1b (m = 0) |
| A-714 | Pyridin-3-ylmethyl | 4-(4-Methylpiperazin-1-yl)phenyl | W1b (m = 0) |
| A-715 | Pyridin-3-ylmethyl | 4-Pyrrolidin-1-ylphenyl | W1b (m = 0) |
| A-716 | Pyridin-3-ylmethyl | 4-(1H-Imidazol-1-yl)phenyl | W1b (m = 0) |
| A-717 | Pyridin-3-ylmethyl | 4-Morpholin-4-ylphenyl | W1b (m = 0) |
| A-718 | Pyridin-3-ylmethyl | 4-(Morpholin-4-ylmethyl)phenyl | W1b (m = 0) |
| A-719 | Pyridin-3-ylmethyl | 2,4-Difluorophenyl | W1b (m = 0) |
| A-720 | Pyridin-3-ylmethyl | 2,6-Difluorophenyl | W1b (m = 0) |
| A-721 | Pyridin-3-ylmethyl | 3,5-Difluorophenyl | W1b (m = 0) |
| A-722 | Pyridin-3-ylmethyl | 2,4-Dichlorophenyl | W1b (m = 0) |
| A-723 | Pyridin-3-ylmethyl | 2,6-Dichlorophenyl | W1b (m = 0) |
| A-724 | Pyridin-3-ylmethyl | 3,5-Dichlorophenyl | W1b (m = 0) |
| A-725 | Pyridin-3-ylmethyl | 2-Chloro-4-fluorophenyl | W1b (m = 0) |
| A-726 | Pyridin-3-ylmethyl | 2-Chloro-4-morpholin-4-ylphenyl | W1b (m = 0) |
| A-727 | Pyridin-3-ylmethyl | 2-Fluoro-4-morpholin-4-ylphenyl | W1b (m = 0) |
| A-728 | Pyridin-3-ylmethyl | Pyridin-2-yl | W1b (m = 0) |
| A-729 | Pyridin-3-ylmethyl | Pyridin-4-yl | W1b (m = 0) |

TABLE A-continued

| No. | R¹ | R² | W |
|---|---|---|---|
| A-730 | Pyridin-3-ylmethyl | Thien-2-yl | W1b (m = 0) |
| A-731 | Pyridin-3-ylmethyl | 2,3-Dihydrobenzo[b]furan-5-yl | W1b (m = 0) |
| A-732 | n-Butyl | Phenyl | W2a (m = 0) |
| A-733 | n-Butyl | 2-Methylphenyl | W2a (m = 0) |
| A-734 | n-Butyl | 2-Methoxyphenyl | W2a (m = 0) |
| A-735 | n-Butyl | 2-Chlorophenyl | W2a (m = 0) |
| A-736 | n-Butyl | 2-Fluorophenyl | W2a (m = 0) |
| A-737 | n-Butyl | 2-Trifluoromethylphenyl | W2a (m = 0) |
| A-738 | n-Butyl | 3-Methylphenyl | W2a (m = 0) |
| A-739 | n-Butyl | 3-Methoxyphenyl | W2a (m = 0) |
| A-740 | n-Butyl | 3-Chlorophenyl | W2a (m = 0) |
| A-741 | n-Butyl | 3-Fluorophenyl | W2a (m = 0) |
| A-742 | n-Butyl | 3-Trifluoromethylphenyl | W2a (m = 0) |
| A-743 | n-Butyl | 3-[(Phenylmethyl)oxy]phenyl | W2a (m = 0) |
| A-744 | n-Butyl | 3-Morpholin-4-ylphenyl | W2a (m = 0) |
| A-745 | n-Butyl | 3-(Morpholin-4-ylmethyl)phenyl | W2a (m = 0) |
| A-746 | n-Butyl | 3-Pyrrolidin-1-ylphenyl | W2a (m = 0) |
| A-747 | n-Butyl | 4-Methylphenyl | W2a (m = 0) |
| A-748 | n-Butyl | 4-(1-Methylethyl)phenyl | W2a (m = 0) |
| A-749 | n-Butyl | 4-Methoxyphenyl | W2a (m = 0) |
| A-750 | n-Butyl | 4-Chlorophenyl | W2a (m = 0) |
| A-751 | n-Butyl | 4-Fluorophenyl | W2a (m = 0) |
| A-752 | n-Butyl | 4-Trifluoromethylphenyl | W2a (m = 0) |
| A-753 | n-Butyl | 4-Diethylaminophenyl | W2a (m = 0) |
| A-754 | n-Butyl | 4-[(Diethylamino)methyl]phenyl | W2a (m = 0) |
| A-755 | n-Butyl | 4-Cyanophenyl | W2a (m = 0) |
| A-756 | n-Butyl | 4-(Piperidin-1-yl)phenyl | W2a (m = 0) |
| A-757 | n-Butyl | 4-(4-Methylpiperazin-1-yl)phenyl | W2a (m = 0) |
| A-758 | n-Butyl | 4-Pyrrolidin-1-ylphenyl | W2a (m = 0) |
| A-759 | n-Butyl | 4-(1H-Imidazol-1-yl)phenyl | W2a (m = 0) |
| A-760 | n-Butyl | 4-Morpholin-4-ylphenyl | W2a (m = 0) |
| A-761 | n-Butyl | 4-(Morpholin-4-ylmethyl)phenyl | W2a (m = 0) |
| A-762 | n-Butyl | 2,4-Difluorophenyl | W2a (m = 0) |
| A-763 | n-Butyl | 2,6-Difluorophenyl | W2a (m = 0) |
| A-764 | n-Butyl | 3,5-Difluorophenyl | W2a (m = 0) |
| A-765 | n-Butyl | 2,4-Dichlorophenyl | W2a (m = 0) |
| A-766 | n-Butyl | 2,6-Dichlorophenyl | W2a (m = 0) |
| A-767 | n-Butyl | 3,5-Dichlorophenyl | W2a (m = 0) |
| A-768 | n-Butyl | 2-Chloro-4-fluorophenyl | W2a (m = 0) |
| A-769 | n-Butyl | 2-Chloro-4-morpholin-4-ylphenyl | W2a (m = 0) |
| A-770 | n-Butyl | 2-Fluoro-4-morpholin-4-ylphenyl | W2a (m = 0) |
| A-771 | n-Butyl | Pyridin-2-yl | W2a (m = 0) |
| A-772 | n-Butyl | Pyridin-4-yl | W2a (m = 0) |
| A-773 | n-Butyl | Thien-2-yl | W2a (m = 0) |
| A-774 | n-Butyl | 2,3-Dihydrobenzo[b]furan-5-yl | W2a (m = 0) |
| A-775 | Isobutyl | Phenyl | W2a (m = 0) |
| A-776 | Isobutyl | 2-Methylphenyl | W2a (m = 0) |
| A-777 | Isobutyl | 2-Methoxyphenyl | W2a (m = 0) |
| A-778 | Isobutyl | 2-Chlorophenyl | W2a (m = 0) |
| A-779 | Isobutyl | 2-Fluorophenyl | W2a (m = 0) |
| A-780 | Isobutyl | 2-Trifluoromethylphenyl | W2a (m = 0) |
| A-781 | Isobutyl | 3-Methylphenyl | W2a (m = 0) |
| A-782 | Isobutyl | 3-Methoxyphenyl | W2a (m = 0) |
| A-783 | Isobutyl | 3-Chlorophenyl | W2a (m = 0) |
| A-784 | Isobutyl | 3-Fluorophenyl | W2a (m = 0) |
| A-785 | Isobutyl | 3-Trifluoromethylphenyl | W2a (m = 0) |
| A-786 | Isobutyl | 3-[(Phenylmethyl)oxy]phenyl | W2a (m = 0) |
| A-787 | Isobutyl | 3-Morpholin-4-ylphenyl | W2a (m = 0) |
| A-788 | Isobutyl | 3-(Morpholin-4-ylmethyl)phenyl | W2a (m = 0) |
| A-789 | Isobutyl | 3-Pyrrolidin-1-ylphenyl | W2a (m = 0) |
| A-790 | Isobutyl | 4-Methylphenyl | W2a (m = 0) |
| A-791 | Isobutyl | 4-(1-Methylethyl)phenyl | W2a (m = 0) |
| A-792 | Isobutyl | 4-Methoxyphenyl | W2a (m = 0) |
| A-793 | Isobutyl | 4-Chlorophenyl | W2a (m = 0) |
| A-794 | Isobutyl | 4-Fluorophenyl | W2a (m = 0) |
| A-795 | Isobutyl | 4-Trifluoromethylphenyl | W2a (m = 0) |
| A-796 | Isobutyl | 4-Diethylaminophenyl | W2a (m = 0) |
| A-797 | Isobutyl | 4-[(Diethylamino)methyl]phenyl | W2a (m = 0) |
| A-798 | Isobutyl | 4-Cyanophenyl | W2a (m = 0) |
| A-799 | Isobutyl | 4-(Piperidin-1-yl)phenyl | W2a (m = 0) |
| A-800 | Isobutyl | 4-(4-Methylpiperazin-1-yl)phenyl | W2a (m = 0) |
| A-801 | Isobutyl | 4-Pyrrolidin-1-ylphenyl | W2a (m = 0) |
| A-802 | Isobutyl | 4-(1H-Imidazol-1-yl)phenyl | W2a (m = 0) |
| A-803 | Isobutyl | 4-Morpholin-4-ylphenyl | W2a (m = 0) |
| A-804 | Isobutyl | 4-(Morpholin-4-ylmethyl)phenyl | W2a (m = 0) |
| A-805 | Isobutyl | 2,4-Difluorophenyl | W2a (m = 0) |
| A-806 | Isobutyl | 2,6-Difluorophenyl | W2a (m = 0) |
| A-807 | Isobutyl | 3,5-Difluorophenyl | W2a (m = 0) |

TABLE A-continued

| No. | R¹ | R² | W |
|---|---|---|---|
| A-808 | Isobutyl | 2,4-Dichlorophenyl | W2a (m = 0) |
| A-809 | Isobutyl | 2,6-Dichlorophenyl | W2a (m = 0) |
| A-810 | Isobutyl | 3,5-Dichlorophenyl | W2a (m = 0) |
| A-811 | Isobutyl | 2-Chloro-4-fluorophenyl | W2a (m = 0) |
| A-812 | Isobutyl | 2-Chloro-4-morpholin-4-ylphenyl | W2a (m = 0) |
| A-813 | Isobutyl | 2-Fluoro-4-morpholin-4-ylphenyl | W2a (m = 0) |
| A-814 | Isobutyl | Pyridin-2-yl | W2a (m = 0) |
| A-815 | Isobutyl | Pyridin-4-yl | W2a (m = 0) |
| A-816 | Isobutyl | Thien-2-yl | W2a (m = 0) |
| A-817 | Isobutyl | 2,3-Dihydrobenzo[b]furan-5-yl | W2a (m = 0) |
| A-818 | Benzyl | Phenyl | W2a (m = 0) |
| A-819 | Benzyl | 2-Methylphenyl | W2a (m = 0) |
| A-820 | Benzyl | 2-Methoxyphenyl | W2a (m = 0) |
| A-821 | Benzyl | 2-Chlorophenyl | W2a (m = 0) |
| A-822 | Benzyl | 2-Fluorophenyl | W2a (m = 0) |
| A-823 | Benzyl | 2-Trifluoromethylphenyl | W2a (m = 0) |
| A-824 | Benzyl | 3-Methylphenyl | W2a (m = 0) |
| A-825 | Benzyl | 3-Methoxyphenyl | W2a (m = 0) |
| A-826 | Benzyl | 3-Chlorophenyl | W2a (m = 0) |
| A-827 | Benzyl | 3-Fluorophenyl | W2a (m = 0) |
| A-828 | Benzyl | 3-Trifluoromethylphenyl | W2a (m = 0) |
| A-829 | Benzyl | 3-[(Phenylmethyl)oxy]phenyl | W2a (m = 0) |
| A-830 | Benzyl | 3-Morpholin-4-ylphenyl | W2a (m = 0) |
| A-831 | Benzyl | 3-(Morpholin-4-ylmethyl)phenyl | W2a (m = 0) |
| A-832 | Benzyl | 3-Pyrrolidin-1-ylphenyl | W2a (m = 0) |
| A-833 | Benzyl | 4-Methylphenyl | W2a (m = 0) |
| A-834 | Benzyl | 4-(1-Methylethyl)phenyl | W2a (m = 0) |
| A-835 | Benzyl | 4-Methoxyphenyl | W2a (m = 0) |
| A-836 | Benzyl | 4-Chlorophenyl | W2a (m = 0) |
| A-837 | Benzyl | 4-Fluorophenyl | W2a (m = 0) |
| A-838 | Benzyl | 4-Trifluoromethylphenyl | W2a (m = 0) |
| A-839 | Benzyl | 4-Diethylaminophenyl | W2a (m = 0) |
| A-840 | Benzyl | 4-[(Diethylamino)methyl]phenyl | W2a (m = 0) |
| A-841 | Benzyl | 4-Cyanophenyl | W2a (m = 0) |
| A-842 | Benzyl | 4-(Piperidin-1-yl)phenyl | W2a (m = 0) |
| A-843 | Benzyl | 4-(4-Methylpiperazin-1-yl)phenyl | W2a (m = 0) |
| A-844 | Benzyl | 4-Pyrrolidin-1-ylphenyl | W2a (m = 0) |
| A-845 | Benzyl | 4-(1H-Imidazol-1-yl)phenyl | W2a (m = 0) |
| A-846 | Benzyl | 4-Morpholin-4-ylphenyl | W2a (m = 0) |
| A-847 | Benzyl | 4-(Morpholin-4-ylmethyl)phenyl | W2a (m = 0) |
| A-848 | Benzyl | 2,4-Difluorophenyl | W2a (m = 0) |
| A-849 | Benzyl | 2,6-Difluorophenyl | W2a (m = 0) |
| A-850 | Benzyl | 3,5-Difluorophenyl | W2a (m = 0) |
| A-851 | Benzyl | 2,4-Dichlorophenyl | W2a (m = 0) |
| A-852 | Benzyl | 2,6-Dichlorophenyl | W2a (m = 0) |
| A-853 | Benzyl | 3,5-Dichlorophenyl | W2a (m = 0) |
| A-854 | Benzyl | 2-Chloro-4-fluorophenyl | W2a (m = 0) |
| A-855 | Benzyl | 2-Chloro-4-morpholin-4-ylphenyl | W2a (m = 0) |
| A-856 | Benzyl | 2-Fluoro-4-morpholin-4-ylphenyl | W2a (m = 0) |
| A-857 | Benzyl | Pyridin-2-yl | W2a (m = 0) |
| A-858 | Benzyl | Pyridin-4-yl | W2a (m = 0) |
| A-859 | Benzyl | Thien-2-yl | W2a (m = 0) |
| A-860 | Benzyl | 2,3-Dihydrobenzo[b]furan-5-yl | W2a (m = 0) |
| A-861 | 4-Chlorobenzyl | Phenyl | W2a (m = 0) |
| A-862 | 4-Chlorobenzyl | 2-Methylphenyl | W2a (m = 0) |
| A-863 | 4-Chlorobenzyl | 2-Methoxyphenyl | W2a (m = 0) |
| A-864 | 4-Chlorobenzyl | 2-Chlorophenyl | W2a (m = 0) |
| A-865 | 4-Chlorobenzyl | 2-Fluorophenyl | W2a (m = 0) |
| A-866 | 4-Chlorobenzyl | 2-Trifluoromethylphenyl | W2a (m = 0) |
| A-867 | 4-Chlorobenzyl | 3-Methylphenyl | W2a (m = 0) |
| A-868 | 4-Chlorobenzyl | 3-Methoxyphenyl | W2a (m = 0) |
| A-869 | 4-Chlorobenzyl | 3-Chlorophenyl | W2a (m = 0) |
| A-870 | 4-Chlorobenzyl | 3-Fluorophenyl | W2a (m = 0) |
| A-871 | 4-Chlorobenzyl | 3-Trifluoromethylphenyl | W2a (m = 0) |
| A-872 | 4-Chlorobenzyl | 3-[(Phenylmethyl)oxy]phenyl | W2a (m = 0) |
| A-873 | 4-Chlorobenzyl | 3-Morpholin-4-ylphenyl | W2a (m = 0) |
| A-874 | 4-Chlorobenzyl | 3-(Morpholin-4-ylmethyl)phenyl | W2a (m = 0) |
| A-875 | 4-Chlorobenzyl | 3-Pyrrolidin-1-ylphenyl | W2a (m = 0) |
| A-876 | 4-Chlorobenzyl | 4-Methylphenyl | W2a (m = 0) |
| A-877 | 4-Chlorobenzyl | 4-(1-Methylethyl)phenyl | W2a (m = 0) |
| A-878 | 4-Chlorobenzyl | 4-Methoxyphenyl | W2a (m = 0) |
| A-879 | 4-Chlorobenzyl | 4-Chlorophenyl | W2a (m = 0) |
| A-880 | 4-Chlorobenzyl | 4-Fluorophenyl | W2a (m = 0) |
| A-881 | 4-Chlorobenzyl | 4-Trifluoromethylphenyl | W2a (m = 0) |
| A-882 | 4-Chlorobenzyl | 4-Diethylaminophenyl | W2a (m = 0) |
| A-883 | 4-Chlorobenzyl | 4-[(Diethylamino)methyl]phenyl | W2a (m = 0) |
| A-884 | 4-Chlorobenzyl | 4-Cyanophenyl | W2a (m = 0) |
| A-885 | 4-Chlorobenzyl | 4-(Piperidin-1-yl)phenyl | W2a (m = 0) |

TABLE A-continued

| No. | R¹ | R² | W |
|---|---|---|---|
| A-886 | 4-Chlorobenzyl | 4-(4-Methylpiperazin-1-yl)phenyl | W2a (m = 0) |
| A-887 | 4-Chlorobenzyl | 4-Pyrrolidin-1-ylphenyl | W2a (m = 0) |
| A-888 | 4-Chlorobenzyl | 4-(1H-Imidazol-1-yl)phenyl | W2a (m = 0) |
| A-889 | 4-Chlorobenzyl | 4-Morpholin-4-ylphenyl | W2a (m = 0) |
| A-890 | 4-Chlorobenzyl | 4-(Morpholin-4-ylmethyl)phenyl | W2a (m = 0) |
| A-891 | 4-Chlorobenzyl | 2,4-Difluorophenyl | W2a (m = 0) |
| A-892 | 4-Chlorobenzyl | 2,6-Difluorophenyl | W2a (m = 0) |
| A-893 | 4-Chlorobenzyl | 3,5-Difluorophenyl | W2a (m = 0) |
| A-894 | 4-Chlorobenzyl | 2,4-Dichlorophenyl | W2a (m = 0) |
| A-895 | 4-Chlorobenzyl | 2,6-Dichlorophenyl | W2a (m = 0) |
| A-896 | 4-Chlorobenzyl | 3,5-Dichlorophenyl | W2a (m = 0) |
| A-897 | 4-Chlorobenzyl | 2-Chloro-4-fluorophenyl | W2a (m = 0) |
| A-898 | 4-Chlorobenzyl | 2-Chloro-4-morpholin-4-ylphenyl | W2a (m = 0) |
| A-899 | 4-Chlorobenzyl | 2-Fluoro-4-morpholin-4-ylphenyl | W2a (m = 0) |
| A-900 | 4-Chlorobenzyl | Pyridin-2-yl | W2a (m = 0) |
| A-901 | 4-Chlorobenzyl | Pyridin-4-yl | W2a (m = 0) |
| A-902 | 4-Chlorobenzyl | Thien-2-yl | W2a (m = 0) |
| A-903 | 4-Chlorobenzyl | 2,3-Dihydrobenzo[b]furan-5-yl | W2a (m = 0) |
| A-904 | 4-Methoxybenzyl | Phenyl | W2a (m = 0) |
| A-905 | 4-Methoxybenzyl | 2-Methylphenyl | W2a (m = 0) |
| A-906 | 4-Methoxybenzyl | 2-Methoxyphenyl | W2a (m = 0) |
| A-907 | 4-Methoxybenzyl | 2-Chlorophenyl | W2a (m = 0) |
| A-908 | 4-Methoxybenzyl | 2-Fluorophenyl | W2a (m = 0) |
| A-909 | 4-Methoxybenzyl | 2-Trifluoromethylphenyl | W2a (m = 0) |
| A-910 | 4-Methoxybenzyl | 3-Methylphenyl | W2a (m = 0) |
| A-911 | 4-Methoxybenzyl | 3-Methoxyphenyl | W2a (m = 0) |
| A-912 | 4-Methoxybenzyl | 3-Chlorophenyl | W2a (m = 0) |
| A-913 | 4-Methoxybenzyl | 3-Fluorophenyl | W2a (m = 0) |
| A-914 | 4-Methoxybenzyl | 3-Trifluoromethylphenyl | W2a (m = 0) |
| A-915 | 4-Methoxybenzyl | 3-[(Phenylmethyl)oxy]phenyl | W2a (m = 0) |
| A-916 | 4-Methoxybenzyl | 3-Morpholin-4-ylphenyl | W2a (m = 0) |
| A-917 | 4-Methoxybenzyl | 3-(Morpholin-4-ylmethyl)phenyl | W2a (m = 0) |
| A-918 | 4-Methoxybenzyl | 3-Pyrrolidin-1-ylphenyl | W2a (m = 0) |
| A-919 | 4-Methoxybenzyl | 4-Methylphenyl | W2a (m = 0) |
| A-920 | 4-Methoxybenzyl | 4-(1-Methylethyl)phenyl | W2a (m = 0) |
| A-921 | 4-Methoxybenzyl | 4-Methoxyphenyl | W2a (m = 0) |
| A-922 | 4-Methoxybenzyl | 4-Chlorophenyl | W2a (m = 0) |
| A-923 | 4-Methoxybenzyl | 4-Fluorophenyl | W2a (m = 0) |
| A-924 | 4-Methoxybenzyl | 4-Trifluoromethylphenyl | W2a (m = 0) |
| A-925 | 4-Methoxybenzyl | 4-Diethylaminophenyl | W2a (m = 0) |
| A-926 | 4-Methoxybenzyl | 4-[(Diethylamino)methyl]phenyl | W2a (m = 0) |
| A-927 | 4-Methoxybenzyl | 4-Cyanophenyl | W2a (m = 0) |
| A-928 | 4-Methoxybenzyl | 4-(Piperidin-1-yl)phenyl | W2a (m = 0) |
| A-929 | 4-Methoxybenzyl | 4-(4-Methylpiperazin-1-yl)phenyl | W2a (m = 0) |
| A-930 | 4-Methoxybenzyl | 4-Pyrrolidin-1-ylphenyl | W2a (m = 0) |
| A-931 | 4-Methoxybenzyl | 4-(1H-Imidazol-1-yl)phenyl | W2a (m = 0) |
| A-932 | 4-Methoxybenzyl | 4-Morpholin-4-ylphenyl | W2a (m = 0) |
| A-933 | 4-Methoxybenzyl | 4-(Morpholin-4-ylmethyl)phenyl | W2a (m = 0) |
| A-934 | 4-Methoxybenzyl | 2,4-Difluorophenyl | W2a (m = 0) |
| A-935 | 4-Methoxybenzyl | 2,6-Difluorophenyl | W2a (m = 0) |
| A-936 | 4-Methoxybenzyl | 3,5-Difluorophenyl | W2a (m = 0) |
| A-937 | 4-Methoxybenzyl | 2,4-Dichlorophenyl | W2a (m = 0) |
| A-938 | 4-Methoxybenzyl | 2,6-Dichlorophenyl | W2a (m = 0) |
| A-939 | 4-Methoxybenzyl | 3,5-Dichlorophenyl | W2a (m = 0) |
| A-940 | 4-Methoxybenzyl | 2-Chloro-4-fluorophenyl | W2a (m = 0) |
| A-941 | 4-Methoxybenzyl | 2-Chloro-4-morpholin-4-ylphenyl | W2a (m = 0) |
| A-942 | 4-Methoxybenzyl | 2-Fluoro-4-morpholin-4-ylphenyl | W2a (m = 0) |
| A-943 | 4-Methoxybenzyl | Pyridin-2-yl | W2a (m = 0) |
| A-944 | 4-Methoxybenzyl | Pyridin-4-yl | W2a (m = 0) |
| A-945 | 4-Methoxybenzyl | Thien-2-yl | W2a (m = 0) |
| A-946 | 4-Methoxybenzyl | 2,3-Dihydrobenzo[b]furan-5-yl | W2a (m = 0) |
| A-947 | Cyclohexylmethyl | Phenyl | W2a (m = 0) |
| A-948 | Cyclohexylmethyl | 2-Methylphenyl | W2a (m = 0) |
| A-949 | Cyclohexylmethyl | 2-Methoxyphenyl | W2a (m = 0) |
| A-950 | Cyclohexylmethyl | 2-Chlorophenyl | W2a (m = 0) |
| A-951 | Cyclohexylmethyl | 2-Fluorophenyl | W2a (m = 0) |
| A-952 | Cyclohexylmethyl | 2-Trifluoromethylphenyl | W2a (m = 0) |
| A-953 | Cyclohexylmethyl | 3-Methylphenyl | W2a (m = 0) |
| A-954 | Cyclohexylmethyl | 3-Methoxyphenyl | W2a (m = 0) |
| A-955 | Cyclohexylmethyl | 3-Chlorophenyl | W2a (m = 0) |
| A-956 | Cyclohexylmethyl | 3-Fluorophenyl | W2a (m = 0) |
| A-957 | Cyclohexylmethyl | 3-Trifluoromethylphenyl | W2a (m = 0) |
| A-958 | Cyclohexylmethyl | 3-[(Phenylmethyl)oxy]phenyl | W2a (m = 0) |
| A-959 | Cyclohexylmethyl | 3-Morpholin-4-ylphenyl | W2a (m = 0) |
| A-960 | Cyclohexylmethyl | 3-(Morpholin-4-ylmethyl)phenyl | W2a (m = 0) |
| A-961 | Cyclohexylmethyl | 3-Pyrrolidin-1-ylphenyl | W2a (m = 0) |
| A-962 | Cyclohexylmethyl | 4-Methylphenyl | W2a (m = 0) |
| A-963 | Cyclohexylmethyl | 4-(1-Methylethyl)phenyl | W2a (m = 0) |

TABLE A-continued

| No. | R¹ | R² | W |
|---|---|---|---|
| A-964 | Cyclohexylmethyl | 4-Methoxyphenyl | W2a (m = 0) |
| A-965 | Cyclohexylmethyl | 4-Chlorophenyl | W2a (m = 0) |
| A-966 | Cyclohexylmethyl | 4-Fluorophenyl | W2a (m = 0) |
| A-967 | Cyclohexylmethyl | 4-Trifluoromethylphenyl | W2a (m = 0) |
| A-968 | Cyclohexylmethyl | 4-Diethylaminophenyl | W2a (m = 0) |
| A-969 | Cyclohexylmethyl | 4-[(Diethylamino)methyl]phenyl | W2a (m = 0) |
| A-970 | Cyclohexylmethyl | 4-Cyanophenyl | W2a (m = 0) |
| A-971 | Cyclohexylmethyl | 4-(Piperidin-1-yl)phenyl | W2a (m = 0) |
| A-972 | Cyclohexylmethyl | 4-(4-Methylpiperazin-1-yl)phenyl | W2a (m = 0) |
| A-973 | Cyclohexylmethyl | 4-Pyrrolidin-1-ylphenyl | W2a (m = 0) |
| A-974 | Cyclohexylmethyl | 4-(1H-Imidazol-1-yl)phenyl | W2a (m = 0) |
| A-975 | Cyclohexylmethyl | 4-Morpholin-4-ylphenyl | W2a (m = 0) |
| A-976 | Cyclohexylmethyl | 4-(Morpholin-4-ylmethyl)phenyl | W2a (m = 0) |
| A-977 | Cyclohexylmethyl | 2,4-Difluorophenyl | W2a (m = 0) |
| A-978 | Cyclohexylmethyl | 2,6-Difluorophenyl | W2a (m = 0) |
| A-979 | Cyclohexylmethyl | 3,5-Difluorophenyl | W2a (m = 0) |
| A-980 | Cyclohexylmethyl | 2,4-Dichlorophenyl | W2a (m = 0) |
| A-981 | Cyclohexylmethyl | 2,6-Dichlorophenyl | W2a (m = 0) |
| A-982 | Cyclohexylmethyl | 3,5-Dichlorophenyl | W2a (m = 0) |
| A-983 | Cyclohexylmethyl | 2-Chloro-4-fluorophenyl | W2a (m = 0) |
| A-984 | Cyclohexylmethyl | 2-Chloro-4-morpholin-4-ylphenyl | W2a (m = 0) |
| A-985 | Cyclohexylmethyl | 2-Fluoro-4-morpholin-4-ylphenyl | W2a (m = 0) |
| A-986 | Cyclohexylmethyl | Pyridin-2-yl | W2a (m = 0) |
| A-987 | Cyclohexylmethyl | Pyridin-4-yl | W2a (m = 0) |
| A-988 | Cyclohexylmethyl | Thien-2-yl | W2a (m = 0) |
| A-989 | Cyclohexylmethyl | 2,3-Dihydrobenzo[b]furan-5-yl | W2a (m = 0) |
| A-990 | 2-Thienylmethyl | Phenyl | W2a (m = 0) |
| A-991 | 2-Thienylmethyl | 2-Methylphenyl | W2a (m = 0) |
| A-992 | 2-Thienylmethyl | 2-Methoxyphenyl | W2a (m = 0) |
| A-993 | 2-Thienylmethyl | 2-Chlorophenyl | W2a (m = 0) |
| A-994 | 2-Thienylmethyl | 2-Fluorophenyl | W2a (m = 0) |
| A-995 | 2-Thienylmethyl | 2-Trifluoromethylphenyl | W2a (m = 0) |
| A-996 | 2-Thienylmethyl | 3-Methylphenyl | W2a (m = 0) |
| A-997 | 2-Thienylmethyl | 3-Methoxyphenyl | W2a (m = 0) |
| A-998 | 2-Thienylmethyl | 3-Chlorophenyl | W2a (m = 0) |
| A-999 | 2-Thienylmethyl | 3-Fluorophenyl | W2a (m = 0) |
| A-1000 | 2-Thienylmethyl | 3-Trifluoromethylphenyl | W2a (m = 0) |
| A-1001 | 2-Thienylmethyl | 3-[(Phenylmethyl)oxy]phenyl | W2a (m = 0) |
| A-1002 | 2-Thienylmethyl | 3-Morpholin-4-ylphenyl | W2a (m = 0) |
| A-1003 | 2-Thienylmethyl | 3-(Morpholin-4-ylmethyl)phenyl | W2a (m = 0) |
| A-1004 | 2-Thienylmethyl | 3-Pyrrolidin-1-ylphenyl | W2a (m = 0) |
| A-1005 | 2-Thienylmethyl | 4-Methylphenyl | W2a (m = 0) |
| A-1006 | 2-Thienylmethyl | 4-(1-Methylethyl)phenyl | W2a (m = 0) |
| A-1007 | 2-Thienylmethyl | 4-Methoxyphenyl | W2a (m = 0) |
| A-1008 | 2-Thienylmethyl | 4-Chlorophenyl | W2a (m = 0) |
| A-1009 | 2-Thienylmethyl | 4-Fluorophenyl | W2a (m = 0) |
| A-1010 | 2-Thienylmethyl | 4-Trifluoromethylphenyl | W2a (m = 0) |
| A-1011 | 2-Thienylmethyl | 4-Diethylaminophenyl | W2a (m = 0) |
| A-1012 | 2-Thienylmethyl | 4-[(Diethylamino)methyl]phenyl | W2a (m = 0) |
| A-1013 | 2-Thienylmethyl | 4-Cyanophenyl | W2a (m = 0) |
| A-1014 | 2-Thienylmethyl | 4-(Piperidin-1-yl)phenyl | W2a (m = 0) |
| A-1015 | 2-Thienylmethyl | 4-(4-Methylpiperazin-1-yl)phenyl | W2a (m = 0) |
| A-1016 | 2-Thienylmethyl | 4-Pyrrolidin-1-ylphenyl | W2a (m = 0) |
| A-1017 | 2-Thienylmethyl | 4-(1H-Imidazol-1-yl)phenyl | W2a (m = 0) |
| A-1018 | 2-Thienylmethyl | 4-Morpholin-4-ylphenyl | W2a (m = 0) |
| A-1019 | 2-Thienylmethyl | 4-(Morpholin-4-ylmethyl)phenyl | W2a (m = 0) |
| A-1020 | 2-Thienylmethyl | 2,4-Difluorophenyl | W2a (m = 0) |
| A-1021 | 2-Thienylmethyl | 2,6-Difluorophenyl | W2a (m = 0) |
| A-1022 | 2-Thienylmethyl | 3,5-Difluorophenyl | W2a (m = 0) |
| A-1023 | 2-Thienylmethyl | 2,4-Dichlorophenyl | W2a (m = 0) |
| A-1024 | 2-Thienylmethyl | 2,6-Dichlorophenyl | W2a (m = 0) |
| A-1025 | 2-Thienylmethyl | 3,5-Dichlorophenyl | W2a (m = 0) |
| A-1026 | 2-Thienylmethyl | 2-Chloro-4-fluorophenyl | W2a (m = 0) |
| A-1027 | 2-Thienylmethyl | 2-Chloro-4-morpholin-4-ylphenyl | W2a (m = 0) |
| A-1028 | 2-Thienylmethyl | 2-Fluoro-4-morpholin-4-ylphenyl | W2a (m = 0) |
| A-1029 | 2-Thienylmethyl | Pyridin-2-yl | W2a (m = 0) |
| A-1030 | 2-Thienylmethyl | Pyridin-4-yl | W2a (m = 0) |
| A-1031 | 2-Thienylmethyl | Thien-2-yl | W2a (m = 0) |
| A-1032 | 2-Thienylmethyl | 2,3-Dihydrobenzo[b]furan-5-yl | W2a (m = 0) |
| A-1033 | Pyridin-3-ylmethyl | Phenyl | W2a (m = 0) |
| A-1034 | Pyridin-3-ylmethyl | 2-Methylphenyl | W2a (m = 0) |
| A-1035 | Pyridin-3-ylmethyl | 2-Methoxyphenyl | W2a (m = 0) |
| A-1036 | Pyridin-3-ylmethyl | 2-Chlorophenyl | W2a (m = 0) |
| A-1037 | Pyridin-3-ylmethyl | 2-Fluorophenyl | W2a (m = 0) |
| A-1038 | Pyridin-3-ylmethyl | 2-Trifluoromethylphenyl | W2a (m = 0) |
| A-1039 | Pyridin-3-ylmethyl | 3-Methylphenyl | W2a (m = 0) |
| A-1040 | Pyridin-3-ylmethyl | 3-Methoxyphenyl | W2a (m = 0) |
| A-1041 | Pyridin-3-ylmethyl | 3-Chlorophenyl | W2a (m = 0) |

TABLE A-continued

| No. | R¹ | R² | W |
|---|---|---|---|
| A-1042 | Pyridin-3-ylmethyl | 3-Fluorophenyl | W2a (m = 0) |
| A-1043 | Pyridin-3-ylmethyl | 3-Trifluoromethylphenyl | W2a (m = 0) |
| A-1044 | Pyridin-3-ylmethyl | 3-[(Phenylmethyl)oxy]phenyl | W2a (m = 0) |
| A-1045 | Pyridin-3-ylmethyl | 3-Morpholin-4-ylphenyl | W2a (m = 0) |
| A-1046 | Pyridin-3-ylmethyl | 3-(Morpholin-4-ylmethyl)phenyl | W2a (m = 0) |
| A-1047 | Pyridin-3-ylmethyl | 3-Pyrrolidin-1-ylphenyl | W2a (m = 0) |
| A-1048 | Pyridin-3-ylmethyl | 4-Methylphenyl | W2a (m = 0) |
| A-1049 | Pyridin-3-ylmethyl | 4-(1-Methylethyl)phenyl | W2a (m = 0) |
| A-1050 | Pyridin-3-ylmethyl | 4-Methoxyphenyl | W2a (m = 0) |
| A-1051 | Pyridin-3-ylmethyl | 4-Chlorophenyl | W2a (m = 0) |
| A-1052 | Pyridin-3-ylmethyl | 4-Fluorophenyl | W2a (m = 0) |
| A-1053 | Pyridin-3-ylmethyl | 4-Trifluoromethylphenyl | W2a (m = 0) |
| A-1054 | Pyridin-3-ylmethyl | 4-Diethylaminophenyl | W2a (m = 0) |
| A-1055 | Pyridin-3-ylmethyl | 4-[(Diethylamino)methyl]phenyl | W2a (m = 0) |
| A-1056 | Pyridin-3-ylmethyl | 4-Cyanophenyl | W2a (m = 0) |
| A-1057 | Pyridin-3-ylmethyl | 4-(Piperidin-1-yl)phenyl | W2a (m = 0) |
| A-1058 | Pyridin-3-ylmethyl | 4-(4-Methylpiperazin-1-yl)phenyl | W2a (m = 0) |
| A-1059 | Pyridin-3-ylmethyl | 4-Pyrrolidin-1-ylphenyl | W2a (m = 0) |
| A-1060 | Pyridin-3-ylmethyl | 4-(1H-Imidazol-1-yl)phenyl | W2a (m = 0) |
| A-1061 | Pyridin-3-ylmethyl | 4-Morpholin-4-ylphenyl | W2a (m = 0) |
| A-1062 | Pyridin-3-ylmethyl | 4-(Morpholin-4-ylmethyl)phenyl | W2a (m = 0) |
| A-1063 | Pyridin-3-ylmethyl | 2,4-Difluorophenyl | W2a (m = 0) |
| A-1064 | Pyridin-3-ylmethyl | 2,6-Difluorophenyl | W2a (m = 0) |
| A-1065 | Pyridin-3-ylmethyl | 3,5-Difluorophenyl | W2a (m = 0) |
| A-1066 | Pyridin-3-ylmethyl | 2,4-Dichlorophenyl | W2a (m = 0) |
| A-1067 | Pyridin-3-ylmethyl | 2,6-Dichlorophenyl | W2a (m = 0) |
| A-1068 | Pyridin-3-ylmethyl | 3,5-Dichlorophenyl | W2a (m = 0) |
| A-1069 | Pyridin-3-ylmethyl | 2-Chloro-4-fluorophenyl | W2a (m = 0) |
| A-1070 | Pyridin-3-ylmethyl | 2-Chloro-4-morpholin-4-ylphenyl | W2a (m = 0) |
| A-1071 | Pyridin-3-ylmethyl | 2-Fluoro-4-morpholin-4-ylphenyl | W2a (m = 0) |
| A-1072 | Pyridin-3-ylmethyl | Pyridin-2-yl | W2a (m = 0) |
| A-1073 | Pyridin-3-ylmethyl | Pyridin-4-yl | W2a (m = 0) |
| A-1074 | Pyridin-3-ylmethyl | Thien-2-yl | W2a (m = 0) |
| A-1075 | Pyridin-3-ylmethyl | 2,3-Dihydrobenzo[b]furan-5-yl | W2a (m = 0) |
| A-1076 | n-Butyl | 4,5-dihydro-2H-benzo[g]indazol-2-yl | |
| A-1077 | n-Butyl | 1H-Indazol-1-yl | |
| A-1078 | n-Butyl | 2H-Indazol-2-yl | |
| A-1079 | n-Butyl | Chromeno[4,3-c]pyrazol-2(4H)-yl | |
| A-1080 | Isobutyl | 4,5-dihydro-2H-benzo[g]indazol-2-yl | |
| A-1081 | Isobutyl | 1H-Indazol-1-yl | |
| A-1082 | Isobutyl | 2H-Indazol-2-yl | |
| A-1083 | Isobutyl | Chromeno[4,3-c]pyrazol-2(4H)-yl | |
| A-1084 | Benzyl | 4,5-dihydro-2H-benzo[g]indazol-2-yl | |
| A-1085 | Benzyl | 1H-Indazol-1-yl | |
| A-1086 | Benzyl | 2H-Indazol-2-yl | |
| A-1087 | Benzyl | Chromeno[4,3-c]pyrazol-2(4H)-yl | |
| A-1088 | 4-Chlorobenzyl | 4,5-dihydro-2H-benzo[g]indazol-2-yl | |
| A-1089 | 4-Chlorobenzyl | 1H-Indazol-1-yl | |
| A-1090 | 4-Chlorobenzyl | 2H-Indazol-2-yl | |
| A-1091 | 4-Chlorobenzyl | Chromeno[4,3-c]pyrazol-2(4H)-yl | |
| A-1092 | 4-Methoxybenzyl | 4,5-dihydro-2H-benzo[g]indazol-2-yl | |
| A-1093 | 4-Methoxybenzyl | 1H-Indazol-1-yl | |
| A-1094 | 4-Methoxybenzyl | 2H-Indazol-2-yl | |
| A-1095 | 4-Methoxybenzyl | Chromeno[4,3-c]pyrazol-2(4H)-yl | |
| A-1096 | Cyclohexylmethyl | 4,5-dihydro-2H-benzo[g]indazol-2-yl | |
| A-1097 | Cyclohexylmethyl | 1H-Indazol-1-yl | |
| A-1098 | Cyclohexylmethyl | 2H-Indazol-2-yl | |
| A-1099 | Cyclohexylmethyl | Chromeno[4,3-c]pyrazol-2(4H)-yl | |
| A-1100 | 2-Thienylmethyl | 4,5-dihydro-2H-benzo[g]indazol-2-yl | |
| A-1101 | 2-Thienylmethyl | 1H-Indazol-1-yl | |
| A-1102 | 2-Thienylmethyl | 2H-Indazol-2-yl | |
| A-1103 | 2-Thienylmethyl | Chromeno[4,3-c]pyrazol-2(4H)-yl | |
| A-1104 | Pyridin-3-ylmethyl | 4,5-dihydro-2H-benzo[g]indazol-2-yl | |
| A-1105 | Pyridin-3-ylmethyl | 1H-Indazol-1-yl | |
| A-1106 | Pyridin-3-ylmethyl | 2H-Indazol-2-yl | |
| A-1107 | Pyridin-3-ylmethyl | Chromeno[4,3-c]pyrazol-2(4H)-yl | |

The compounds of the invention of the general formula I and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", 5$^{th}$ edition, Wiley & Sons and the literature cited therein, and R. Larock, "Comprehensive Organic Transformations", 2$^{nd}$ edition, Weinheim, 1999 and the literature cited therein. The carboxamide compounds of the invention of the general formula I are advantageously prepared by the methods described below and/or in the experimental section.

The compounds of the formula I can be prepared from the compounds of the formula II by standard reactions for the transformation of a ketocarbonyl group into a cyclic ketal, 1,3-thioketal or 1-thio-3-oxoketal as described e.g. in J.

Chem. Soc. 1993, 115, 8125, Journal of Combinatorial Chemistry (2004), 6(2), 181-195, Journal of Medicinal Chemistry (1993), 36(22), 3472-80 or Bioorganic & Medicinal Chemistry, 2007, 15, 931-938.

In a preferred embodiment of the invention, the compounds of the formula I, wherein $R^{3a}$ together with $R^{3b}$ form a moiety Z-Alk-O with Z being O or S, can be prepared according to the reaction depicted in scheme 1:

Scheme 1:

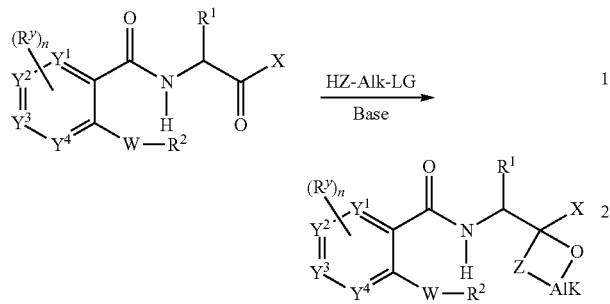

In scheme 1, the variables n, $R^y$, $Y^1$, $Y^2$, $Y^3$, $Y^4$, $R^1$, $R^2$, W, X and Alk are as defined herein. Z is oxygen or sulfur, LG is a suitable leaving group such as halogen, in particular chlorine, bromine or iodine, or arylsulfonat or alkylsulfonat $R-SO_3^-$ with R being selected from $C_1$-$C_4$-alkyl and phenyl the latter being optionally substituted by 1 or 2 $C_1$-$C_4$-alkyl radicals.

The compound of formula II and the bivalent compound HZ-Alk-LG are preferably reacted in the presence of a base. Suitable bases include inorganic bases such as alkalimetal-hydrides, e.g. NaH or KH, alkalimetal alkoholates such as sodium methoxide or sodium ethoxide, alkalimetal hydroxides such as sodium hydroxide or potassium hydroxide, alkalimetal carbonates such as sodium carbonate or potassium carbonate, and organic bases e.g. nitrogen bases, in particular tertiary amines such as trialkylamines, aryldialkylamines such as DMAP (4-dimethylaminopyridine) and preferably polycyclic amines such as DABCO (1,4-diazabicyclo[2.2.2] octane) and amidine bases such as DBN (1,8-diazabicyclo [5.4.0]undec-7-ene) and DBU (1,6-diazabicyclo[4.3.0]non-5-ene). The reaction is preferably performed in an organic solvent, in particular an aprotic polar solvent or solvent mixture such dimethylformamide (DMF), dimethylacetamide, acetonitrile, dimethylsulfoxide, hexamethylphosphortriamide (HMPT), tetramethylurea or N,N-dimethylimidazolinone. The molar ratio of the compound HZ-Alk-LG to the compound II is preferably at least 1:1. Preferably the compound HZ-Alk-LG is used in excess.

In another embodiment of the invention, the compounds of the formula I, wherein $R^{3a}$ together with $R^{3b}$ form a moiety Z-Alk-S with Z being O or S, can be prepared according to the reaction depicted in scheme 2:

Scheme 2:

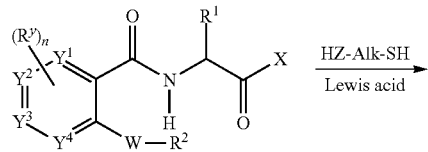

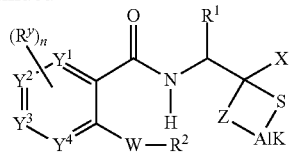

In scheme 2, the variables n, $R^y$, $Y^1$, $Y^2$, $Y^3$, $Y^4$, $R^1$, $R^2$, W, X and Alk are as defined herein. Z is oxygen or sulfur. The lewis acid is preferably $BF_3$ or a $BF_3$ ether complex such as $BF_3*O(C_2H_5)_2$. The reaction can be performed by analogy to the reactions described in Journal of Combinatorial Chemistry (2004), 6(2), 181-195, Journal of Medicinal Chemistry (1993), 36(22), 3472-80 or Bioorganic & Medicinal Chemistry, 2007, 15, 931-938

The starting compounds of the formula II have been described in PCT/EP2007/064617 or they can be prepared by analogy to the schemes and methods described in WO 99/54305, pp. 6-10. An important access to compounds of the formula II is depicted in scheme 3.

Scheme 3:

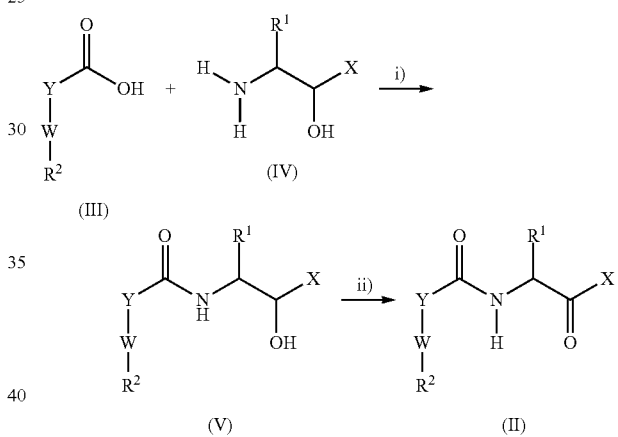

In Scheme 3 and in the following schemes, $R^1$, $R^2$, W, and X exhibit the aforementioned meanings. Y represents a group

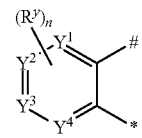

wherein n, $R^y$, $Y^1$, $Y^2$, $Y^3$ and $Y^4$ are as defined herein and wherein * indicates the point of attachment to W, while # indicates the point of attachment to the carbonyl group.

In a first step i), a carboxylic acid III is converted by reaction with an amino alcohol IV into a corresponding hydroxy amide V. In this connection, conventional peptide coupling methods are ordinarily used, as are described for example in R. C. Larock, Comprehensive Organic Transformations, VCH Publisher, 1989, pages 972-976, or in Houben-Weyl, Methoden der organischen Chemie, $4^{th}$ edition, $E^5$, Chap. V. It may be advantageous firstly to activate the carboxylic acid III. For this purpose, for example, the carboxylic acid III is reacted with a carbodiimide such as dicyclohexylcarbodiimide (DCC) or 1-ethyl-3-(3-dimethylaminopropyl)

carbodiimide (EDC) in the presence of hydroxybenzotriazole (HOBt), nitrophenol, pentafluorophenol, 2,4,5-trichlorophenol or N-hydroxysuccinimide, to obtain an activated ester IIa. It may further be advantageous to prepare the activated ester IIIa in the presence of a base, for example a tertiary amine. The activated ester IIIa is subsequently reacted with the amino alcohol of the formula IV or its hydrohalide salt to give the hydroxy amide V. The reaction normally takes place in anhydrous inert solvents such as chlorinated hydrocarbons, e.g. dichloromethane or dichloroethane, ethers, e.g. tetrahydrofuran or 1,4-dioxane or carboxamides, e.g. N,N-dimethylformamide, N,N-dimethylacetamide or N-methylpyrrolidone. Step i) is ordinarily carried out at temperatures in the range from −20° C. to +25° C.

Subsequently, in a second step ii), the hydroxy amide compound V is oxidized to the carboxamide compound II. Various conventional oxidation reactions are suitable for this (see R. C. Larock, Comprehensive Organic Transformations, VCH Publisher, 1989, page 604 et seq.) such as, for example, Swern oxidation and Swern analogous oxidations (T. T. Tidwell, Synthesis 1990, pp. 857-870) or Pfitzner-Moffatt oxidation. Suitable oxidizing agents are dimethyl sulfoxide (DMSO) in combination with dicyclohexylcarbodiimide or 1-ethyl-3-(3-dimethylaminopropyl)carbodiimide, dimethyl sulfoxide in combination with the pyridine-$SO_3$ complex or dimethyl sulfoxide in combination with oxalyl chloride, sodium hypochloride/TEMPO (S. L. Harbenson et al., J. MED: Chem. 1994, 37, 2918-2929) or the Dess-Martin reagent (J. Org. Chem. 1983, 48, 4155). Depending on the oxidizing agent used, the oxidation of the hydroxy amide compound V takes place at temperatures of from −50 to +25° C.

Compounds of the formula II in which X is —C(O)N($R^{x4}$)—($C_1$-$C_6$-alkylene)-$NR^{x2}R^{x3}$ or is —C(O)N($R^{x4}$) $NR^{x2}R^{x3}$ in which $R^{x2}$, $R^{x3}$ and $R^{x4}$ have the aforementioned meanings can additionally be prepared by reacting compounds of the formula II in which X is COOH with hydrazine compounds of the formula NH($R^{x4}$) $NR^{x2}R^{x3}$ or diamines of the formula NH($R^{x4}$)—($C_1$-$C_6$-alkylene)-$NR^{x2}R^{x3}$. The reaction can be carried out in analogy to step i) in Scheme 1.

The amino alcohols IV can be obtained by purchase or can be prepared by processes disclosed in the literature (for amino hydroxy carboxylic acid derivatives, see, for example, S. L. Harbenson et al., J. Med. Chem. 1994, 37, 2918-2929 or J. P. Burkhardt et al., Tetrahedron Lett. 1988, 29, 3433-3436) or in analogy to the processes described in the preparation examples.

The carboxylic acid III can be prepared by hydrolyzing the carboxylic ester VI with acids or bases under generally customary conditions. The hydrolysis preferably takes place with bases such as alkali metal or alkaline earth metal hydroxides, for example lithium hydroxide, sodium hydroxide or potassium hydroxide in aqueous medium or in a mixture of water and organic solvents, e.g. alcohols such as methanol or ethanol, ethers such as tetrahydrofuran or dioxane, at room temperature or elevated temperature such as 25-100° C.

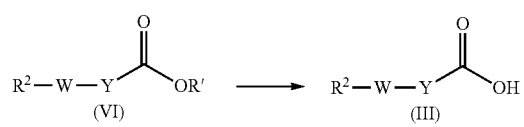

In formulae III and VI, $R^2$, W and Y have the aforementioned meanings. In formula VI, $R^{xa}$ is alkyl, preferably $C_1$-$C_6$-alkyl.

The carboxylic ester of the formula VI can advantageously be obtained by reacting the carboxylic ester of the general formula VII with an imidazole or pyrazole compound VIII, see Scheme 4.

Scheme 4:

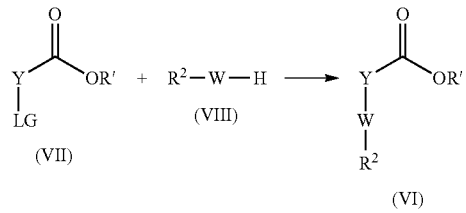

In scheme 4, LG represents a nucleophilically displaceable leaving group. Examples of suitable nucleophilically displaceable leaving groups are halogen, e.g. chlorine or bromine, or tosylate. $R^{xa}$ is alkyl, preferably $C_1$-$C_6$-alkyl. $R^2$, Y and W have the aforementioned meanings.

As shown in Scheme 4, an ester VII is reacted with an appropriate imidazole or pyrazole compound of the formula VIII. The reaction is ordinarily carried out under conventional conditions in the presence of a base in an inert solvent at elevated temperature. It may be advantageous where appropriate to carry out the reaction in the presence of catalytically active amounts of a transition metal, in particular of a metal of group 10 or 11 in the periodic table.

The reaction is preferably carried out at elevated temperature without diluent or in an inert solvent such as an ether, e.g. tetrahydrofuran or dioxane, carboxamides such as N,N-dimethylformamide, N,N-dimethylacetamide or N-methylpyrrolidone, or an aromatic hydrocarbon such as benzene, toluene or o-, m- or p-xylene. The reaction takes place in the presence of inorganic or organic bases and of a crown ether. Suitable inorganic bases are alkali metal or alkaline earth metal amides such as sodium amide, alkali metal or alkaline earth metal carbonates such as potassium carbonate or cesium carbonate or alkali metal hydrides such as sodium hydride. Suitable organic bases are tertiary amines, such as, for example, trimethylamine or triethylamine. A suitable crown ether is 18-crown-6. A Cu(I) salt such as, for example, CuI, CuCN, $Cu_2O$ is added where appropriate as catalyst (see, for example, U.S. Pat. No. 4,826,835 and WO 88/00468).

The reaction of the carboxylic ester VII with the pyrazole or imidazole compound VIII may also take place by transition metal-catalyzed N-arylation as described for example by H. J. Cristeau et al., Eur. J. Org. Chem. 2004, pp. 695-709, and S. L. Buchwald et al.; J. Org. Chem. 2004, 69, pages 5578-5587. The reaction frequently takes place in the presence of catalytically active amounts of a metal of group 10 in the periodic table, especially in the presence of a nickel(II) compound, Ni(0) compound, Pd(II) compound or Pd(0) compound. An example of a suitable method is the Buchwald cross-coupling.

The Buchwald cross-coupling normally takes place in the presence of a phosphorus-containing ligand, especially of a monodentate or bidentate phosphine ligand. Preferred ligands on the palladium are bulky, monodentate or bidentate phosphines such as triphenylphosphine, tri(o-tolyl)phosphine, tri(cyclohexyl)phosphine, BINAP (2,2'-bis-(diphenylphosphino)-1,1'-binaphthyl) or the Buchwald phosphines. The ligand may be present in the palladium compound or be added separately. Suitable palladium compounds include tris (dibenzylideneacetone)dipalladium(0), palladium(II) bis(o- tolyl)phosphine chloride and palladium(11) acetate. The Buchwald cross-coupling normally takes place in an organic solvent. Suitable organic solvents are aromatic hydrocarbons such as benzene or toluene, halogenated aromatic hydrocarbons such as chlorobenzene, halogenated hydrocarbons such as dichloromethane, trichloromethane, dichloroethane, ethers such as tetrahydrofuran, dioxane, ethylene glycol dimethyl ether, methyl tert-butyl ether, or amides such as dimethylformamide or N-methylpyrrolidone, and mixtures thereof. The Buchwald coupling reaction can be carried out under normal conditions or with use of microwaves.

The imidazole or pyrazole compounds VIII can be purchased or can be prepared by conventional methods, which are briefly outlined below, from precursors which can be obtained by purchase.

A general overview of the preparation of imidazoles is to be found in W. M. Menge, Pharmacochemistry Library 1998, 30, pages 145-158. The imidazole compounds VII used are particularly advantageously prepared by the method described by Bredereck et al. (Chem. Ber. 1953, 86, pages 88-96) in which alpha-halo or alpha-hydroxy ketones are reacted with formamide—ordinarily with heating—to give the imidazoles VII.

General methods for preparing pyrazoles of the general formula VIII are described for example in R. Fusco in "The Chemistry of Heterocyclic Compounds: Pyrazoles, Pyrazolines, Pyrazolidines, Indazoles and Condensed Rings", Wiley, R. H., editor; Wiley: New York, 1967; Vol. 22, pages 1-174; or J. Elguero, in "Comprehensive Heterocyclic Chemistry"; Potts, K. T., Ed.; Pergamon: Oxford 1984; Vol. 5, pages 291-298. One of the most commonly used methods is cyclocondensation of 1,3-dicarbonyl compounds or correspondingly reactive analogs with hydrazine or substituted hydrazine derivatives.

3-Aryl- or 3-hetaryl-substituted pyrazoles VIII are particularly advantageously prepared by reacting 1-aryl- or 1-hetaryl-3-dimethylamino-2-propene compounds with hydrazine in analogy to the processes described for example in M. A. Halcrow et al.; J. Chem. Soc. Dalton Trans. 1997, pages 4025-4035. The 1-aryl- or 1-hetaryl-3-dimethylamino-2-propenes required as starting material can easily be prepared by condensing the analogous aromatic acetyl compounds with N,N-dimethylformamide dimethyl acetal (or analogously using the corresponding diethyl acetal). The reaction is normally carried out without diluent or in an inert solvent such as, for example, dimethylformamide or toluene, at elevated temperature. It is particularly advantageous to introduce the activation energy necessary for the reaction into the reaction mixture also by means of microwaves and to carry out the reaction under elevated pressure as described in A. K. Pleier, Synthesis 2001, 1, pages 55-62.

Analogous 4-substituted pyrazoles of the general formula VIII are prepared for example starting from aryl- or hetarylacetic acids which are converted by means of the Vilsmeier reagent into the corresponding gamma-dimethylamino-2-propenals, with subsequent cyclization with hydrazine, see, for example, U.S. Pat. No. 4,888,352.

A further general possibility for preparing substituted pyrazoles of the formula VIII is the Suzuki coupling of appropriate pyrazoleboronic acids or pyrazoleboronic esters as described for example in: N. Zhe et al.; J. Med. Chem. 2005, 48 (5), pages 1569-1609; Young et al.; J. Med. Chem. 2004, 47 (6), pp. 1547-1552; C. Slee et al.; Bioorg. Med. Chem. Lett. 2001, 9, pages 3243-3253. An appropriate alternative is also Stille coupling of halogenated pyrazole derivatives with appropriate tin organyls as described for example by J. Eluguero et al.; Synthesis 1997, 5, pp. 563-566.

The preparation of 1,4-dihydrobenzopyranopyrazoles can be performed according to the methods described by Chandrasekhar, S. et al.; Tetrahedron Letters 2001, 42(37), 6599-6601.

The compounds of the present invention can also be prepared by analogy to the method depicted in scheme 5, which is closely related to the method depicted in scheme 3:

Scheme 5:

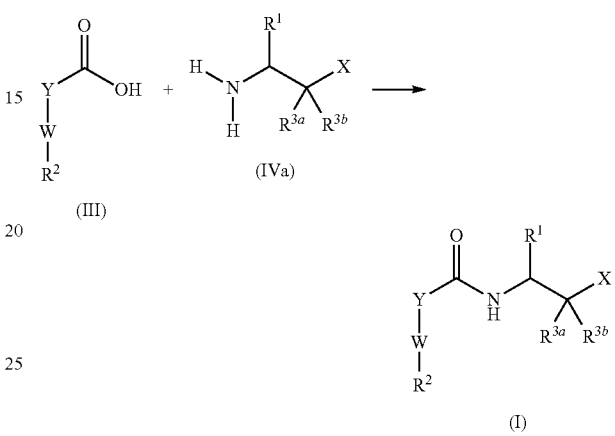

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

If individual compounds I are not obtainable by the routes described above, they can be prepared by derivatization of other compounds I.

The compounds of the formula I, their salts and tautomers themselves are poor calpain inhibitors. Likewise, the compounds do not inhibit other cysteine proteases such as cathepsin B, cathepsin K, cathepsin L or cathepsin S. Generally, the Ki value for inhibition of calpain and other cystein proteases is >10 µm.

The compounds of the formula I are unexpectedly stable with regard to conversion into the compounds of formula II under in vitro conditions. For example, in aqueous acidic environment at pH 1 in dioxane/water no major formation of the corresponding compound of the formula II could be observed even after one week at 37° C.

However, the compounds of the formula II, into which the compounds of the formula I are metabolized in vivo, exhibit extremely low Ki values in relation to the inhibition of calpain and thus permit efficient inhibition of calpain, especially calpain I, at low serum levels. The compounds of the formula II (and likewise their salts and tautomers) ordinarily exhibit Ki values in relation to the inhibition of calpain in vitro of <500 nM, in particular <100 nM and specifically ≤40 nM. The compounds of the invention are therefore particularly suitable for the treatment of disorders associated with an elevated calpain activity.

In addition, the compounds of the formula II are selective calpain inhibitors, i.e. the inhibition of other cysteine proteases such as cathepsin B, cathepsin K, cathepsin L or cathepsin S takes place only at concentrations which are distinctly higher than the concentrations necessary for inhibition of calpain. Accordingly, the compounds of the invention ought to show distinctly fewer side effects than the prior art compounds which are comparatively unselective in relation to inhibition of calpain and likewise inhibit other cysteine proteases.

Preferred compounds according to the invention are those which are metabolized into compounds of the formula II, which have a selectivity in relation to inhibition of cathepsin B, expressed in the form of the ratio of the Ki for inhibition of cathepsin B to the Ki for inhibition of calpain of ≥10, in particular ≥30.

Preferred compounds according to the invention are those which are metabolized into compounds of the formula II, which have a selectivity in relation to inhibition of cathepsin K, expressed in the form of the ratio of the Ki for inhibition of cathepsin K to the Ki for inhibition of calpain of ≥10, in particular ≥30.

Preferred compounds according to the invention are those which are metabolized into compounds of the formula II, which a selectivity in relation to inhibition of cathepsin L, expressed in the form of the ratio of the Ki for inhibition of cathepsin L to the Ki for inhibition of calpain of ≥30, in particular ≥50.

Preferred compounds according to the invention are those which are metabolized into compounds of the formula II, which have a selectivity in relation to inhibition of cathepsin S, expressed in the form of the ratio of the Ki for inhibition of cathepsin S to the Ki for inhibition of calpain of ≥50, in particular ≥100.

Owing to the capability of the compounds of the formula I to be metabolized into compounds of the formula II, which show a strong inhibitory effect on calpain and a high selectivity for calpain by comparison with other cysteine proteases, the compounds of the formula I, their tautomers and their pharmaceutically suitable salts are particularly suitable for the treatment of a disorder or of a condition which is associated with an elevated calpain activity as are described for example in the prior art cited at the outset.

Disorders associated with an elevated calpain activity are in particular neurodegenerative disorders, especially those neurodegenerative disorders occurring as a result of a chronic brain supply deficit, of an ischemia (stroke) or of a trauma such as brain trauma, and the neurodegenerative disorders Alzheimer's disease, Parkinson's disease, amyotrophic lateral sclerosis and Huntington's disease, also multiple sclerosis and the damage to the nervous system associated therewith, especially damage to the optic nerve (optic neuritis) and the nerves which control the movement of the eye. Accordingly, preferred embodiments of the invention relate to the treatment of neurodegenerative disorders, especially of the aforementioned neurodegenerative disorders in humans, and to the use of the compounds of the invention of the formula I, their tautomers and their pharmaceutically suitable salts for the manufacture of a medicament for the treatment of these disorders.

Disorders associated with an elevated calpain activity also include epilepsy. Accordingly, preferred embodiments of the invention relate to the treatment of epilepsy in humans, and to the use of the compounds of the invention of the formula I, their tautomers and their pharmaceutically suitable salts for the manufacture of a medicament for the treatment of epilepsy.

The disorders or conditions associated with an elevated calpain activity also include pain and painful conditions. Accordingly, preferred embodiments of the invention relate to the treatment of pain and painful conditions in mammals, especially in humans, and to the use of the compounds of the invention of the formula I, their tautomers and their pharmaceutically suitable salts for the manufacture of a medicament for the treatment of pain and painful conditions.

The disorders or conditions associated with an elevated calpain activity also include damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty. Accordingly, preferred embodiments of the invention relate to the treatment of diseases or conditions associated with damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty in mammals, especially in humans, and to the use of the compounds of the invention of the formula I, their tautomers, prodrugs and their pharmaceutically suitable salts for the manufacture of a medicament for the treatment of these disorders.

It has further emerged that inhibition of calpain brings about cytotoxic effects on tumor cells. Accordingly, the compounds of the invention are suitable for the chemotherapy of tumors and metastasis thereof. Preferred embodiments of the invention therefore relate to the use of the compounds of the invention of the formula I, their tautomers and their pharmaceutically suitable salts in the therapy of tumors and metastases, and to their use for the manufacture of a medicament for the therapy of tumors and metastases.

It has further been found that various impairments associated with an HIV disorder, especially nerve damage (HIV-induced neurotoxicity), are mediated by calpain and therefore inhibition of calpain allows such impairments to be treated or alleviated. Accordingly, the compounds of the invention of the formula I, their tautomers, their prodrugs and their pharmaceutically suitable salts are suitable for the treatment of HIV patients. Preferred embodiments of the invention therefore relate to the use of the compounds of the invention of the formula I, their tautomers and their pharmaceutically suitable salts for the treatment of HIV-infected patients, especially the treatment of those impairments caused by an HIV-induced neurotoxicity, and to their use for the manufacture of a medicament for the treatment of HIV patients.

It has further been found that the release of interleukin-I, TNF or beta-amyloid peptides (Aβ or Aβ-peptides) can be reduced or completely inhibited by calpain inhibitors. Accordingly, impairments or disorders associated with an elevated interleukin-I, TNF or Aβ level can be treated by using the compounds of the invention of the formula I, their tautomers and their pharmaceutically suitable salts. Preferred embodiments of the invention therefore relate to the use of the compounds of the invention of the formula I, their tautomers, their produgs and their pharmaceutically acceptable salts for the treatment of impairments or disorders associated with an elevated interleukin-I, TNF or Aβ level such as rheumatism, rheumatoid arthritis and to their use for the manufacture of a medicament for the treatment of such impairments or disorders.

The present invention also relates to pharmaceutical compositions (i.e. medicaments) which comprise at least one compound of the invention of the formula I or a tautomer or a pharmaceutically suitable salt thereof and, where appropriate, one or more suitable drug carriers.

These drug carriers are chosen according to the pharmaceutical form and the desired mode of administration.

The compounds of the invention of the general formula I, their tautomers and the pharmaceutically suitable salts of these compounds can be used to manufacture pharmaceutical compositions for oral, sublingual, subcutaneous, intramuscular, intravenous, topical, intratracheal, intranasal, transdermal or rectal administration, and be administered to animals or humans in unit dose forms, mixed with conventional pharmaceutical carriers, for the prophylaxis or treatment of the above impairments or diseases.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active basic ingredient may vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered 1 to 5 times a day, so that a daily dose of from 0.5 to 25 000 mg, preferably 1 to 5000 mg, is administered.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their tautomers or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

The following examples illustrate the invention without restricting it. Depending on the management of the reaction and working up, the compounds of the general formula I result as mixtures of carbonyl form and the corresponding hydrates. Conversion into the pure carbonyl compounds generally takes place by treating the substances with HCl in an inert solvent.

I. PREPARATION EXAMPLES

The starting material of example 1, namely N-[3-amino-1-(4-fluorobenzyl)-2,3-dioxopropyl]-2-[3-(2,4-dichlorophenyl)-1H-pyrazol-1-yl]nicotinamide (hereinafter compound II-1) corresponds to example 114 of PCT/EP2007/064617.

The starting material of example 2, namely N-(3-Amino-1-benzyl-2,3-dioxopropyl)-2-{3-[3-(trifluoromethyl)phenyl]-1H-pyrazol-1-yl}nicotinamide (hereinafter compound II-2) corresponds to example 83 of PCT/EP2007/064617.

The starting material of example 3, namely N-(3-amino-1-benzyl-2,3-dioxopropyl)-2-[3-(4-fluorophenyl)-1H-pyrazol-1-yl]nicotinamide (hereinafter compound II-3) corresponds to example 38 of PCT/EP2007/064617.

Example 1

N-[1-[2-(Aminocarbonyl)-1,3-dioxolan-2-yl]-2-(4-fluorophenyl)ethyl]-2-[3-(2,4-dichlorophenyl)-1H-pyrazol-1-yl]nicotinamide (compound I-1)

N-[3-amino-1-(4-fluorobenzyl)-2,3-dioxopropyl]-2-[3-(2,4-dichlorophenyl)-1H-pyrazol-1-yl]nicotinamide (0.09 g, 0.171 mmol) was dissolved in dimethylformamide (DMF, 1.7 ml) forming a slight yellow solution. Then, 2-bromoethanol (0.059 ml, 0.838 mmol) and 1,8-diazabicyclo[5.4.0]undec-7-ene (DBU, 0.090 ml, 0.598 mmol) were added with stirring at room temperature. Stirring was continued over night. Water was added to reaction mixture resulting in precipitation of the desired product. The suspension was stirred for 30 min. at 0-5° C. The suspension was filtered under reduced pressure, the precipitate washed three times with ice cold water, and subsequently dried at 40° C. under reduced pressure. The remaining residue (85 mg) was treated with a dichloromethane/methanol mixture (97:3 v/v) and the resulting suspension was stirred at room temperature for 30 min. The precipitate was filtered under reduced pressure. washed with few amounts of dichloromethane and subsequently dried at 40° C. under reduced pressure resulting in 19 mg off-white powder. An additional amount of pure desired product could be obtained by column chromatography of the evaporated filtrate.

ESI-MS [M+H+]=570.1/572.1

$^1$H-NMR (500 MHz DMSO) δ ppm: 8.55 (s, 1H), 8.34 (d, 1H), 8.18 (s, 1H), 7.77 (s, 1H), 7.61 (dd, 2H), 7.30-7.55 (m, 4H), 7.15 (s, 2H), 6.85-7.00 (m, 3H), 4.76 (s br, 1H), 3.80-3.95 (m, 3H), 3.71 (s br, 1H), 2.70-2.85 (m, 1H), 2.55-2.70 (m, 1H), Example 2

N-{1-[2-(Aminocarbonyl)-1,3-dioxolan-2-yl]-2-phenylethyl}-2-{3-[3-(trifluoromethyl)phenyl]-1H-pyrazol-1-yl}nicotinamide (compound I-2)

The title compound was prepared according to the procedure outlined in Example 1, using N-(3-amino-1-benzyl-2,3- dioxopropyl)-2-{3-[3-(trifluoromethyl)phenyl]-1H-pyrazol-1-yl}nicotinamide as a starting material.

ESI-MS [M+H+]=552.2

$^1$H-NMR (400 MHz DMSO) δ ppm: 8.54 (s br, 1H), 8.35 (s br, 1H), 8.13 (s br, 2H), 7.99 (s br, 1H), 7.30-7.70 (m, 6H), 6.95-7.30 (m, 6H), 4.80 (s br, 1H), 3.65-4.00 (m, 4H), 2.55-2.95 (m, 2H) br: broad

Example 3

N-{1-[2-(Aminocarbonyl)-1,3-dioxolan-2-yl]-2-phenylethyl}-2-[3-(4-fluorophenyl)-1H-pyrazol-1-yl]nicotinamide (compound I-3)

The title compound was prepared according to the procedure outlined in Example 1, using N-(3-amino-1-benzyl-2,3-dioxopropyl)-2-[3-(4-fluorophenyl)-1H-pyrazol-1-yl]nicotinamide as starting material.

ESI-MS [M+H+]=502.2

$^1$H-NMR (400 MHz DMSO) δ ppm: 8.51 (d, 1H), 8.33 (d, 1H), 8.02 (d, 1H), 7.88 (dd, 2H), 7.51 (s, 1H), 7.46 (d, 2H), 7.38-7.43 (m, 2H), 7.13-7.25 (m, 7H), 6.87 (d, 1H), 4.79-4.86 (m, 1H), 3.78-3.94 (m, 3H), 3.68-3.76 (m, 1H), 2.83 (dd, 1H), 2.63 (dd, 1H).

The compounds of examples 1 to 3 were unexpectedly stable in aqueous acidic environment. Even after one week at 37° C. at pH 1 in dioxane/water no major formation of the corresponding compound of the formula II could be observed as determined by HPLC MSD.

Example 4

N-[1-(2-Carbamoyl-[1,3]dioxolan-2-yl)-2-phenylethyl]-2-(4-phenyl-imidazol-1-yl)-nicotinamide The title compound can be prepared according to the procedure outlined in Example 1 starting from N-(3-amino-1-benzyl-2,3-dioxopropyl)-2-(4-phenyl-1H-imidazol-1-yl)nicotinamide (example 1 in WO2008/080969).

Example 5

N-[1-(2-Carbamoyl-[1,3]dioxolan-2-yl)-pentyl]-2-(4-phenyl-imidazol-1-yl)-nicotinamide The title compound can be prepared according to the procedure outlined in Example 1 starting from N-{1-[amino (oxo)acetyl]pentyl}-2-(4-phenyl-1H-imidazol-1-yl)nicotinamide (example 2 in WO2008/080969).

Example 6

N-[1-(2-Carbamoyl-[1,3]dioxolan-2-yl)-pentyl]-2-(4-phenyl-pyrazol-1-yl)-nicotinamide The title compound can be prepared according to the procedure outlined in Example 1 starting from N-{1[amino(oxo)acetyl]pentyl}-2-(4-phenyl-1H-pyrazol-1-yl)nicotinamide (example 3 in WO2008/080969).

Example 7

N-[1-(2-Carbamoyl-[1,3]dioxolan-2-yl)-2-phenylethyl]-2-(4-phenyl-pyrazol-1-yl)-nicotinamide The title compound can be prepared according to the procedure outlined in Example 1 starting from N-(3-amino-1-benzyl-2,3-dioxopropyl)-2-(4-phenyl-1H-pyrazol-1-yl)nicotinamide (example 4 in WO2008/080969).

Example 8

N-[1-(2-Carbamoyl-[1,3]dioxolan-2-yl)-2-phenylethyl]-2-(3-phenyl-pyrazol-1-yl)-nicotinamide The title compound can be prepared according to the procedure outlined in Example 1 starting from N-(3-amino-1-benzyl-2,3-dioxopropyl)-2-(3-phenyl-1H-pyrazol-1-yl)nicotinamide (example 5 in WO2008/080969).

Example 9

N-[1-(2-Carbamoyl-[1,3]dioxolan-2-yl)-pentyl]-2-(3-phenyl-pyrazol-1-yl)-nicotinamide The title compound can be prepared according to the procedure outlined in Example 1 starting from N-{1-[amino (oxo)acetyl]pentyl}-2-(3-phenyl-1H-pyrazol-1-yl)nicotinamide (example 6 in WO2008/080969).

Example 10

N-[1-(2-Carbamoyl-[1,3]dioxolan-2-yl)-2-phenylethyl]-2-[4-(4-fluoro-phenyl)-imidazol-1-yl]-nicotinamide The title compound can be prepared according to the procedure outlined in Example 1 starting from N-(3-amino-1-benzyl-2,3-dioxopropyl)-2-[4-(4-fluorophenyl)-1H-imidazol-1-yl]nicotinamide (example 8 in WO2008/080969).

Example 11

N-[1-(2-Carbamoyl-[1,3]dioxolan-2-yl)-2-phenylethyl]-2-[4-(4-chloro-phenyl)-imidazol-1-yl]-nicotinamide The title compound can be prepared according to the procedure outlined in Example 1 starting from N-(3-amino-1-benzyl-2,3-dioxopropyl)-2-[4-(4-chlorophenyl)-1H-imidazol-1-yl]nicotinamide (example 9 in WO2008/080969).

Example 12

N-[1-(2-Carbamoyl-[1,3]dioxolan-2-yl)-pentyl]-2-[4-(4-chloro-phenyl)-imidazol-1-yl]-nicotinamide The title compound can be prepared according to the procedure outlined in Example 1 starting from N-{1-[amino (oxo)acetyl]pentyl}-2-[4-(4-chlorophenyl)-1H-imidazol-1-yl]nicotinamide (example 10 in WO2008/080969).

Example 13

N-[1-(2-Carbamoyl-[1,3]dioxolan-2-yl)-pentyl]-2-[4-(4-fluoro-phenyl)-imidazol-1-yl]-nicotinamide The title compound can be prepared according to the procedure outlined in Example 1 starting from N-{1-[amino (oxo)acetyl]pentyl}-2-[4-(4-fluorophenyl)-1H-imidazol-1-yl]nicotinamide (example 11 in WO2008/080969).

Example 14

N-[1-(2-Carbamoyl-[1,3]dioxolan-2-yl)-pentyl]-2-[4-(4-methoxy-phenyl)-imidazol-1-yl]-nicotinamide The title compound can be prepared according to the procedure outlined in Example 1 starting from N-{1[amino(oxo)acetyl]pentyl}-2-[4-(4-methoxyphenyl)-1H-imidazol-1-yl]nicotinamide (example 12 in WO2008/080969).

Example 15

N-[1-(2-Carbamoyl-[1,3]dioxolan-2-yl)-2-phenyl-ethyl]-2-[4-(4-methoxy-phenyl)-imidazol-1-yl]-nicotinamide The title compound can be prepared according to the procedure outlined in Example 1 starting from N-(3-amino-1-benzyl-2,3-dioxopropyl)-2-[4-(4-methoxyphenyl)-1H-imidazol-1-yl]nicotinamide hydrochloride (example 13 in WO2008/080969).

Example 16

N-[1-(2-Carbamoyl-[1,3]dioxolan-2-yl)-2-phenyl-ethyl]-2-[4-(4-morpholin-4-yl-phenyl)-imidazol-1-yl]-nicotinamide The title compound can be prepared according to the procedure outlined in Example 1 starting from N-(3-amino-1-benzyl-2,3-dioxopropyl)-2-[4-(4-morpholin-4-ylphenyl)-1H-imidazol-1-yl]nicotinamide (example 14 in WO2008/080969).

Example 17

N-[1-(2-Carbamoyl-[1,3]dioxolan-2-yl)-pentyl]-2-[4-(4-morpholin-4-yl-phenyl)-imidazol-1-yl]-nicotinamide The title compound can be prepared according to the procedure outlined in Example 1 starting from N-{1-[amino(oxo)acetyl]pentyl}-2-[4-(4-morpholin-4-ylphenyl)-1H-imidazol-1-yl]nicotinamide hydrochloride (example 15 in WO2008/080969).

Example 18

N-[1-(2-Carbamoyl-[1,3]dioxolan-2-yl)-2-phenyl-ethyl]-2-[4-(4-diethylamino-phenyl)-imidazol-1-yl]-nicotinamide The title compound can be prepared according to the procedure outlined in Example 1 starting from N-(3-amino-1-benzyl-2,3-dioxopropyl)-2-{4-[4-(diethylamino)phenyl]-1H-imidazol-1-yl}nicotinamide hydrochloride (example 16 in WO2008/080969).

Example 19

N-[1-(2-Carbamoyl-[1,3]dioxolan-2-yl)-pentyl]-2-[4-(4-trifluoromethyl-phenyl)-imidazol-1-yl]-nicotinamide The title compound can be prepared according to the procedure outlined in Example 1 starting from N-{1-[amino(oxo)acetyl]pentyl}-2-{4-[4-(trifluoromethyl)phenyl]-1H-imidazol-1-yl}nicotinamide hydrochloride (example 17 in WO2008/080969).

Example 20

N-[1-(2-Carbamoyl-[1,3]dioxolan-2-yl)-2-phenyl-ethyl]-2-[4-(4-trifluoromethyl-phenyl)-imidazol-1-yl]nicotinamide The title compound can be prepared according to the procedure outlined in Example 1 starting from N-(3-amino-1-benzyl-2,3-dioxopropyl)-2-{4-[4-(trifluoromethyl)phenyl]-1H-imidazol-1-yl}nicotinamide hydrochloride (example 18 in WO2008/080969).

Example 21

N-[1-(2-Carbamoyl-[1,3]dioxolan-2-yl)-2-phenyl-ethyl]-2-[4-(2-chloro-phenyl)-imidazol-1-yl]-nicotinamide The title compound can be prepared according to the procedure outlined in Example 1 starting from N-(3-amino-1-benzyl-2,3-dioxopropyl)-2-[4-(2-chlorophenyl)-1H-imidazol-1-yl]nicotinamide hydrochloride (example 19 in WO2008/080969).

Example 22

N-[1-(2-Carbamoyl-[1,3]dioxolan-2-yl)-pentyl]-2-[4-(2-chloro-phenyl)-imidazol-1-yl]-nicotinamide The title compound can be prepared according to the procedure outlined in Example 1 starting from N-{1-[amino(oxo)acetyl]pentyl}-2-[4-(2-chlorophenyl)-1H-imidazol-1-yl]nicotinamide hydrochloride (example 20 in WO2008/080969).

Example 23

N-[1-(2-Carbamoyl-[1,3]dioxolan-2-yl)-pentyl]-2-[4-(3-chloro-phenyl)-imidazol-1-yl]-nicotinamide The title compound can be prepared according to the procedure outlined in Example 1 starting from N-(3-amino-1-benzyl-2,3-dioxopropyl)-2-[4-(3-chlorophenyl)-1H-imidazol-1-yl]nicotinamide (example 21 in WO2008/080969).

Example 24

N-[1-(2-Carbamoyl-[1,3]dioxolan-2-yl)-2-phenyl-ethyl]-2-[4-(3-chloro-phenyl)-imidazol-1-yl]nicotinamide The title compound can be prepared according to the procedure outlined in Example 1 starting from N-(3-amino-1-benzyl-2,3-dioxopropyl)-2-[4-(3-chlorophenyl)-1H-imidazol-1-yl]nicotinamide (example 22 in WO2008/080969).

Example 25

N-[1-(2-Carbamoyl-[1,3]dioxolan-2-yl)-2-phenyl-ethyl]-5-chloro-2-(4-phenyl-imidazol-1-yl)-nicotinamide The title compound can be prepared according to the procedure outlined in Example 1 starting from N-(3-amino-1- benzyl-2,3-dioxopropyl)-5-chloro-2-(4-phenyl-1H-imidazol-1-yl)nicotinamide hydrochloride (example 23 in WO2008/080969).

Example 26

N-[1-(2-Carbamoyl-[1,3]clioxolan-2-yl)-pentyl]-5-chloro-2-(4-phenyl-imidazol-1-yl)-nicotinamide The title compound can be prepared according to the procedure outlined in Example 1 starting from N-{1[amino(oxo)acetyl]pentyl}-5-chloro-2-(4-phenyl-1H-imidazol-1-yl)nicotinamide hydrochloride (example 24 in WO2008/080969).

Example 27

N-[1-(2-Carbamoyl-[1,3]dioxolan-2-yl)-3-methyl-butyl]-5-chloro-2-(4-phenyl-imidazol-1-yl)-nicotinamide The title compound can be prepared according to the procedure outlined in Example 1 starting from N-{1-[amino(oxo)acetyl]-3-methylbutyl}-5-chloro-2-(4-phenyl-1H-imidazol-1-yl)nicotinamide (example 25 in WO2008/080969).

Example 28

N-[1-(2-Carbamoyl-[1,3]dioxolan-2-yl)-2-phenyl-ethyl]-2-[4-(4-morpholin-4-ylmethyl-phenyl)-imidazol-1-yl]nicotinamide The title compound can be prepared according to the procedure outlined in Example 1 starting from N-(3-amino-1-benzyl-2,3-dioxopropyl)-2-{4-[4-(morpholin-4-ylmethyl)phenyl]-1H-imidazol-1-yl}nicotinamide hydrochloride (example 26 in WO2008/080969).

Example 29

N-[1-(2-Carbamoyl-[1,3]dioxolan-2-yl)-2-phenyl-ethyl]-5-chloro-2-(3-phenyl-pyrazol-1-yl)-nicotinamide The title compound can be prepared according to the procedure outlined in Example 1 starting from N-(3-amino-1-benzyl-2,3-dioxopropyl)-5-chloro-2-(3-phenyl-1H-pyrazol-1-yl)nicotinamide (example 27 in WO2008/080969).

Example 30

N-[1-(2-Carbamoyl-[1,3]dioxolan-2-yl)-pentyl]-5-chloro-2-(3-phenyl-pyrazol-1-yl)-nicotinamide The title compound can be prepared according to the procedure outlined in Example 1 starting from N-{1-[amino(oxo)acetyl]pentyl}-5-chloro-2-(3-phenyl-1H-pyrazol-1-yl)nicotinamide (example 28 in WO2008/080969).

Example 31

N-[1-(2-Carbamoyl-[1,3]dioxolan-2-yl)-2-phenyl-ethyl]-2-[3-(4-morpholin-4-yl-phenyl)-pyrazol-1-yl]-nicotinamide The title compound can be prepared according to the procedure outlined in Example 1 starting from N-(3-amino-1-benzyl-2,3-dioxopropyl)-2-[3-(4-morpholin-4-ylphenyl)-1H-pyrazol-1-yl]nicotinamide hydrochloride (example 29 in WO2008/080969).

Example 32

N-[1-(2-Carbamoyl-[1,3]dioxolan-2-yl)-3-methyl-butyl]-2-(3-phenyl-pyrazol-1-yl)-nicotinamide The title compound can be prepared according to the procedure outlined in Example 1 starting from N-{1-[amino(oxo)acetyl]-3-methylbutyl}-2-(3-phenyl-1H-pyrazol-1-yl)nicotinamide (example 30 in WO2008/080969).

Example 33

N-[1-(2-Carbamoyl-[1,3]dioxolan-2-yl)-2-phenyl-ethyl]-5-chloro-2-[3-(4-morpholin-4-yl-phenyl)-pyrazol-1-yl]nicotinamide The title compound can be prepared according to the procedure outlined in Example 1 starting from N-(3-amino-1-benzyl-2,3-dioxopropyl)-5-chloro-2-[3-(4-morpholin-4-ylphenyl)-1H-pyrazol-1-yl]nicotinamide (example 31 in WO2008/080969).

Example 34

N-[1-(2-Carbamoyl-[1,3]dioxolan-2-yl)-3-methyl-butyl]-5-chloro-2-(3-phenyl-pyrazol-1-yl)-nicotinamide The title compound can be prepared according to the procedure outlined in Example 1 starting from N-{1-[amino(oxo)acetyl]-3-methylbutyl}-5-chloro-2-(3-phenyl-1H-pyrazol-1-yl)nicotinamide (example 32 in WO2008/080969).

Example 35

N-[1-(2-Carbamoyl-[1,3]dioxolan-2-yl)-pentyl]-2-[3-(4-morpholin-4-yl-phenyl)-pyrazol-1-yl]-nicotinamide The title compound can be prepared according to the procedure outlined in Example 1 starting from N-{1[amino(oxo)acetyl]pentyl}-2-[3-(4-morpholin-4-ylphenyl)-1H-pyrazol-1-yl]nicotinamide (example 33 in WO2008/080969).

Example 36

N-[1-(2-Carbamoyl-[1,3]dioxolan-2-yl)-3-methyl-butyl]-2-[3-(4-morpholin-4-yl-phenyl)-1H pyrazol-1-yl]-nicotinamide The title compound can be prepared according to the procedure outlined in Example 1 starting from N-{1[amino(oxo)acetyl]-3-methylbutyl}-2-[3-(4-morpholin-4-ylphenyl)-1H-pyrazol-1-yl]nicotinamide (example 34 in WO2008/080969).

Example 37

N-[1-(2-Carbamoyl-[1,3]dioxolan-2-yl)-2-thiophen-2-yl-ethyl]-2-(3-phenyl-pyrazol-1-yl)-nicotinamide The title compound can be prepared according to the procedure outlined in Example 1 starting from N-[3-amino-2,3- dioxo-1-(2-thienylmethyl)propyl]-2-(3-phenyl-1H-pyrazol-1-yl)pyridine-3-carboxamide (example 40 in WO2008/080969).

Example 38

N-[1-(2-Carbamoyl-[1,3]dioxolan-2-yl)-pentyl]-2-[3-(4-fluoro-phenyl)-pyrazol-1-yl]-nicotinamide The title compound can be prepared according to the procedure outlined in Example 1 starting from N-{1[amino(oxo)acetyl]pentyl}-2-[3-(4-fluorophenyl)-1H-pyrazol-1-yl]nicotinamide (example 41 in WO2008/080969).

Example 39

N-[1-(2-Carbamoyl-[1,3]dioxolan-2-yl)-2-phenyl-ethyl]-2-[3-(4-diethylamino-phenyl)-pyrazol-1-yl]-nicotinamide The title compound can be prepared according to the procedure outlined in Example 1 starting from N-(3-amino-1-benzyl-2,3-dioxopropyl)-2-{3-[4-(diethylamino)phenyl]-1H-pyrazol-1-yl}nicotinamide (example 42 in WO2008/080969).

Example 40

N-[1-(2-Carbamoyl-[1,3]dioxolan-2-yl)-pentyl]-2-[3-(4-diethylaminomethyl-phenyl)-pyrazol-1-yl]-nicotinamide The title compound can be prepared according to the procedure outlined in Example 1 starting from N-{1-[amino(oxo)acetyl]pentyl}-2-(3-[4-{(diethylamino)methyl]phenyl}-1H-pyrazol-1-yl)nicotinamide (example 44 in WO2008/080969).

Example 41

N-[1-(2-Carbamoyl-[1,3]dioxolan-2-yl)-pentyl]-2-[3-(4-morpholin-4-ylmethyl-phenyl)-pyrazol-1-yl]-nicotinamide The title compound can be prepared according to the procedure outlined in Example 1 starting from N-{1[amino(oxo)acetyl]pentyl}-2-{3-[4-(morpholin-4-ylmethyl)phenyl]-1H-pyrazol-1-yl}nicotinamide (example 45 in WO2008/080969).

Example 42

N-[1-(2-Carbamoyl-[1,3]dioxolan-2-yl)-2-phenyl-ethyl]-2-[3-(4-morpholin-4-ylmethyl-phenyl)-pyrazol-1-yl]-nicotinamide The title compound can be prepared according to the procedure outlined in Example 1 starting from N-(3-amino-1-benzyl-2,3-dioxopropyl)-2-{3-[4-(morpholin-4-ylmethyl)phenyl]-1H-pyrazol-1-yl}nicotinamide (example 46 in WO2008/080969).

Example 43

N-[1-(2-Carbamoyl-[1,3]dioxolan-2-yl)-pentyl]-2-[3-(4-diethylamino-phenyl)-pyrazol-1-yl]-nicotinamide The title compound can be prepared according to the procedure outlined in Example 1 starting from N-{1-[amino(oxo)acetyl]pentyl}-2-{3-[4-(diethylamino)phenyl]-1H-pyrazol-1-yl}nicotinamide (example 47 in WO2008/080969).

Example 44

N-[1-(2-Carbamoyl-[1,3]dioxolan-2-yl)-pentyl]-2-[3-(4-methoxy-phenyl)-pyrazol-1-yl]-nicotinamide The title compound can be prepared according to the procedure outlined in Example 1 starting from N-{1[amino(oxo)acetyl]pentyl}-2-[3-(4-methoxyphenyl)-1H-pyrazol-1-yl]nicotinamide (example 49 in WO2008/080969).

Example 45

N-[1-(2-Carbamoyl-[1,3]dioxolan-2-yl)-2-(4-chloro-phenyl)-ethyl]-2-(3-phenyl-pyrazol-1-yl)-nicotinamide The title compound can be prepared according to the procedure outlined in Example 1 starting from N-[3-amino-1-(4-chlorobenzyl)-2,3-dioxopropyl]-2-(3-phenyl-1H-pyrazol-1-yl)nicotinamide (example 50 in WO2008/080969).

Example 46

N-[1-(2-Carbamoyl-[1,3]dioxolan-2-yl)-2-phenyl-ethyl]-5-fluoro-2-(3-phenyl-pyrazol-1-yl)-nicotinamide The title compound can be prepared according to the procedure outlined in Example 1 starting from N-(3-amino-1-benzyl-2,3-dioxopropyl)-5-fluoro-2-(3-phenyl-1H-pyrazol-1-yl)nicotinamide (example 51 in WO2008/080969).

Example 47

N-[1-(2-Carbamoyl-[1,3]dioxolan-2-yl)-2-phenyl-ethyl]-2-[3-(3-morpholin-4-ylmethyl-phenyl)-pyrazol-1-yl]-nicotinamide The title compound can be prepared according to the procedure outlined in Example 1 starting from N-(3-amino-1-benzyl-2,3-dioxopropyl)-2-{3-[3-(morpholin-4-ylmethyl)phenyl]-1H-pyrazol-1-yl}nicotinamide hydrochloride (example 52 in WO2008/080969).

Example 48

N-[1-(2-Carbamoyl-[1,3]dioxolan-2-yl)-2-phenyl-ethyl]-2-[3-(2-chloro-phenyl)-pyrazol-1-yl]-nicotinamide The title compound can be prepared according to the procedure outlined in Example 1 starting from N-(3-amino-1-benzyl-2,3-dioxopropyl)-2-[3-(2-chlorophenyl)-1H-pyrazol-1-yl]nicotinamide (example 54 in WO2008/080969).

Example 49

N-[1-(2-Carbamoyl-[1,3]dioxolan-2-yl)-2-phenyl-ethyl]-2-(3-thiophen-2-yl-pyrazol-1-yl)-nicotinamide The title compound can be prepared according to the procedure outlined in Example 1 starting from N-(3-amino-1- benzyl-2,3-dioxopropyl)-2-[3-(2-thienyl)-1H-pyrazol-1-yl]nicotinamide (example 55 in WO2008/080969).

Example 50

N-[1-(2-Carbamoyl-[1,3]dioxolan-2-yl)-2-thiophen-2-yl-ethyl]-2-[3-(4-fluoro-phenyl)-pyrazol-1-yl]-nicotinamide The title compound can be prepared according to the procedure outlined in Example 1 starting from N-[3-amino-2,3-dioxo-1-(2-thienylmethyl)propyl]-2-[3-(4-fluorophenyl)-1H-pyrazol-1-yl]nicotinamide (example 57 in WO2008/080969).

Example 51

N-[1-(2-Carbamoyl-[1,3]dioxolan-2-yl)-2-phenyl-ethyl]-2-[3-(3-morpholin-4-yl-phenyl)-pyrazol-1-yl]nicotinamide The title compound can be prepared according to the procedure outlined in Example 1 starting from N-(3-amino-1-benzyl-2,3-dioxopropyl)-2-[3-(3-morpholin-4-ylphenyl)-1H-pyrazol-1-yl]nicotinamide (example 58 in WO2008/080969).

Example 52

N-[1-(2-Carbamoyl-[1,3]dioxolan-2-yl)-pentyl]-2-[3-(3-morpholin-4-yl-phenyl)-pyrazol-1-yl]-nicotinamide The title compound can be prepared according to the procedure outlined in Example 1 starting from N-{1[amino(oxo)acetyl]pentyl}-2-[3-(3-morpholin-4-ylphenyl)-1H-pyrazol-1-yl]nicotinamide (example 59 in WO2008/080969).

Example 53

N-[1-(2-Carbamoyl-[1,3]dioxolan-2-yl)-2-phenyl-ethyl]-2-[3-(4-cyano-phenyl)-pyrazol-1-yl]-nicotinamide The title compound can be prepared according to the procedure outlined in Example 1 starting from N-(3-amino-1-benzyl-2,3-dioxopropyl)-2-[3-(4-cyanophenyl)-1H-pyrazol-1-yl]nicotinamide (example 62 in WO2008/080969).

Example 54

N-[1-(2-Carbamoyl-[1,3]dioxolan-2-yl)-2-phenyl-ethyl]-2-(4,5-dihydro-benzo[g]indazol-2-yl)-nicotinamide The title compound can be prepared according to the procedure outlined in Example 1 starting from N-(3-amino-1-benzyl-2,3-dioxopropyl)-2-(4,5-dihydro-2H-benzo[g]indazol-2-yl)nicotinamide (example 63 in WO2008/080969).

Example 55

N-[1-(2-Carbamoyl-[1,3]dioxolan-2-yl)-2-phenyl-ethyl]-2-[3-(4-piperidin-1-yl-phenyl)-pyrazol-1-yl]-nicotinamide The title compound can be prepared according to the procedure outlined in Example 1 starting from N-(3-amino-1-benzyl-2,3-dioxopropyl)-2-[3-(4-piperidin-1-ylphenyl)-1H-pyrazol-1-yl]nicotinamide (example 64 in WO2008/080969).

Example 56

N-[1-(2-Carbamoyl-[1,3]dioxolan-2-yl)-2-cyclohexyl-ethyl]-2-(3-phenyl-pyrazol-1-yl)-nicotinamide The title compound can be prepared according to the procedure outlined in Example 1 starting from N-[3-amino-1-(cyclohexylmethyl)-2,3-dioxopropyl]-2-(3-phenyl-1H-pyrazol-1-yl)nicotinamide (example 66 in WO2008/080969).

Example 57

N-[1-(2-Carbamoyl-[1,3]dioxolan-2-yl)-2-(4-chloro-phenyl)-ethyl]-2-[3-(4-fluoro-phenyl)-pyrazol-1-yl]-nicotinamide The title compound can be prepared according to the procedure outlined in Example 1 starting from N-[3-amino-1-(4-chlorobenzyl)-2,3-dioxopropyl]-2-[3-(4-fluorophenyl)-1H-pyrazol-1-yl]nicotinamide (example 67 in WO2008/080969).

Example 58

N-[1-(2-Carbamoyl-[1,3]dioxolan-2-yl)-2-phenyl-ethyl]-2-[3-(4-pyrrolidin-1-yl-phenyl)-pyrazol-1-yl]-nicotinamide The title compound can be prepared according to the procedure outlined in Example 1 starting from N-(3-amino-1-benzyl-2,3-dioxopropyl)-2-[3-(4-pyrrolidin-1-ylphenyl)-1H-pyrazol-1-yl]nicotinamide (example 69 in WO2008/080969).

Example 59

N-[1-(2-Carbamoyl-[1,3]dioxolan-2-yl)-2-phenyl-ethyl]-2-[3-(3-chloro-phenyl)-pyrazol-1-yl]-nicotinamide The title compound can be prepared according to the procedure outlined in Example 1 starting from N-(3-amino-1-benzyl-2,3-dioxopropyl)-2-[3-(3-chlorophenyl)-1H-pyrazol-1-yl]nicotinamide (example 70 in WO2008/080969).

Example 60

N-[1-(2-Carbamoyl-[1,3]dioxolan-2-yl)-2-phenyl-ethyl]-2-[3-(2-chloro-4-fluoro-phenyl)-pyrazol-1-yl]-nicotinamide The title compound can be prepared according to the procedure outlined in Example 1 starting from N-(3-amino-1-benzyl-2,3-dioxopropyl)-2-[3-(2-chloro-4-fluorophenyl)-1H-pyrazol-1-yl]nicotinamide (example 71 in WO2008/080969).

Example 61

N-[1-(2-Carbamoyl-[1,3]dioxolan-2-yl)-2-phenyl-ethyl]-2-[3-(3-pyrrolidin-1-yl-phenyl)-pyrazol-1-yl]-nicotinamide The title compound can be prepared according to the procedure outlined in Example 1 starting from N-(3-amino-1- benzyl-2,3-dioxopropyl)-2-[3-(3-pyrrolidin-1-ylphenyl)-1H-pyrazol-1-yl]nicotinamide (example 74 in WO2008/080969).

Example 62

N-[1-(2-Carbamoyl-[1,3]dioxolan-2-yl)-2-phenyl-ethyl]-2-[3-(2,3-dihydro-benzofuran-5-yl)-pyrazol-1-yl]-nicotinamide The title compound can be prepared according to the procedure outlined in Example 1 starting from N-(3-amino-1-benzyl-2,3-dioxopropyl)-2-[3-(2,3-dihydro-1-benzofuran-5-yl)-1H-pyrazol-1-yl]nicotinamide (example 75 in WO2008/080969).

Example 63

N-[1-(2-Carbamoyl-[1,3]dioxolan-2-yl)-2-phenyl-ethyl]-2-[3-(2-fluoro-phenyl)-pyrazol-1-yl]-nicotinamide The title compound can be prepared according to the procedure outlined in Example 1 starting from N-(3-amino-1-benzyl-2,3-dioxopropyl)-2-[3-(2-fluorophenyl)-1H-pyrazol-1-yl]nicotinamide (example 76 in WO2008/080969).

Example 64

N-[1-(2-Carbamoyl-[1,3]dioxolan-2-yl)-2-phenyl-ethyl]-2-indazol-1-yl-nicotinamide The title compound can be prepared according to the procedure outlined in Example 1 starting from N-(3-amino-1-benzyl-2,3-dioxopropyl)-2-(1H-indazol-1-yl)nicotinamide (example 77 in WO2008/080969).

Example 65

N-[1-(2-Carbamoyl-[1,3]dioxolan-2-yl)-2-phenyl-ethyl]-2-indazol-2-yl-nicotinamide The title compound can be prepared according to the procedure outlined in Example 1 starting from N-(3-amino-1-benzyl-2,3-dioxopropyl)-2-(2H-indazol-2-yl)nicotinamide (example 78 in WO2008/080969).

Example 66

N-[1-(2-Carbamoyl-[1,3]dioxolan-2-yl)-2-phenyl-ethyl]-2-[3-(2,4-dichloro-phenyl)-pyrazol-1-yl]-nicotinamide The title compound can be prepared according to the procedure outlined in Example 1 starting from N-(3-amino-1-benzyl-2,3-dioxopropyl)-2-[3-(2,4-dichlorophenyl)-1H-pyrazol-1-yl]nicotinamide (example 79 in WO2008/080969).

Example 67

N-[1-(2-Carbamoyl-[1,3]dioxolan-2-yl)-2-(4-methoxy-phenyl)-ethyl]-2-(3-phenyl-pyrazol-1-yl)-nicotinamide The title compound can be prepared according to the procedure outlined in Example 1 starting from N-[3-amino-1-(4-methoxybenzyl)-2,3-dioxopropyl]-2-(3-phenyl-1H-pyrazol-1-yl)nicotinamide (example 80 in WO2008/080969).

Example 68

N-[1-(2-Carbamoyl-[1,3]dioxolan-2-yl)-2-(4-methoxy-phenyl)-ethyl]-2-[3-(4-fluoro-phenyl)-pyrazol-1-yl]-nicotinamide The title compound can be prepared according to the procedure outlined in Example 1 starting from N-[3-amino-1-(4-methoxybenzyl)-2,3-dioxopropyl]-2-[3-(4-fluorophenyl)-1H-pyrazol-1-yl]nicotinamide (example 81 in WO2008/080969).

Example 69

N-[1-(2-Carbamoyl-[1,3]dioxolan-2-yl)-2-phenyl-ethyl]-5-cyano-2-(3-phenyl-pyrazol-1-yl)-nicotinamide The title compound can be prepared according to the procedure outlined in Example 1 starting from N-(3-amino-1-benzyl-2,3-dioxopropyl)-5-cyano-2-(3-phenyl-1H-pyrazol-1-yl)nicotinamide (example 82 in WO2008/080969).

Example 70

N-[1-(2-Carbamoyl-[1,3]dioxolan-2-yl)-2-phenyl-ethyl]-2-(4-methyl-3-phenyl-pyrazol-1-yl)-nicotinamide The title compound can be prepared according to the procedure outlined in Example 1 starting from N-(3-amino-1-benzyl-2,3-dioxopropyl)-2-(4-methyl-3-phenyl-1H-pyrazol-1-yl)nicotinamide (example 84 in WO2008/080969).

Example 71

N-[1-(2-Carbamoyl-[1,3]dioxolan-2-yl)-2-phenyl-ethyl]-2-[3-(2,6-difluoro-phenyl)-pyrazol-1-yl]nicotinamide The title compound can be prepared according to the procedure outlined in Example 1 starting from N-[3-amino-2,3-dioxo-1-(phenylmethyl)propyl]-2-[3-(2,6-difluorophenyl)-1H-pyrazol-1-yl]pyridine-3-carboxamide (example 85 in WO2008/080969).

Example 72

N-[1-(2-Carbamoyl-[1,3]dioxolan-2-yl)-2-phenyl-ethyl]-2-(3-methyl-4-phenyl-pyrazol-1-yl)-nicotinamide The title compound can be prepared according to the procedure outlined in Example 1 starting from N-[3-amino-2,3-dioxo-1-(phenylmethyl)propyl]-2-(4-methyl-3-phenyl-1H-pyrazol-1-yl)pyridine-3-carboxamide (example 86 in WO2008/080969).

Example 73

N-[1-(2-Carbamoyl-[1,3]dioxolan-2-yl)-2-phenyl-ethyl]-2-[3-(4-isopropyl-phenyl)-pyrazol-1-yl]-nicotinamide The title compound can be prepared according to the procedure outlined in Example 1 starting from N-[3-amino-2,3- dioxo-1-(phenylmethyl)propyl]-2-{3-[4-(1-methylethyl) phenyl]-1H-pyrazol-1-yl}pyridine-3-carboxamide (example 87 in WO2008/080969).

Example 74

N-[1-(2-Carbamoyl-[1,3]dioxolan-2-yl)-2-pyridin-3-yl-ethyl]-2-(3-phenyl-pyrazol-1-yl)-nicotinamide The title compound can be prepared according to the procedure outlined in Example 1 starting from N-[3-amino-2,3-dioxo-1-(pyridin-3-ylmethyl)propyl]-2-(3-phenyl-1H-pyrazol-1-yl)pyridine-3-carboxamide hydrochloride (example 88 in WO2008/080969).

Example 75

N-[1-(2-Carbamoyl-[1,3]dioxolan-2-yl)-2-phenyl-ethyl]-2-[3-(2-methoxy-phenyl)-pyrazol-1-yl]-nicotinamide The title compound can be prepared according to the procedure outlined in Example 1 starting from N-[3-amino-2,3-dioxo-1-(phenylmethyl)propyl]-2-{3-[2-(methyloxy)phenyl]-1H-pyrazol-1-yl}pyridine-3-carboxamide (example 90 in WO2008/080969).

Example 76

N-[1-(2-Carbamoyl-[1,3]dioxolan-2-yl)-2-phenyl-ethyl]-2-[3-(3,5-difluoro-phenyl)-pyrazol-1-yl]nicotinamide The title compound can be prepared according to the procedure outlined in Example 1 starting from N-[3-amino-2,3-dioxo-1-(phenylmethyl)propyl]-2-[3-(3,5-difluorophenyl)-1H-pyrazol-1-yl]pyridine-3-carboxamide (example 91 in WO2008/080969).

Example 77

N-[1-(2-Carbamoyl-[1,3]dioxolan-2-yl)-2-(4-methoxy-phenyl)-ethyl]-2-[3-(2-fluoro-phenyl)-pyrazol-1-yl]-nicotinamide The title compound can be prepared according to the procedure outlined in Example 1 starting from N-(3-amino-1-{[4-(methyloxy)phenyl]methyl}-2,3-dioxopropyl)-2-[3-(2-fluorophenyl)-1H-pyrazol-1-yl]pyridine-3-carboxamide (example 92 in WO2008/080969).

Example 78

N-[1-(2-Carbamoyl-[1,3]dioxolan-2-yl)-2-phenyl-ethyl]-2-(3-o-tolyl-pyrazol-1-yl)-nicotinamide The title compound can be prepared according to the procedure outlined in Example 1 starting from N-[3-amino-2,3-dioxo-1-(phenylmethyl)propyl]-2-[3-(2-methylphenyl)-1H-pyrazol-1-yl]pyridine-3-carboxamide (example 93 in WO2008/080969).

Example 79

N-[1-(2-Carbamoyl-[1,3]dioxolan-2-yl)-2-phenyl-ethyl]-2-[3-(2,4-difluoro-phenyl)-pyrazol-1-yl]-nicotinamide The title compound can be prepared according to the procedure outlined in Example 1 starting from N-[3-amino-2,3-dioxo-1-(phenylmethyl)propyl]-2-[3-(2,4-difluorophenyl)-1H-pyrazol-1-yl]pyridine-3-carboxamide (example 94 in WO2008/080969).

Example 80

N-[1-(2-Carbamoyl-[1,3]dioxolan-2-yl)-2-phenyl-ethyl]-2-[3-(2,6-dichloro-phenyl)-pyrazol-1-yl]-nicotinamide The title compound can be prepared according to the procedure outlined in Example 1 starting from N-[3-amino-2,3-dioxo-1-(phenylmethyl)propyl]-2-[3-(2,6-dichlorophenyl)-1H-pyrazol-1-yl]pyridine-3-carboxamide (example 95 in WO2008/080969).

Example 81

2-[3-(3-Benzyloxy-phenyl)-pyrazol-1-yl]-N-[1-(2-carbamoyl-[1,3]dioxolan-2-yl)-2-phenyl-ethyl]-nicotinamide The title compound can be prepared according to the procedure outlined in Example 1 starting from N-[3-amino-2,3-dioxo-1-(phenylmethyl)propyl]-2-(3-{3-[(phenylmethyl)oxy]phenyl}-1H-pyrazol-1-yl)pyridine-3-carboxamide (example 96 in WO2008/080969).

Example 82

N-[1-(2-Carbamoyl-[1,3]dioxolan-2-yl)-2-(4-methoxy-phenyl)-ethyl]-2-[3-(2,4-difluoro-phenyl)-pyrazol-1-yl]-nicotinamide The title compound can be prepared according to the procedure outlined in Example 1 starting from N-(3-amino-1-{[4-(methyloxy)phenyl]methyl}-2,3-dioxopropyl)-2-[3-(2,4-difluorophenyl)-1H-pyrazol-1-yl]pyridine-3-carboxamide (example 97 in WO2008/080969).

Example 83

N-[1-(2-Carbamoyl-[1,3]dioxolan-2-yl)-2-(4-methoxy-phenyl)-ethyl]-2-[3-(2,4-dichloro-phenyl)-pyrazol-1-yl]nicotinamide The title compound can be prepared according to the procedure outlined in Example 1 starting from N-(3-amino-1-{[4-(methyloxy)phenyl]methyl}-2,3-dioxopropyl)-2-[3-(2,4-dichlorophenyl)-1H-pyrazol-1-yl]pyridine-3-carboxamide (example 98 in WO2008/080969).

Example 84

N-[1-(2-Carbamoyl-[1,3]dioxolan-2-yl)-2-phenyl-ethyl]-2-[3-(2-chloro-4-morpholin-4-yl-phenyl)-pyrazol-1-yl]-nicotinamide The title compound can be prepared according to the procedure outlined in Example 1 starting from N-[3-amino-2,3-dioxo-1-(phenylmethyl)propyl]-2-[3-(2-chloro-4-morpholin-4-ylphenyl)-1H-pyrazol-1-yl]pyridine-3-carboxamide (example 99 in WO2008/080969).

Example 85

N-[1-(2-Carbamoyl-[1,3]dioxolan-2-yl)-2-phenyl-ethyl]-2-(4H-chromeno[4,3-c]pyrazol-2-yl)-nicotinamide The title compound can be prepared according to the procedure outlined in Example 1 starting from N-[3-amino-2,3-dioxo-1-(phenylmethyl)propyl]-2-chromeno[4,3-c]pyrazol-2(4H)-ylpyridine-3-carboxamide (example 100 in WO2008/080969).

Example 86

N-[1-(2-Carbamoyl-[1,3]dioxolan-2-yl)-2-phenyl-ethyl]-2-[3-(4-imidazol-1-yl-phenyl)-pyrazol-1-yl]nicotinamide The title compound can be prepared according to the procedure outlined in Example 1 starting from N-[3-amino-2,3-dioxo-1-(phenylmethyl)propyl]-2-{3-[4-(1H-imidazol-1-yl)phenyl]-1H-pyrazol-1-yl}pyridine-3-carboxamide (example 101 in WO2008/080969).

Example 87

N-[1-(2-Carbamoyl-[1,3]dioxolan-2-yl)-2-phenyl-ethyl]-2-[3-(2-fluoro-4-morpholin-4-yl-phenyl)-pyrazol-1-yl]-nicotinamide The title compound can be prepared according to the procedure outlined in Example 1 starting from N-[3-amino-2,3-dioxo-1-(phenylmethyl)propyl]-2-[3-(2-fluoro-4-morpholin-4-ylphenyl)-1H-pyrazol-1-yl]pyridine-3-carboxamide (example 102 in WO2008/080969).

Example 88

N-[1-(2-Carbamoyl-[1,3]dioxolan-2-yl)-2-phenyl-ethyl]-2-[3-(5-chloro-thiophen-2-yl)-pyrazol-1-yl]nicotinamide The title compound can be prepared according to the procedure outlined in Example 1 starting from N-[3-amino-2,3-dioxo-1-(phenylmethyl)propyl]-2-[3-(5-chloro-2-thienyl)-1H-pyrazol-1-yl]pyridine-3-carboxamide (example 103 in WO2008/080969).

Example 89

N-[1-(2-Carbamoyl-[1,3]dioxolan-2-yl)-2-phenyl-ethyl]-2-(4-phenyl-pyrazol-1-yl)-nicotinamide The title compound can be prepared according to the procedure outlined in Example 1 starting from N-[3-amino-2,3-dioxo-1-(phenylmethyl)propyl]-2-[4-(2-fluorophenyl)-1H-pyrazol-1-yl]pyridine-3-carboxamide (example 104 in WO2008/080969).

Example 90

N—((S)-1-[1,3]Dioxolan-2-yl-2-phenyl-ethyl)-2-(3-phenyl-pyrazol-1-yl)-nicotinamide The title compound can be prepared according to the procedure outlined in Example 1 starting from N-[(1S)-1-Formyl-2-phenylethyl]-2-(3-phenyl-1H-pyrazol-1-yl)pyridine-3-carboxamide (example 105 in WO2008/080969).

Example 91

2-{2-Phenyl-1-[2-(3-phenyl-pyrazol-1-yl)-benzoylamino]-ethyl}-[1,3]dioxolane-2-carboxylic acid amide The title compound can be prepared according to the procedure outlined in Example 1 starting from N-[3-Amino-2,3-dioxo-1-(phenylmethyl)propyl]-2-(3-phenyl-1H-pyrazol-1-yl)benzamide (example 106 in WO2008/080969).

Example 92

N—[(S)-1-(2-Carbamoyl-[1,3]dioxolan-2-yl)-2-phenyl-ethyl]-2-(3-phenyl-pyrazol-1-yl)-nicotinamide The title compound can be prepared according to the procedure outlined in Example 1 starting from N-[(1S)-3-amino-2,3-dioxo-1-(phenylmethyl)propyl]-2-(3-phenyl-1H-pyrazol-1-yl)pyridine-3-carboxamide (example 107 in WO2008/080969).

Example 93

N—[(S)-1-(2-Carbamoyl-[1,3]dioxolan-2-yl)-2-phenyl-ethyl]-2-[3-(4-fluoro-phenyl)-pyrazol-1-yl]-nicotinamide The title compound can be prepared according to the procedure outlined in Example 1 starting from N-[(1S)-3-amino-2,3-dioxo-1-(phenylmethyl)propyl]-2-[3-(4-fluorophenyl)-1H-pyrazol-1-yl]pyridine-3-carboxamide (example 108 in WO2008/080969).

Example 94

N-[1-(2-Carbamoyl-[1,3]dioxolan-2-yl)-2-phenyl-ethyl]-2-[3-(3-chloro-thiophen-2-yl)-pyrazol-1-yl]nicotinamide The title compound can be prepared according to the procedure outlined in Example 1 starting from N-[3-amino-2,3-dioxo-1-(phenylmethyl)propyl]-2-[3-(3-chloro-2-thienyl)-1H-pyrazol-1-yl]pyridine-3-carboxamide (example 109 in WO2008/080969).

Example 95

N-[1-(2-Carbamoyl-[1,3]dioxolan-2-yl)-2-phenyl-ethyl]-2-(3-naphthalen-1-yl-pyrazol-1-yl)-nicotinamide The title compound can be prepared according to the procedure outlined in Example 1 starting from N-[3-amino-2,3-dioxo-1-(phenylmethyl)propyl]-2-(3-naphthalen-1-yl-1H-pyrazol-1-yl)pyridine-3-carboxamide (example 110 in WO2008/080969).

Example 96

N-[1-(2-Carbamoyl-[1,3]dioxolan-2-yl)-2-(4-methoxy-phenyl)-ethyl]-2-[3-(2-chloro-4-fluoro-phenyl)-pyrazol-1-yl]-nicotinamide The title compound can be prepared according to the procedure outlined in Example 1 starting from N-(3-amino-1-

{[4-(methyloxy)phenyl]methyl}-2,3-dioxopropyl)-2-[3-(2-chloro-4-fluorophenyl)-1H-pyrazol-1-yl]pyridine-3-carboxamide (example 111 in WO2008/080969).

Example 97

N-[1-(2-Carbamoyl-[1,3]dioxolan-2-yl)-2-phenyl-ethyl]-2-[3-(2,5-dichloro-phenyl)-pyrazol-1-yl]-nicotinamide The title compound can be prepared according to the procedure outlined in Example 1 starting from N-[3-amino-2,3-dioxo-1-(phenylmethyl)propyl]-2-[3-(2,5-dichlorophenyl)-1H-pyrazol-1-yl]pyridine-3-carboxamide (example 112 in WO2008/080969).

Example 98

N-[1-(2-Carbamoyl-[1,3]dioxolan-2-yl)-2-phenyl-ethyl]-2-[3-(2,3-dichloro-phenyl)-pyrazol-1-yl]-nicotinamide The title compound can be prepared according to the procedure outlined in Example 1 starting from N-[3-amino-2,3-dioxo-1-(phenylmethyl)propyl]-2-[3-(2,3-dichlorophenyl)-1H-pyrazol-1-yl]pyridine-3-carboxamide (example 115 in WO2008/080969).

Example 99

N-[1-(2-Carbamoyl-[1,3]dioxolan-2-yl)-2-phenyl-ethyl]-2-[3-(2,4,6-trifluoro-phenyl)-pyrazol-1-yl]nicotinamide The title compound can be prepared according to the procedure outlined in Example 1 starting from N-[3-amino-2,3-dioxo-1-(phenylmethyl)propyl]-2-[3-(2,4,6-trifluorophenyl)-1H-pyrazol-1-yl]pyridine-3-carboxamide (example 116 in WO2008/080969).

Example 100

N-[1-(2-Carbamoyl-[1,3]dioxolan-2-yl)-2-phenyl-ethyl]-2-[3-(2,4-dimethoxy-phenyl)-pyrazol-1-yl]-nicotinamide The title compound can be prepared according to the procedure outlined in Example 1 starting from N-[3-amino-2,3-dioxo-1-(phenylmethyl)propyl]-2-{3-[2,4-bis(methyloxy)phenyl]-1H-pyrazol-1-yl}pyridine-3-carboxamide (example 117 in WO2008/080969).

Example 101

N-[1-(2-Carbamoyl-[1,3]dioxolan-2-yl)-2-phenyl-ethyl]-2-[3-(2,2-difluoro-benzo[1,3]dioxol-5-yl)-pyrazol-1-yl]nicotinamide The title compound can be prepared according to the procedure outlined in Example 1 starting from N-[3-amino-2,3-dioxo-1-(phenylmethyl)propyl]-2-[3-(2,2-difluoro-1,3-benzodioxol-5-yl)-1H-pyrazol-1-yl]pyridine-3-carboxamide (example 118 in WO2008/080969).

Example 102

N-[1-(2-Carbamoyl-[1,3]dioxolan-2-yl)-2-phenyl-ethyl]-2-[3-(2,2-difluoro-benzo[1,3]dioxol-4-yl)-pyrazol-1-yl]-nicotinamide The title compound can be prepared according to the procedure outlined in Example 1 starting from N-[3-amino-2,3-dioxo-1-(phenylmethyl)propyl]-2-[3-(2,2-difluoro-1,3-benzodioxol-4-yl)-1H-pyrazol-1-yl]pyridine-3-carboxamide (example 119 in WO2008/080969).

Example 103

N-[1-(2-Carbamoyl-[1,3]dioxolan-2-yl)-2-phenyl-ethyl]-2-[3-(2,3-dichloro-6-fluoro-phenyl)-pyrazol-1-yl]nicotinamide The title compound can be prepared according to the procedure outlined in Example 1 starting from N-[3-amino-2,3-dioxo-1-(phenylmethyl)propyl]-2-[3-(2,3-dichloro-6-fluorophenyl)-1H-pyrazol-1-yl]pyridine-3-carboxamide (example 120 in WO2008/080969).

Example 104

N-[1-(2-Carbamoyl-[1,3]dioxolan-2-yl)-2-phenyl-ethyl]-2-[3-(2-methoxy-3,5-dimethyl-phenyl)-pyrazol-1-yl]-nicotinamide The title compound can be prepared according to the procedure outlined in Example 1 starting from N-[3-amino-2,3-dioxo-1-(phenylmethyl)propyl]-2-{3-[3,5-dimethyl-2-(methyloxy)phenyl]-1H-pyrazol-1-yl}pyridine-3-carboxamide (example 121 in WO2008/080969).

Example 105

N-[2-(4-Bromo-phenyl)-1-(2-carbamoyl-[1,3]dioxolan-2-yl)-ethyl]-2-(3-phenyl-pyrazol-1-yl)-nicotinamide The title compound can be prepared according to the procedure outlined in Example 1 starting from N-{3-amino-1-[(4-bromophenyl)methyl]-2,3-dioxopropyl}-2-(3-phenyl-1H-pyrazol-1-yl)pyridine-3-carboxamide (example 122 in WO2008/080969).

Example 106

N-[1-(2-Carbamoyl-[1,3]dioxolan-2-yl)-2-(4-fluoro-phenyl)-ethyl]-2-(3-phenyl-pyrazol-1-yl)-nicotinamide The title compound can be prepared according to the procedure outlined in Example 1 starting from N-{3-amino-1-[(4-fluorophenyl)methyl]-2,3-dioxopropyl}-2-(3-phenyl-1H-pyrazol-1-yl)pyridine-3-carboxamide (example 123 in WO2008/080969).

Example 107

N-[1-(2-Carbamoyl-[1,3]dioxolan-2-yl)-2-phenyl-ethyl]-2-[3-(2-trifluoromethoxy-phenyl)-pyrazol-1-yl]-nicotinamide The title compound can be prepared according to the procedure outlined in Example 1 starting from N-[3-amino-2,3-dioxo-1-(phenylmethyl)propyl]-2-(3-{2-[(trifluoromethyl)oxy]phenyl}-1H-pyrazol-1-yl)pyridine-3-carboxamide (example 124 in WO2008/080969).

Example 108

N-[1-(2-Carbamoyl-[1,3]dioxolan-2-yl)-2-phenyl-ethyl]-2-[3-(4-fluoro-2-methoxy-phenyl)-pyrazol-1-yl]-nicotinamide The title compound can be prepared according to the procedure outlined in Example 1 starting from N-[3-amino-2,3-dioxo-1-(phenylmethyl)propyl]-2-{3-[4-fluoro-2-(methyloxy)phenyl]-1H-pyrazol-1-yl}pyridine-3-carboxamide (example 125 in WO2008/080969).

Example 109

N-[1-(2-Carbamoyl-[1,3]dioxolan-2-yl)-2-(4-methoxy-phenyl)-ethyl]-2-[3-(3-trifluoromethyl-phenyl)-pyrazol-1-yl]-nicotinamide The title compound can be prepared according to the procedure outlined in Example 1 starting from N-(3-amino-1-{[4-(methyloxy)phenyl]methyl}-2,3-dioxopropyl)-2-{3-[3-(trifluoromethyl)phenyl]-1H-pyrazol-1-yl}pyridine-3-carboxamide (example 126 in WO2008/080969).

Example 110

N-[2-(4-Benzyloxy-phenyl)-1-(2-carbamoyl-[1,3]dioxolan-2-yl)-ethyl]-2-(3-phenyl-pyrazol-1-yl)-nicotinamide The title compound can be prepared according to the procedure outlined in Example 1 starting from N-[3-amino-2,3-dioxo-1-({4-[(phenylmethyl)oxy]phenyl}methyl)propyl]-2-(3-phenyl-1H-pyrazol-1-yl)pyridine-3-carboxamide (example 127 in WO2008/080969).

Example 111

2-(3-Benzooxazol-5-yl-pyrazol-1-yl)-N-[1-(2-carbamoyl-[1,3]dioxolan-2-yl)-2-phenyl-ethyl]-nicotinamide The title compound can be prepared according to the procedure outlined in Example 1 starting from N-[3-amino-2,3-dioxo-1-(phenylmethyl)propyl]-2-[3-(1,3-benzoxazol-5-yl)-1H-pyrazol-1-yl]pyridine-3-carboxamide (example 129 in WO2008/080969).

Example 112

N-[1-(2-Carbamoyl-[1,3]dioxolan-2-yl)-2-phenyl-ethyl]-2-[3-(5-fluoro-2-methoxy-phenyl)-pyrazol-1-yl]-nicotinamide The title compound can be prepared according to the procedure outlined in Example 1 starting from N-[3-amino-2,3-dioxo-1-(phenylmethyl)propyl]-2-{3-[5-fluoro-2-(methyloxy)phenyl]-1H-pyrazol-1-yl}pyridine-3-carboxamide (example 130 in WO2008/080969).

Example 113

N-[1-(2-Carbamoyl-[1,3]dioxolan-2-yl)-2-phenyl-ethyl]-2-[3-(5-chloro-2-methoxy-phenyl)-pyrazol-1-yl]-nicotinamide The title compound can be prepared according to the procedure outlined in Example 1 starting from N-[3-amino-2,3-dioxo-1-(phenylmethyl)propyl]-2-{3-[5-chloro-2-(methyloxy)phenyl]-1H-pyrazol-1-yl}pyridine-3-carboxamide (example 131 in WO2008/080969).

Example 114

N-[1-(2-Carbamoyl-[1,3]dioxolan-2-yl)-2-(4-trifluoromethoxy-phenyl)-ethyl]-2-(3-phenyl-pyrazol-1-yl)-nicotinamide The title compound can be prepared according to the procedure outlined in Example 1 starting from N-[3-amino-2,3-dioxo-1-({4-[(trifluoromethyl)oxy]phenyl}methyl)propyl]-2-(3-phenyl-1H-pyrazol-1-yl)pyridine-3-carboxamide (example 133 in WO2008/080969).

Example 115

N-[1-(2-Carbamoyl-[1,3]dioxolan-2-yl)-2-(4-methoxy-phenyl)-ethyl]-2-(3-naphthalen-1-yl-pyrazol-1-yl)-nicotinamide The title compound can be prepared according to the procedure outlined in Example 1 starting from N-(3-amino-1-{[4-(methyloxy)phenyl]methyl}-2,3-dioxopropyl)-2-(3-naphthalen-1-yl-1H-pyrazol-1-yl)pyridine-3-carboxamide (example 135 in WO2008/080969).

Example 116

N-[1-(2-Carbamoyl-[1,3]dioxolan-2-yl)-2-(4-methoxy-phenyl)-ethyl]-2-[3-(4-fluoro-2-methoxy-phenyl)-pyrazol-1-yl]-nicotinamide The title compound can be prepared according to the procedure outlined in Example 1 starting from N-(3-amino-1-{[4-(methyloxy)phenyl]methyl}-2,3-dioxopropyl)-2-{3-[4-fluoro-2-(methyloxy)phenyl]-1H-pyrazol-1-yl}pyridine-3-carboxamide (example 136 in WO2008/080969).

Example 117

N-[1-(2-Carbamoyl-[1,3]dioxolan-2-yl)-2-phenyl-ethyl]-2-[3-(4-chloro-2-methoxy-phenyl)-pyrazol-1-yl]-nicotinamide The title compound can be prepared according to the procedure outlined in Example 1 starting from N-[3-amino-2,3-dioxo-1-(phenylmethyl)propyl]-2-{3-[4-chloro-2-(methyloxy)phenyl]-1H-pyrazol-1-yl}pyridine-3-carboxamide (example 139 in WO2008/080969).

Example 118

N-[1-(2-Carbamoyl-[1,3]dioxolan-2-yl)-2-phenyl-ethyl]-2-(8-chloro-4H-chromeno[4,3-c]pyrazol-2-yl)-nicotinamide The title compound can be prepared according to the procedure outlined in Example 1 starting from N-[3-amino-2,3-dioxo-1-(phenylmethyl)propyl]-2-(8-chlorochromeno[4,3-c]pyrazol-2(4H)-yl)pyridine-3-carboxamide (example 140 in WO2008/080969).

Example 119

N-[1-(2-Carbamoyl-[1,3]dioxolan-2-yl)-2-phenyl-ethyl]-2-(4,5-dihydro-6-oxa-1,2-diaza-benzo[e]azulen-2-yl)-nicotinamide The title compound can be prepared according to the procedure outlined in Example 1 starting from N-[3-amino-2,3-dioxo-1-(phenylmethyl)propyl]-2-(4,5-dihydro-2H-[1]benzoxepino[5,4-c]pyrazol-2-yl)pyridine-3-carboxamide (example 141 in WO2008/080969).

Example 120

N-[1-(2-Carbamoyl-[1,3]dioxolan-2-yl)-2-phenyl-ethyl]-2-(7-methoxy-4H-chromeno[4,3-c]pyrazol-2-yl)-nicotinamide The title compound can be prepared according to the procedure outlined in Example 1 starting from N-[3-amino-2,3-dioxo-1-(phenylmethyl)propyl]-2-[7-(methyloxy)chromeno[4,3-c]pyrazol-2(4H)-yl]pyridine-3-carboxamide (example 142 in WO2008/080969).

Example 121

N-[1-(2-Carbamoyl-[1,3]dioxolan-2-yl)-2-phenyl-ethyl]-2-(8-isopropyl-4H-chromeno[4,3-c]pyrazol-2-yl)-nicotinamide The title compound can be prepared according to the procedure outlined in Example 1 starting from N-[3-amino-2,3-dioxo-1-(phenylmethyl)propyl]-2-[8-(1-methylethyl)chromeno[4,3-c]pyrazol-2(4H)-yl]pyridine-3-carboxamide (example 144 in WO2008/080969).

Example 122

N-[1-(2-Carbamoyl-[1,3]dioxolan-2-yl)-2-phenyl-ethyl]-2-[3-(2-chloro-3-fluoro-phenyl)-pyrazol-1-yl] nicotinamide The title compound can be prepared according to the procedure outlined in Example 1 starting from N-[3-amino-2,3-dioxo-1-(phenylmethyl)propyl]-2-[3-(2-chloro-3-fluorophenyl)-1H-pyrazol-1-yl]pyridine-3-carboxamide (example 145 in WO2008/080969).

Example 123

N-[1-(2-Carbamoyl-[1,3]dioxolan-2-yl)-2-(4-fluoro-phenyl)-ethyl]-2-[3-(3-trifluoromethyl-phenyl)-pyrazol-1-yl]-nicotinamide The title compound can be prepared according to the procedure outlined in Example 1 starting from N-{3-amino-1-[(4-fluorophenyl)methyl]-2,3-dioxopropyl}-2-{3-[3-(trifluoromethyl)phenyl]-1H-pyrazol-1-yl}pyridine-3-carboxamide (example 147 in WO2008/080969).

Example 124

N-[1-(2-Carbamoyl-[1,3]dioxolan-2-yl)-2-phenyl-ethyl]-2-[3-(2,5-dimethoxy-phenyl)-pyrazol-1-yl]-nicotinamide The title compound can be prepared according to the procedure outlined in Example 1 starting from N-[3-amino-2,3-dioxo-1-(phenylmethyl)propyl]-2-{3-[2,5-bis(methyloxy)phenyl]-1H-pyrazol-1-yl}pyridine-3-carboxamide (example 151 in WO2008/080969).

Example 125

N-[1-(2-Carbamoyl-[1,3]dioxolan-2-yl)-2-(4-fluoro-phenyl)-ethyl]-2-[3-(2-trifluoromethoxy-phenyl)-pyrazol-1-yl]-nicotinamide The title compound can be prepared according to the procedure outlined in Example 1 starting from N-{3-amino-1-[(4-fluorophenyl)methyl]-2,3-dioxopropyl}-2-(3-{2-[(trifluoromethyl)oxy]phenyl}-1H-pyrazol-1-yl)pyridine-3-carboxamide (example 152 in WO2008/080969).

Example 126

N-[1-(2-Carbamoyl-[1,3]dioxolan-2-yl)-2-(4-methoxy-phenyl)-ethyl]-2-[3-(2,3-dichloro-phenyl)-pyrazol-1-yl]-nicotinamide The title compound can be prepared according to the procedure outlined in Example 1 starting from N-(3-amino-1-{[4-(methyloxy)phenyl]methyl}-2,3-dioxopropyl)-2-[3-(2,3-dichlorophenyl)-1H-pyrazol-1-yl]pyridine-3-carboxamide (example 153 in WO2008/080969).

Example 127

N-[1-(2-Carbamoyl-[1,3]dioxolan-2-yl)-2-(4-fluoro-phenyl)-ethyl]-2-[3-(2-chloro-3-fluoro-phenyl)-pyrazol-1-yl]-nicotinamide The title compound can be prepared according to the procedure outlined in Example 1 starting from N-{3-amino-1-[(4-fluorophenyl)methyl]-2,3-dioxopropyl}-2-[3-(2-chloro-3-fluorophenyl)-1H-pyrazol-1-yl]pyridine-3-carboxamide (example 154 in WO2008/080969).

Example 128

N-[1-(2-Carbamoyl-[1,3]dioxolan-2-yl)-2-(4-methoxy-phenyl)-ethyl]-2-[3-(2-chloro-3-fluoro-phenyl)-pyrazol-1-yl]-nicotinamide The title compound can be prepared according to the procedure outlined in Example 1 starting from N-(3-amino-1-

{[4-(methyloxy)phenyl]methyl}-2,3-dioxopropyl)-2-[3-(2-chloro-3-fluorophenyl)-1H-pyrazol-1-yl]pyridine-3-carboxamide (example 157 in WO2008/080969).

Example 129

N-[1-(2-Carbamoyl-[1,3]dioxolan-2-yl)-2-(4-fluoro-phenyl)-ethyl]-2-[3-(2,3-dichloro-phenyl)-pyrazol-1-yl]nicotinamide The title compound can be prepared according to the procedure outlined in Example 1 starting from N-{3-amino-1-[(4-fluorophenyl)methyl]-2,3-dioxopropyl}-2-[3-(2,3-dichlorophenyl)-1H-pyrazol-1-yl]pyridine-3-carboxamide (example 158 in WO2008/080969).

Example 130

N-[1-(2-Carbamoyl-[1,3]dioxolan-2-yl)-2-phenyl-ethyl]-2-(3-quinolin-8-yl-pyrazol-1-yl)-nicotinamide The title compound can be prepared according to the procedure outlined in Example 1 starting from N-[3-amino-2,3-dioxo-1-(phenylmethyl)propyl]-2-(3-quinolin-8-yl-1H-pyrazol-1-yl)pyridine-3-carboxamide (example 160 in WO2008/080969).

Example 131

N-[1-(2-Carbamoyl-[1,3]dioxolan-2-yl)-2-(3-fluoro-phenyl)-ethyl]-2-[3-(2-trifluoromethoxy-phenyl)-pyrazol-1-yl]-nicotinamide The title compound can be prepared according to the procedure outlined in Example 1 starting from N-{3-amino-1-[(3-fluorophenyl)methyl]-2,3-dioxopropyl}-2-(3-{2-[(trifluoromethyl)oxy]phenyl}-1H-pyrazol-1-yl)pyridine-3-carboxamide (example 162 in WO2008/080969).

Example 132

N-[1-(2-Carbamoyl-[1,3]dioxolan-2-yl)-2-phenyl-ethyl]-2-[3-(2,3-dihydro-benzofuran-7-yl)-pyrazol-1-yl]-nicotinamide The title compound can be prepared according to the procedure outlined in Example 1 starting from N-[3-amino-2,3-dioxo-1-(phenylmethyl)propyl]-2-[3-(2,3-dihydro-1-benzofuran-7-yl)-1H-pyrazol-1-yl]pyridine-3-carboxamide (example 164 in WO2008/080969).

Example 133

N-[1-(2-Carbamoyl-[1,3]dioxolan-2-yl)-2-phenyl-ethyl]-2-[3-(2-difluoromethoxy-phenyl)-pyrazol-1-yl]nicotinamide The title compound can be prepared according to the procedure outlined in Example 1 starting from N-[3-amino-2,3-dioxo-1-(phenylmethyl)propyl]-2-(3-{2-[(difluoromethyl)oxy]phenyl}-1H-pyrazol-1-yl)pyridine-3-carboxamide (example 166 in WO2008/080969).

Example 134

N-[1-(2-Carbamoyl-[1,3]dioxolan-2-yl)-2-phenyl-ethyl]-2-[3-(3-trifluoromethoxy-phenyl)-pyrazol-1-yl]-nicotinamide The title compound can be prepared according to the procedure outlined in Example 1 starting from N-[3-amino-2,3-dioxo-1-(phenylmethyl)propyl]-2-(3-{3-[(trifluoromethyl)oxy]phenyl}-1H-pyrazol-1-yl)pyridine-3-carboxamide (example 168 in WO2008/080969).

Example 135

N-[2-(4-Bromo-phenyl)-1-(2-carbamoyl-[1,3]dioxolan-2-yl)-ethyl]-2-[3-(4-fluoro-phenyl)-pyrazol-1-yl]nicotinamide The title compound can be prepared according to the procedure outlined in Example 1 starting from N-{3-amino-1-[(4-bromophenyl)methyl]-2,3-dioxopropyl}-2-[3-(4-fluorophenyl)-1H-pyrazol-1-yl]pyridine-3-carboxamide (example 171 in WO2008/080969).

Example 136

N-[1-(2-Carbamoyl-[1,3]dioxolan-2-yl)-2-phenyl-ethyl]-2-(4H-thiochromeno[4,3-c]pyrazol-2-yl)-nicotinamide The title compound can be prepared according to the procedure outlined in Example 1 starting from N-[3-amino-2,3-dioxo-1-(phenylmethyl)propyl]-2-thiochromeno[4,3-c]pyrazol-2(4H)-ylpyridine-3-carboxamide (example 173 in WO2008/080969).

Example 137

N-[1-(2-Carbamoyl-[1,3]dioxolan-2-yl)-2-phenyl-ethyl]-2-(5,5-dioxo-4,5-dihydro-5lambda*6*-thio-chromeno[4,3-c]pyrazol-2-yl)-nicotinamide The title compound can be prepared according to the procedure outlined in Example 1 starting from N-[3-amino-2,3-dioxo-1-(phenylmethyl)propyl]-2-(5,5-dioxidothiochromeno[4,3-c]pyrazol-2(4H)-yl)pyridine-3-carboxamide (example 174 in WO2008/080969).

Example 138

N-[1-(2-Carbamoyl-[1,3]dioxolan-2-yl)-2-phenyl-ethyl]-2-(6-chloro-4H-chromeno[4,3-c]pyrazol-2-yl)-nicotinamide The title compound can be prepared according to the procedure outlined in Example 1 starting from N-[3-amino-2,3-dioxo-1-(phenylmethyl)propyl]-2-(6-chlorochromeno[4,3-c]pyrazol-2(4H)-yl)pyridine-3-carboxamide (example 175 in WO2008/080969).

Example 139

N-[1-(2-Carbamoyl-[1,3]dioxolan-2-yl)-2-phenyl-ethyl]-2-[4-morpholin-4-ylmethyl-3-(3-trifluorom-ethyl-phenyl)-pyrazol-1-yl]-nicotinamide The title compound can be prepared according to the procedure outlined in Example 1 starting from N-[3-amino-2,3-dioxo-1-(phenylmethyl)propyl]-2-{4-(morpholin-4-ylm-ethyl)-3-[3-(trifluoromethyl)phenyl]-1H-pyrazol-1-yl}pyridine-3-carboxamide (example 177 in WO2008/080969).

Example 140

N-[1-(2-Carbamoyl-[1,3]dioxolan-2-yl)-2-phenyl-ethyl]-2-(8-fluoro-4H-chromeno[4,3-c]pyrazol-2-yl)-nicotinamide The title compound can be prepared according to the procedure outlined in Example 1 starting from N-[3-amino-2,3-dioxo-1-(phenylmethyl)propyl]-2-(8-fluorochromeno[4,3-c]pyrazol-2(4H)-yl)pyridine-3-carboxamide (example 181 in WO2008/080969).

Example 141

N-[1-(2-Carbamoyl-[1,3]dioxolan-2-yl)-2-phenyl-ethyl]-2-(6-ethoxy-4H-chromeno[4,3-c]pyrazol-2-yl)-nicotinamide The title compound can be prepared according to the procedure outlined in Example 1 starting from N-[3-amino-2,3-dioxo-1-(phenylmethyl)propyl]-2-[6-(ethyloxy)chromeno[4,3-c]pyrazol-2(4H)-yl]pyridine-3-carboxamide (example 182 in WO2008/080969).

Example 142

N-[1-(2-Carbamoyl-[1,3]dioxolan-2-yl)-2-phenyl-ethyl]-2-(8-methoxy-4H-chromeno[4,3-c]pyrazol-2-yl)-nicotinamide The title compound can be prepared according to the procedure outlined in Example 1 starting from N-[3-amino-2,3-dioxo-1-(phenylmethyl)propyl]-2-[8-(methyloxy)chromeno[4,3-c]pyrazol-2(4H)-yl]pyridine-3-carboxamide (example 183 in WO2008/080969).

Example 143

N-[1-(2-Carbamoyl-[1,3]dioxolan-2-yl)-2-phenyl-ethyl]-2-[4-chloro-3-(4-fluoro-phenyl)-pyrazol-1-yl] nicotinamide The title compound can be prepared according to the procedure outlined in Example 1 starting from N-[3-amino-2,3-dioxo-1-(phenylmethyl)propyl]-2-[4-chloro-3-(4-fluorophenyl)-1H-pyrazol-1-yl]pyridine-3-carboxamide (example 184 in WO2008/080969).

Example 144

N-[1-(2-Carbamoyl-[1,3]dioxolan-2-yl)-2-phenyl-ethyl]-2-(8-methyl-4H-chromeno[4,3-c]pyrazol-2-yl)-nicotinamide The title compound can be prepared according to the procedure outlined in Example 1 starting from N-[3-amino-2,3-dioxo-1-(phenylmethyl)propyl]-2-(8-methylchromeno[4,3-c]pyrazol-2(4H)-yl)pyridine-3-carboxamide (example 186 in WO2008/080969).

Example 145

N-[1-(2-Carbamoyl-[1,3]dioxolan-2-yl)-2-phenyl-ethyl]-2-[3-(4-fluoro-phenyl)-4-(methanesulfony-lamino-methyl)-pyrazol-1-yl]-nicotinamide The title compound can be prepared according to the procedure outlined in Example 1 starting from N-[3-amino-2,3-dioxo-1-(phenylmethyl)propyl]-2-[3-(4-fluorophenyl)-4-{[(methylsulfonyl)amino]methyl}-1H-pyrazol-1-yl]pyridine-3-carboxamide (example 187 in WO2008/080969).

Example 146

N-[1-(2-Carbamoyl-[1,3]dioxolan-2-yl)-2-phenyl-ethyl]-5-cyano-2-[3-(2-fluoro-phenyl)-pyrazol-1-yl]-nicotinamide The title compound can be prepared according to the procedure outlined in Example 1 starting from N-[3-amino-2,3-dioxo-1-(phenylmethyl)propyl]-5-cyano-2-[3-(2-fluorophe-nyl)-1H-pyrazol-1-yl]pyridine-3-carboxamide (example 188 in WO2008/080969).

Example 147

N-[1-(2-Carbamoyl-[1,3]dioxolan-2-yl)-2-phenyl-ethyl]-2-(3-cyclohexyl-pyrazol-1-yl)-nicotinamide The title compound can be prepared according to the procedure outlined in Example 1 starting from N-[3-amino-2,3-dioxo-1-(phenylmethyl)propyl]-2-(3-cyclohexyl-1H-pyra-zol-1-yl)pyridine-3-carboxamide (example 192 in WO2008/080969).

Example 148

2-(3-Adamantan-1-yl-pyrazol-1-yl)-N-[1-(2-carbam-oyl-[1,3]dioxolan-2-yl)-2-phenyl-ethyl]-nicotina-mide The title compound can be prepared according to the procedure outlined in Example 1 starting from N-[3-amino-2,3-dioxo-1-(phenylmethyl)propyl]-2-(3-tricyclo[3.3.1.13,7]dec-1-yl-1H-pyrazol-1-yl)pyridine-3-carboxamide (example 193 in WO2008/080969).

Example 149

2-(3-tert-Butyl-pyrazol-1-yl)-N-[1-(2-carbamoyl-[1,3]dioxolan-2-yl)-2-phenyl-ethyl]-nicotinamide The title compound can be prepared according to the procedure outlined in Example 1 starting from N-[3-amino-2,3-dioxo-1-(phenylmethyl)propyl]-2-[3-(1,1-dimethylethyl)-1H-pyrazol-1-yl]pyridine-3-carboxamide (example 195 in WO2008/080969).

Example 150

N-[1-(2-Carbamoyl-[1,3]dioxolan-2-yl)-2-phenyl-ethyl]-2-(4-fluoro-3-phenyl-pyrazol-1-yl)-nicotinamide The title compound can be prepared according to the procedure outlined in Example 1 starting from N-(1-Benzyl-2-carbamoyl-2-oxo-ethyl)-2-(4-fluoro-3-phenyl-pyrazol-1-yl)-nicotinamide.

II. EVALUATION OF THE IN VIVO PHARMACOKINETIC PROFILE

The compound described in example 2 was prepared as a solution (20% EtOH, 40% PEG400, qc. Ampuwa) at a concentration appropriate for a 10 mg/kg (5 mL/kg) oral dose.

Three male Sprague-Dawley rats (200-300 g; Elevage Janvier, France) were used in this study. Due to size, each rat was housed in Macrolon Type 111 cages under conventional barrier conditions. The animals were fasted overnight prior to dosing and throughout the duration of the study but were permitted water ad libitum and were permitted food typically six hours postdosing. Control animals were placed under deep isoflurane anesthia and euthanized by bleeding (cardiac puncture) and their tissues removed and used as blank standards during sample analysis.

The group contained three rats. The group of rats received a 10 mg/kg (5 mL/kg) dose orally by gavage. At the conclusion of the study, rats were euthanized by bleeding (cardiac puncture) under deep isoflurane anesthesia.

Sample Collection

Potassium-EDTA blood samples (approx. 200-300 µl) were withdrawn from the tail vein of each animal by butterfly catheter 0.25, 0.5, 1, 1.5, 2, 3, 4, 6, 8 and 24 hours after drug administration. Upon collection, the samples were promptly placed in an ice bath, and within 2 hours after sample collection they were centrifuged at about 4° C. Upon completion of the study, animals were put under deep anesthesia using isoflurane and euthanized by bleeding (cardiac puncture). The resulting plasma samples were placed in clean PP-tubes and stored in a freezer until analysis.

The plasma samples were assayed for the compound I and corresponding drug II using appropriate liquid chromatography mass spectrometry procedures.

Pharmacokinetics and Statistical Methodology:

Peak plasma concentrations ($C_{max}$) and the time to peak plasma concentration ($T_{max}$) were read directly from the plasma concentration data for each rat. The drug and the prodrug plasma concentration data were submitted to multi-exponential curve fitting using WinNonlin. The area under the plasma concentration-time curve from 0 to t hours (time of the last measurable plasma concentration) after dosing ($AUC_{0-t}$) was calculated using the linear trapezoidal rule for the plasma concentration-time profiles. The residual area extrapolated to infinity, determined as the final measured plasma concentration ($C_t$) divided by the terminal elimination rate constant (B), was added to $AUC_{0-t}$ to produce the total area under the curve ($AUC_{0-\infty}$). The apparent total plasma clearance ($CL_p$) was calculated by dividing the administered dose by the $AUC_{0-\infty}$. The initial volume of distribution ($V_c$) was calculated as the dose divided by the extrapolated concentration at time=0 ($C_0$). The volume of distribution at steady state, $V_{ss}$, was estimated as a product of the plasma clearance ($CL_p$) and the mean residence time (MRT); the terminal-phase volume of distribution, $V_\beta$, was derived from the plasma clearance value ($CL_p$) divided by the plasma elimination rate constant ($\beta$). The bioavailability was calculated as the dose-normalized $AUC_{0-\infty}$, from the oral dose divided by the corresponding value derived from an intravenous dose.

The results are summarized in the following table 1.

TABLE 1

Oral dosing of 10 mg/kg of prodrug example 2

| | prodrug | | | | drug | | | |
|---|---|---|---|---|---|---|---|---|
| Rat # | $t_{1/2}$ (h) | $C_{max}$ (ng/ml) | $T_{max}$ (h) | AUC (ng · h/ml) | $t_{1/2}$ (h) | $C_{max}$ (ng/ml) | $T_{max}$ (h) | AUC (ng · h/ml) |
| 1 | 1.5 | 502 | 0.5 | 1315 | 1.7 | 653 | 1 | 2230 |
| 2 | 3.1 | 395 | 0.3 | 1485 | 2.5 | 532 | 1 | 2341 |
| 3 | 1.7 | 1430 | 0.3 | 2297 | 2.1 | 726 | 0.5 | 3641 |
| Mean | 1.9 | 776 | 0.3 | 1699 | 2.1 | 637 | 0.8 | 2737 |
| SEM | | 329 | 0.1 | 303 | | 57 | 0.2 | 453 | prodrug: Compound I-2
drug: Compound II-2

III. BIOLOGICAL INVESTIGATION OF INHIBITION OF CALPAIN AND CATHEPSINS

The following solutions and buffers were employed:

HBS (for 40 ml): 800 µl 1M HEPES; 2.16 ml 100 mM KCl; 4.8 ml 1M NaCl; 3.59 ml 5% glucose; 60 µl 1M $MgSO_4$; 400 µl 100 mM Na pyruvate, 28.19 ml water; pH 7.2-7.5.

lysis buffer (for 20 ml): 400 µl 1M Tris pH 8.2; 2.74 ml 1M NaCl; 520 µl 0.5M EDTA; 2 ml 10% triton X-100; 0.8 ml (=1:25) CompletePlus (1 tablet/2 ml $H_2O$); 200 µl 100 mM Pefabloc; 13.34 ml water, pH 8.2.

TBST (10×) (for 1l): 100 mM Tris (12.1 g); 1.5M NaCl (87 g); 1% Tween 20 (10 g), adjusted to pH 8.

I. Enzyme Inhibition In Vitro:

Testing for blockade of the corresponding enzymic activities was carried out by means of kinetic fluorescence assays (excitation 390 nm, emission 460 nm).

Apparent Ki values were calculated from the experimentally determined $IC_{50}$ values by the Cheng-Prussoff relation assuming a reversible competitive enzyme inhibition. The Km values of the substrates used under the assay conditions indicated above were: 90 µM (Z-Phe-Arg-AMC, cathepsin B), 10 µM (Z-Gly-Pro-Arg-AMC, cathepsin K), 2 µM (Z-Phe-Arg-AMC, cathepsin L), and 30 µM (Z-Val-Val-Arg-AMC, cathepsin S).

The indicated Ki values are averages of the inhibition constants calculated on the basis of 2 to 4 independent dose-effect plots.

The following assays were used:

1. Calpain I:

20 nM calpain-I—isolated from human erythrocytes (Calbiochem #208713), 100 µM Suc-Leu-Tyr-AMC (Bachem #I-1355) as substrate in buffer with 62 mM imidazole, 0.3 mM $CaCl_2$, 0.10% CHAPS, 0.05% BSA, 1 mM DTT at pH 7.3 and room temperature.

2. Cathepsin B:

0.25 nM cathepsin B—isolated from human liver (Calbiochem #219362), 100 µM Z-Phe-Arg-AMC (Bachem #I-1160) as substrate 50 mM MES, 2 mM EDTA, 0.05% Brij 35, 2.5 mM L-cysteine, pH 6.0, room temperature.

3. Cathepsin K:

3 nM cathepsin K—activated from recombinant human procathepsin K from *E. coli* (Calbiochem #342001), 10 μM Z-Gly-Pro-Arg-AMC (Biomol #P-142) as substrate in 50 mM MES, 2 mM EDTA, 0.05% Brij 35, 2.5 mM L-cysteine, pH 6.0, room temperature.

4. Cathepsin L:

1 nM cathepsin L—isolated from human liver (Calbiochem #219402), 2 μM Z-Phe-Arg-AMC (Bachem #I-1160) as substrate in 50 mM MES, 2 mM EDTA, 0.05% Brij 35, 2.5 mM L-cysteine, pH 6.0, room temperature.

5. Cathepsin S:

0.5 nM recombinant human cathepsin S from *E. coli* (Calbiochem #219343), 20 μM Z-Val-Val-Arg-AMC (Bachem #I-1540) as substrate in 50 mM MES, 2 mM EDTA, 0.05% Brij 35, 2.5 mM L-cysteine, pH 6.0, room temperature.

The results of the in vitro determination are indicated in Table 2. The following abbreviations are used in Table 2:

The "Calpain activity" column, ++ stands for a calpain Ki (Ki(calpain)) of ≤40 nM, + means: 40 nM<Ki(Calpain) ≤100 nM, 0 means 100 nM<Ki(Calpain)≤1 μM, – means 1 μM<Ki(Calpain)≤10 μM, –– means Ki(Calpain)>10 μM.

The "Sel. cat. B" column indicates the Ki(cathepsin B)/Ki (calpain) ratio. In this connection, ++ means a Ki(cathepsin B)/Ki(calpain) ratio of ≥30 and + means≤10≤Ki (cathepsin B)/Ki(calpain)<30.

The "Sel. cat. K" column indicates the Ki(cathepsin K)/Ki (calpain) ratio. In this connection, ++ means a Ki(cathepsin K)/Ki(calpain) ratio of ≥30 and + means 10≤Ki (cathepsin K)/Ki(calpain)<30.

The "Sel. cat. L" column indicates the Ki(cathepsin L)/Ki (calpain) ratio. In this connection, ++ means a Ki(cathepsin L)/Ki(calpain) ratio of ≥50 and + means 30≤Ki (cathepsin L)/Ki(calpain)<50.

The "Sel. cat. S" column indicates the Ki(cathepsin S)/Ki (calpain) ratio. In this connection, ++ means a Ki(cathepsin S)/Ki(calpain) ratio of ≥100 and + means 50≤Ki (cathepsin S)/Ki(calpain)<100.

TABLE 2

| Compound | Calpain activity | Sel cat. B | Sel cat. K | Sel cat. L | Sel cat. S |
|---|---|---|---|---|---|
| I-1 | –– | n.d. | n.d. | n.d. | n.d. |
| II-1 | + | ++ | ++ | ++ | ++ |
| I-2 | –– | n.d. | n.d. | n.d. | n.d. |
| II-2 | ++ | + | ++ | ++ | ++ |
| I-3 | n.d. | n.d. | n.d. | n.d. | n.d. |
| II-3 | + | + | + | ++ | ++ |

II. Spectrin Molt-4 Assay to Determine Cellular Calpain Inhibition:

The assay design and procedure were as disclosed by Chatterjee; BMC 1998, 6, PP. 509-522; the $EC_{50}$ values are calculated from the percentage degradation of spectrin as a function of the dose.

Cell culture conditions: the molt-4 cells are maintained in RPMI 1640+Glutamax™ I medium (Gibco) with 10% FCS and 50 μg/ml gentamicin at 37° C., 5% $CO_2$ and split 1:15 twice a week.

Preparation of the molt-4 cells: the cells are washed, counted and taken up in a concentration of $2 \times 10^7$ cells/ml in HBS buffer.

Dilution of the inhibitor substances: all the inhibitors are dissolved in a concentration of $10^{-2}$ M in DMSO. The stock solution is then diluted 1:15 in DMSO (=$6.67 \times 10^{-4}$ M). Thereafter the stock solution diluted 1:15 is diluted 1:4 in DMSO in two steps (=$1.67 \times 10^{-4}$ M and $4.17 \times 10^{-5}$ M). Thereafter, these three solutions are further diluted 1:50 in HBS buffer to give solutions having a concentration of $1.33 \times 10^{-5}$ M, $3.36 \times 10^{-6}$ M and $8.34 \times 10^{-7}$ M.

Test mixture: for each mixture, $10^6$ cells (see above) are introduced into a 1.5 ml Eppendorf tube. To these are added in each case 150 μl of the diluted substances (final conc. 10-5 M; $2.5 \times 10^{-6}$ M and $6.25 \times 10^{-7}$ M) and thoroughly mixed. A negative control and a positive control are used as controls. In this case, initially only 150 μl of HBS buffer is pipetted onto the cells. All the mixtures are incubated at 37° C., 5% $CO_2$ in an incubator for 10 min. Thereafter, except for the negative control, in each case $CaCl_2$ (final conc. 5 mM) and ionomycin (final conc. 5 μM) are added, thoroughly mixed and incubated at 37° C., 5% $CO_2$ in an incubator for 30 min. Then centrifuge at 700 g for 5 min. The supernatants are discarded and the pellets are taken up in 20 μl of lysis buffer. The mixtures are subsequently placed on ice for 30-60 min and then centrifuged at 15000 g for 15 min. The supernatants are removed and put into new Eppendorf tubes. The protein determination is then carried out thereon, e.g. with a MicroBCA assay (Pierce).

SDS-PAGE electrophoresis: 10 μg of total protein from each mixture are put into a new Eppendorf tube and, after pipetting in the same volume of 2× Tris-glycine SDS sample buffer (Invitrogen) and 1/10 volume of 1M DTT, thoroughly mixed and heated at 95° C. for 15 min. The solutions are briefly centrifuged and loaded onto a 6% SDS gel (Invitrogen). The gel is run at 100V with 1× Tris-glycine laemmli buffer (Biomol) until the lower band of the marker has reached the base of the gel.

Western blotting: the gel is removed from the apparatus and blotted onto nitrocellulose in 1× Tris-glycine transfer buffer (Invitrogen)+20% methanol with 1.5 A/cm² in a FastBlot chamber (Biometra) for 30 min. The nitrocellulose filter is removed, briefly washed in TBST buffer and blocked in TBST/5% milk powder for 1 h at RT (room temperature). The blocked nitrocellulose is then incubated with an anti-spectrin Ab (Chemicon) (1:10000 in TBST/5% milk powder) at RT for 3 h or at 4° C. overnight. The nitrocellulose is washed 3× in TBST buffer. It is then incubated with anti-mouse IgG (POD) antibody (Sigma) (1:10000 in TBST/5% milk powder) at room temperature for 1 h.

The nitrocellulose is then washed 5× in TBST buffer. In the next step, 5 ml of prepared solution of the SuperSignal® West Pico chemiluminescence substrate (Pierce) are put on the filter and incubated for 5 min. The nitrocellulose is then taken out of the solution, gently dabbed dry and inserted into a development folder film (Tropix). A digital image analysis system (VersaDoc, Biorad) is used to record and quantify the ECL (QuantityOne), and the percentage degradation of spectrin is calculated from the data. Graph-pad prism is used to fit the percentage spectrum degradation as a function of the dose to a sigmoidal dose-effect plot (top fixed at 100% and bottom at 0%), and the EC 50% is calculated.

The invention claimed is:
1. A carboxamide compound of the formula (I-A.a')

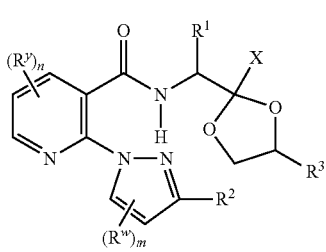

(I-A.a')

in which
R$^1$ is hydrogen, C$_1$-C$_{10}$-alkyl, C$_2$-C$_{10}$-alkenyl, C$_2$-C$_{10}$-alkynyl, where the last 3 radicals mentioned may be partly or completely halogenated and/or have 1, 2 or 3 substituents R$^{1a}$, C$_3$-C$_7$-cycloalkyl, C$_3$-C$_7$-cycloalkyl-C$_1$-C$_4$-alkyl, where two adjacent C atoms may form a double bond, where the cycloalkyl moiety may further have 1, 2, 3 or 4 radicals R$^{1b}$, aryl, aryl-C$_1$-C$_6$-alkyl, or aryl-C$_2$-C$_6$-alkenyl, where aryl in the last 3 radicals mentioned may be unsubstituted or carry 1, 2, 3 or 4 identical or different radicals R$^{1c}$; where
R$^{1a}$ is selected independently of one another from OH, SH, COOH, CN, OCH$_2$COOH, C$_1$-C$_6$-alkoxy, C$_1$-C$_6$-haloalkoxy, C$_3$-C$_7$-cycloalkyloxy, C$_1$-C$_6$-alkylthio, C$_1$-C$_6$-haloalkylthio, COOR$^{a1}$, CONR$^{a2}$R$^{a3}$, SO$_2$NR$^{a2}$R$^{a3}$, —NR$^{a2}$—SO$_2$—R$^{a4}$, NR$^{a2}$—CO—R$^{a5}$, SO$_2$—R$^{a4}$, or NR$^{a6}$R$^{a7}$,
R$^{1b}$ is selected independently of one another from OH, SH, COOH, CN, OCH$_2$COOH, halogen, phenyl which optionally has 1, 2 or 3 substituents R$^{1d}$, or C$_1$-C$_6$-alkyl, C$_1$-C$_6$-alkoxy, C$_1$-C$_6$-alkylthio, where the alkyl moieties in the last 3 substituents mentioned may be partly or completely halogenated and/or have 1, 2 or 3 substituents R$^{1a}$, COOR$^{b1}$, CONR$^{b2}$R$^{b3}$, SO$_2$NR$^{b2}$R$^{b3}$, NR$^{b2}$SO$_2$—R$^{b4}$, NR$^{b2}$-CO—R$^{b5}$, SO$_2$—R$^{b4}$, or NR$^{b6}$R$^{b7}$,
in addition two R$^{1b}$ radicals may together form a C$_1$-C$_4$-alkylene group, or 2 R$^{1b}$ radicals bonded to adjacent C atoms of cycloalkyl may form together with the carbon atoms to which they are bonded also a benzene ring,
R$^{1c}$ is selected independently of one another from OH, SH, halogen, NO$_2$, NH$_2$, CN, CF$_3$, CHF$_2$, CH$_2$F, O—CF$_3$, O—CHF$_2$, O—CH$_2$F, COOH, OCH$_2$COOH, C$_1$-C$_6$-alkyl, C$_1$-C$_6$-alkoxy, C$_1$-C$_6$-alkoxy-C$_1$-C$_4$-alkyl, C$_1$-C$_6$-alkylthio, where the alkyl moieties in the last 4 substituents mentioned may be partly or completely halogenated and/or have 1, 2 or 3 substituents R$^{1a}$, C$_3$-C$_7$-cycloalkyl, C$_3$-C$_7$-cycloalkyl-C$_1$-C$_4$-alkyl, C$_3$-C$_7$-cycloalkyloxy, where the cycloalkyl moiety of the last three radicals mentioned may have 1, 2, 3 or 4 R$^{1b}$ radicals,
aryl, O-aryl, O—CH$_2$-aryl, where the last two radicals mentioned are unsubstituted in the aryl moiety or may carry 1, 2, 3 or 4 radicals R$^{1d}$,
COOR$^{c1}$, CONR$^{c2}$R$^{c3}$, SO$_2$NR$^{c2}$R$^{c3}$, NR$^{c2}$—SO$_2$—R$^{c4}$, NR$^{c2}$-CO—R$^{c5}$, SO$_2$—R$^{c4}$,
—(CH$_2$)$_p$—NR$^{c6}$R$^{c7}$ with p=0, 1, 2, 3, 4, 5 or 6 and O—(CH$_2$)$_q$—NR$^{c6}$R$^{c7}$ with q=2, 3, 4, 5 or 6; where
R$^{a1}$, R$^{b1}$ and R$^{c1}$ are independently of one another H, C$_1$-C$_6$-alkyl, C$_1$-C$_6$-haloalkyl, C$_1$-C$_6$-alkyl which has 1, 2 or 3 substituents selected from C$_1$-C$_4$-alkoxy or C$_1$-C$_4$-haloalkoxy, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_1$-C$_6$-alkoxy-C$_1$-C$_4$-alkyl, aryl, or aryl-C$_1$-C$_4$-alkyl, where aryl in the last 2 radicals mentioned are unsubstituted or have 1, 2 or 3 substituents R$^{1d}$,
R$^{a2}$, R$^{b2}$ and R$^{c2}$ are independently of one another H, C$_1$-C$_6$-alkyl, C$_1$-C$_6$-haloalkyl, C$_1$-C$_6$-alkyl which has 1, 2 or 3 substituents selected from C$_1$-C$_4$-alkoxy or C$_1$-C$_4$-haloalkoxy, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_1$-C$_6$-alkoxy-C$_1$-C$_4$-alkyl, aryl, or aryl-C$_1$-C$_4$-alkyl, where aryl in the last 2 radicals mentioned are unsubstituted or have 1, 2 or 3 substituents R$^{1d}$, and
R$^{a3}$, R$^{b3}$ and R$^{c3}$ are independently of one another H, C$_1$-C$_6$-alkyl, C$_1$-C$_6$-haloalkyl, C$_1$-C$_6$-alkyl which has 1, 2 or 3 substituents selected from C$_1$-C$_4$-alkoxy or C$_1$-C$_4$-haloalkoxy, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_1$-C$_6$-alkoxy-C$_1$-C$_4$-alkyl, aryl, or aryl-C$_1$-C$_4$-alkyl, where aryl in the last 2 radicals mentioned are unsubstituted or have 1, 2 or 3 substituents R$^{1d}$,
R$^{a4}$, R$^{b4}$ and R$^{c4}$ are independently of one another C$_1$-C$_6$-alkyl, C$_1$-C$_6$-haloalkyl, C$_1$-C$_6$-alkyl which has 1, 2 or 3 substituents selected from C$_1$-C$_4$-alkoxy or C$_1$-C$_4$-haloalkoxy, or C$_2$-C$_6$-alkenyl, C$_2$-C$_6$-alkynyl, C$_1$-C$_6$-alkoxy-C$_1$-C$_4$-alkyl, aryl, or aryl-C$_1$-C$_4$-alkyl, where aryl in the last 2 radicals mentioned are unsubstituted or have 1, 2 or 3 substituents R$^{1d}$, and
R$^{a5}$, R$^{b5}$ and R$^{c5}$ have independently of one another one of the meanings mentioned for R$^{a1}$, R$^{b1}$ and R$^{c1}$;
R$^{a6}$, R$^{b6}$ and R$^{c6}$ are independently of one another H, C$_1$-C$_6$-alkyl, C$_1$-C$_6$-alkoxy, C$_1$-C$_6$-haloalkyl, C$_1$-C$_6$-alkyl which has 1, 2 or 3 substituents selected from C$_1$-C$_4$-alkoxy or C$_1$-C$_4$-haloalkoxy, or C$_2$-C$_6$-alkenyl, C$_2$-C$_6$-alkynyl, C$_3$-C$_4$-cycloalkyl, C$_3$-C$_4$-cycloalkyl-C$_1$-C$_4$-alkyl, C$_1$-C$_6$-alkoxy-C$_1$-C$_4$-alkyl, CO—C$_1$-C$_6$-alkyl, CO—O—C$_1$-C$_6$-alkyl, SO$_2$—C$_1$-C$_6$-alkyl, aryl, O-aryl, OCH$_2$-aryl, aryl-C$_1$-C$_4$-alkyl, CO-aryl, CO-(aryl-C$_1$-C$_4$-alkyl), CO—O-aryl, CO—O-(aryl-C$_1$-C$_4$-alkyl), SO$_2$-aryl, or SO$_2$-(aryl-C$_1$-C$_4$-alkyl), where aryl in the last 10 radicals mentioned are unsubstituted or have 1, 2 or 3 substituents R$^{1d}$, and
R$^{a7}$, R$^{b7}$ and R$^{c7}$ are independently of one another H, C$_1$-C$_6$-alkyl, C$_1$-C$_6$-haloalkyl, C$_1$-C$_6$-alkyl which has 1, 2 or 3 substituents selected from C$_1$-C$_4$-alkoxy or C$_1$-C$_4$-haloalkoxy, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_1$-C$_6$-alkoxy-C$_1$-C$_4$-alkyl, aryl, or aryl-C$_1$-C$_4$-alkyl, where aryl in the last 2 radicals mentioned are unsubstituted or have 1, 2 or 3 substituents R$^{1d}$,
or two radicals R$^{1b}$ or R$^{1c}$ bonded to adjacent C atoms form together with the C atoms to which they are bonded a 4, 5, 6 or 7-membered, optionally substituted carbocycle;
R$^{1d}$ is selected from halogen, OH, SH, NO$_2$, COOH, C(O)NH$_2$, CHO, CN, NH$_2$, OCH$_2$COOH, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, CO—C$_1$-C$_6$-alkyl, CO—O—C$_1$-C$_6$-alkyl, NH—C$_1$-C$_6$-alkyl, NHCHO, NH—C(O)C$_1$-C$_6$-alkyl, and SO$_2$—C$_1$-C$_6$-alkyl;
R$^2$ is C$_3$-C$_7$-cycloalkyl, C$_3$-C$_7$-cycloalkyl-C$_1$-C$_4$-alkyl, where two adjacent C atoms may form a double bond, where the cycloalkyl moiety may additionally have 1, 2, 3 or 4 R$^{2a}$ radicals;
aryl, O-aryl, O—CH$_2$-aryl, aryl-C$_1$-C$_6$-alkyl, or aryl-C$_2$-C$_6$-alkenyl, where aryl in the last 5 radicals mentioned may be unsubstituted or carry 1, 2, 3 or 4 identical or different R$^{2b}$ radicals; where $R^{2a}$ has one of the meanings indicated for $R^{1b}$, and
$R^{2b}$ has one of the meanings indicated for $R^{1c}$;
$R^3$ is hydrogen or $C_1$-$C_4$-alkyl;
X is a radical of the formulae $C(=O)$—O—$R^{x1}$, $C(=O)$—$NR^{x2}R^{x3}$, $C(=O)$—$N(R^{x4})$—($C_1$-$C_6$alkylene)-$NR^{x2}R^{x3}$ or $C(=O)$—$N(R^{x4})NR^{x2}R^{x3}$, in which $R^{x1}$ is hydrogen, $C_1$-$C_6$alkyl, $C_1$-$C_6$haloalkyl, $C_1$-$C_6$alkyl which has 1, 2 or 3 substituents $R^{xa}$, or $C_2$-$C_6$ alkenyl, $C_2$-$C_6$alkynyl, $C_3$-$C_7$-cycloalkyl, $C_3$-$C_7$-cycloalkyl-$C_1$-$C_4$-alkyl, $C_1$-$C_6$alkoxy-$C_1$-$C_4$-alkyl, where alkyl, alkenyl, alkoxy, alkynyl, cycloalkyl, in the last 5 radicals mentioned are unsubstituted or have 1, 2 or 3 substituents $R^{xa}$, or aryl, or aryl-$C_1$-$C_4$-alkyl, where aryl in the last 2 radicals mentioned are unsubstituted or have 1, 2 or 3 substituents $R^{x1}$, $R^{x2}$ is H, OH, CN, $C_1$-$C_6$alkyl, $C_1$-$C_6$haloalkyl, $C_1$-$C_6$alkyl which has 1, 2 or 3 substituents $R^{xa}$, or $C_2$-$C_6$ alkenyl, $C_2$-$C_6$ alkenyl, $C_3$-$C_7$-cycloalkyl, $C_3$-$C_7$-cycloalkyl-$C_1$-$C_4$-alkyl, $C_1$-$C_6$alkoxy-$C_1$-$C_4$-alkyl, CO—$C_1$-$C_6$ alkyl, CO—O—$C_1$-$C_6$alkyl, $SO_2$—$C_1$-$C_6$alkyl, O—$C_1$-$C_6$-alkyl, where alkyl, alkoxy, alkenyl, alkynyl, cycloalkyl, in the last 9 radicals mentioned are unsubstituted or have 1, 2 or 3 substituents $R^{xa}$, aryl, O-aryl, O—$CH_2$-aryl, aryl-$C_1$-$C_4$-alkyl, CO-aryl, CO-(aryl-$C_1$-$C_4$-alkyl), CO—O-aryl, CO—O-(aryl-$C_1$-$C_4$-alkyl), $SO_2$-aryl, or $SO_2$-(aryl-$C_1$-$C_4$-alkyl), where aryl in the last 10 radicals mentioned are unsubstituted or have 1, 2 or 3 substituents $R^{x1}$, and $R^{x3}$ is H, $C_1$-$C_6$alkyl, $C_1$-$C_6$haloalkyl, $C_1$-$C_6$alkyl which has 1, 2 or 3 substituents $R^{xa}$, or $C_2$-$C_6$alkenyl, $C_2$-$C_6$alkynyl, $C_3$-$C_7$-cycloalkyl, $C_3$-$C_7$-cycloalkyl-$C_1$-$C_4$-alkyl, $C_1$-$C_6$alkoxy-$C_1$-$C_4$-alkyl, where alkyl, alkenyl, alkoxy, alkynyl, cycloalkyl, in the last 5 radicals mentioned are unsubstituted or have 1, 2 or 3 substituents $R^{xa}$, aryl, or aryl-$C_1$-$C_4$-alkyl, where aryl in the last 2 radicals mentioned are unsubstituted or have 1, 2 or 3 substituents $R^{x1}$, $R^{x4}$ is H, OH, CN, $C_1$-$C_6$alkyl, $C_1$-$C_6$haloalkyl, $C_1$-$C_6$alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$alkyl, $SO_2$—$C_1$-$C_6$alkyl, where alkyl, alkenyl, alkoxy, alkynyl, cycloalkyl, in the last 8 radicals mentioned are unsubstituted or have 1, 2 or 3 substituents $R^{xa}$,
aryl, O-aryl, O—$CH_2$-aryl, aryl-$C_1$-$C_4$-alkyl, CO-aryl, CO-(aryl-$C_1$-$C_4$-alkyl), CO—O-aryl, CO—O-(aryl-$C_1$-$C_4$-alkyl), $SO_2$-aryl, or $SO_2$-(aryl-$C_1$-$C_4$-alkyl) where aryl in the last 10 radicals mentioned are unsubstituted or have 1, 2 or 3 substituents $R^{x1}$, and where $R^{xa}$ has one of the meanings indicated for $R^{1a}$, $R^{xb}$ has one of the meanings indicated for $R^{1b}$, and $R^{xd}$ has one of the meanings indicated for $R^{1d}$;
n is 0, 1 or 2,
$R^y$ is selected independently of one another from OH, SH, halogen, $NO_2$, $NH_2$, CN, $CF_3$, $CHF_2$, $CH_2F$, O—$CF_3$, O—$CHF_2$, O—$CH_2F$, COOH, $OCH_2$COOH, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{ya}$,
$C_3$-$C_7$-cycloalkyl, $C_3$-$C_7$-cycloalkyl-$C_1$-$C_4$-alkyl, $C_3$-$C_7$-cycloalkyl-O, where the cycloalkyl moiety in the last three radicals mentioned may have 1, 2, 3 or 4 $R^{yb}$ radicals,
aryl, O-aryl, $CH_2$-aryl, O—$CH_2$-aryl, where the last 3 radicals mentioned are unsubstituted in the aryl moiety or may carry 1, 2, 3 or 4 radicals $R^{yd}$,
COOR$^{y1}$, CONR$^{y2}$R$^{y3}$, $SO_2$NR$^{y2}$R$^{y3}$, —NH—$SO_2$—R$^{y4}$, NH—CO—R$^{y5}$, $SO_2$—R$^{y4}$,
—$(CH_2)_p$—NR$^{y6}$R$^{y7}$ with p=0, 1, 2, 3, 4, 5 or 6 and
O—$(CH_2)_q$—NR$^{y6}$R$^{y7}$ with q=2, 3, 4, 5 or 6;
or two $R^y$ radicals bonded to adjacent C atoms form together with the C atoms to which they are bonded a 4, 5, 6 or 7-membered, optionally substituted carbocycle, where
$R^{ya}$ has one of the meanings indicated for $R^{1a}$,
$R^{yb}$ has one of the meanings indicated for $R^{1b}$,
$R^{yd}$ has one of the meanings indicated for $R^{1d}$,
$R^{y1}$ has one of the meanings indicated for $R^{c1}$,
$R^{y2}$ has one of the meanings indicated for $R^{c2}$,
$R^{y3}$ has one of the meanings indicated for $R^{c3}$,
$R^{y4}$ has one of the meanings indicated for $R^{c4}$,
$R^{y5}$ has one of the meanings indicated for $R^{c5}$,
$R^{y6}$ has one of the meanings indicated for $R^{c6}$, and
$R^{y7}$ has one of the meanings indicated for $R^{c7}$;
m is 0 or 1, and
$R^w$ is selected from OH, F, Cl, CN, $CF_3$, $C_1$-$C_6$-alkyl which is unsubstituted or may have 1, 2 or 3 substituents $R^{wa}$, or $C_1$-$C_6$-haloalkyl, $C_1$-$C_6$-alkoxy, $C_1$-$C_6$-haloalkoxy and $C_3$-$C_7$-cycloalkyl;
or two $R^w$ radicals bonded to adjacent C atoms form together with the C atoms to which they are bonded a 4, 5, 6 or 7-membered, optionally substituted carbocycle, where
$R^{wa}$ has one of the meanings indicated for $R^{1a}$;
or a tautomer thereof, or a pharmaceutically acceptable salt thereof.

2. The carboxamide compound of claim 1, in which X is a $C(=O)$—NR$^{x2}$R$^{x3}$ radical.

3. The carboxamide compound of claim 2, in which
$R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_1$-$C_6$-alkoxy-$C_1$-$C_4$-alkyl, aryl, or aryl-$C_1$-$C_4$-alkyl, where aryl in the last 2 radicals mentioned are unsubstituted or have 1, 2 or 3 substituents $R^{xd}$, and
$R^{x3}$ is H, $C_1$-$C_6$-alkyl, $C_1$-$C_6$-haloalkyl or $C_1$-$C_6$-alkyl which has 1, 2 or 3 substituents $R^{xa}$,
in which $R^{x5}$ is hydrogen or has the meaning indicated in claim 1 for $R^{xb}$.

4. The carboxamide compound of claim 3, in which X is $C(O)$—NH$_2$.

5. The carboxamide compound of claim 1, in which $R^1$ is phenyl-$C_1$-$C_4$-alkyl, where phenyl may be unsubstituted or carry 1, 2, 3 or 4 identical or different radicals $R^{1c}$.

6. The carboxamide compound of claim 1, in which $R^2$ is selected from:
aryl, aryl-$C_1$-$C_6$-alkyl, and aryl-$C_2$-$C_6$-alkenyl, where aryl in the last 3 radicals mentioned may be unsubstituted or carry 1, 2, 3 or 4 identical or different radicals $R^{2b}$.

7. The carboxamide compound of claim 6, in which $R^2$ is selected from aryl, where aryl may be unsubstituted or carry 1, 2, 3 or 4 identical or different radicals $R^{2b}$.

8. The carboxamide compound of claim 1, in which W is selected from OH, F, Cl, NH$_2$, CN, CF$_3$, —CHF$_2$, O—CF$_3$, O—CHF$_2$, O—CH$_2$F, $C_1$-$C_6$-alkyl, $C_3$-$C_7$-cycloalkyl, $C_1$-$C_6$-alkylamino, $C_1$-$C_6$-dialkylamino, $C_1$-$C_4$ alkoxy, $C_1$-$C_4$-alkoxy-$C_1$-$C_4$-alkyl, CONR$^{y2}$R$^{y3}$, SO$_2$NR$^{y2}$R$^{y3}$, —NH—SO$_2$—R$^{y4}$, —(CH$_2$)$_p$—NR$^{y6}$R$^{y7}$, NH—CO—R$^{y5}$,
in which p is 1, 2, 3, 4, or 5, and R$^{y2}$, R$^{y3}$, R$^{y4}$, R$^{y5}$, R$^{y6}$, R$^{y7}$ are H or $C_1$-$C_6$-alkyl, phenyl, benzyl, and O-benzyl, where the phenyl ring in the last 3 groups mentioned may have 1, 2 or 3 substituents selected from halogen, OH, SH, $NO_2$, COOH, C(O)$NH_2$, CHO, CN, $NH_2$, $OCH_2COOH$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—C(O)$C_1$-$C_6$-alkyl, and $SO_2$—$C_1$-$C_6$-alkyl.

9. The carboxamide compound of claim 1, which has the S configuration at the carbon atom carrying the group $R^1$.

10. A pharmaceutical composition comprising the compound of claim 1, or a tautomer or pharmaceutically acceptable salt thereof, and a pharmaceutical carrier.

11. A compound according to claim 1, or a pharmaceutically acceptable salt thereof, selected from the group consisting of:

- N-[1-[2-(Aminocarbonyl)-1,3-dioxolan-2-yl]-2-(4-fluorophenyl)ethyl]-2-[3-(2,4-dichlorophenyl)-1H-pyrazol-1-yl]nicotinamide;
- N-{1-[2-(Aminocarbonyl)-1,3-dioxolan-2-yl]-2-phenyl-ethyl}-2-{3-[3-(trifluoromethyl)phenyl]-1H-pyrazol-1-yl}nicotinamide;
- N-{1-[2-(Aminocarbonyl)-1,3-dioxolan-2-yl]-2-phenyl-ethyl}-2-[3-(4-fluorophenyl)-1H-pyrazol-1-yl]nicotinamide;
- N-[1-(2-Carbamoyl-[1,3]dioxolan-2-yl)-pentyl]-2-(4-phenyl-pyrazol-1-yl)-nicotinamide;
- N-[1-(2-Carbamoyl-[1,3]dioxolan-2-yl)-2-phenyl-ethyl]-2-(4-phenyl-pyrazol-1-yl)-nicotinamide;
- N-[1-(2-Carbamoyl-[1,3]dioxolan-2-yl)-2-phenyl-ethyl]-2-(3-phenyl-pyrazol-1-yl)-nicotinamide;
- N-[1-(2-Carbamoyl-[1,3]dioxolan-2-yl)-pentyl]-2-(3-phenyl-pyrazol-1-yl)-nicotinamide;
- N-[1-(2-Carbamoyl-[1,3]dioxolan-2-yl)-2-phenyl-ethyl]-5-chloro-2-(3-phenyl-pyrazol-1-yl)-nicotinamide;
- N-[1-(2-Carbamoyl-[1,3]dioxolan-2-yl)-pentyl]-5-chloro-2-(3-phenyl-pyrazol-1-yl)-nicotinamide;
- N-[1-(2-Carbamoyl-[1,3]dioxolan-2-yl)-3-methyl-butyl]-2-(3-phenyl-pyrazol-1-yl)-nicotinamide;
- N-[1-(2-Carbamoyl-[1,3]dioxolan-2-yl)-3-methyl-butyl]-5-chloro-2-(3-phenyl-pyrazol-1-yl)-nicotinamide;
- N-[1-(2-Carbamoyl-[1,3]dioxolan-2-yl)-pentyl]-2-[3-(4-fluoro-phenyl)-pyrazol-1-yl]-nicotinamide;
- N-[1-(2-Carbamoyl-[1,3]dioxolan-2-yl)-2-phenyl-ethyl]-2-[3-(4-diethylamino-phenyl)-pyrazol-1-yl]-nicotinamide;
- N-[1-(2-Carbamoyl-[1,3]dioxolan-2-yl)-pentyl]-2-[3-(4-diethylaminomethyl-phenyl)-pyrazol-1-yl]-nicotinamide;
- N-[1-(2-Carbamoyl-[1,3]dioxolan-2-yl)-pentyl]-2-[3-(4-diethylamino-phenyl)-pyrazol-1-yl]-nicotinamide;
- N-[1-(2-Carbamoyl-[1,3]dioxolan-2-yl)-pentyl]-2-[3-(4-methoxy-phenyl)-pyrazol-1-yl]-nicotinamide;
- N-[1-(2-Carbamoyl-[1,3]dioxolan-2-yl)-2-(4-chloro-phenyl)-ethyl]-2-(3-phenyl-pyrazol-1-yl)-nicotinamide;
- N-[1-(2-Carbamoyl-[1,3]dioxolan-2-yl)-2-phenyl-ethyl]-5-fluoro-2-(3-phenyl-pyrazol-1-yl)-nicotinamide;
- N-[1-(2-Carbamoyl-[1,3]dioxolan-2-yl)-2-phenyl-ethyl]-2-[3-(2-chloro-phenyl)-pyrazol-1-yl]-nicotinamide;
- N-[1-(2-Carbamoyl-[1,3]dioxolan-2-yl)-2-phenyl-ethyl]-2-[3-(4-cyano-phenyl)-pyrazol-1-yl]-nicotinamide;
- N-[1-(2-Carbamoyl-[1,3]dioxolan-2-yl)-2-cyclohexyl-ethyl]-2-(3-phenyl-pyrazol-1-yl)-nicotinamide;
- N-[1-(2-Carbamoyl-[1,3]dioxolan-2-yl)-2-(4-chloro-phenyl)-ethyl]-2-[3-(4-fluoro-phenyl)-pyrazol-1-yl]-nicotinamide;
- N-[1-(2-Carbamoyl-[1,3]dioxolan-2-yl)-2-phenyl-ethyl]-2-[3-(3-chloro-phenyl)-pyrazol-1-yl]-nicotinamide;
- N-[1-(2-Carbamoyl-[1,3]dioxolan-2-yl)-2-phenyl-ethyl]-2-[3-(2-chloro-4-fluoro-phenyl)-pyrazol-1-yl]-nicotinamide;
- N-[1-(2-Carbamoyl-[1,3]dioxolan-2-yl)-2-phenyl-ethyl]-2-[3-(2-fluoro-phenyl)-pyrazol-1-yl]-nicotinamide;
- N-[1-(2-Carbamoyl-[1,3]dioxolan-2-yl)-2-phenyl-ethyl]-2-[3-(2,4-dichloro-phenyl)-pyrazol-1-yl]-nicotinamide;
- N-[1-(2-Carbamoyl-[1,3]dioxolan-2-yl)-2-(4-methoxy-phenyl)-ethyl]-2-(3-phenyl-pyrazol-1-yl)-nicotinamide;
- N-[1-(2-Carbamoyl-[1,3]dioxolan-2-yl)-2-(4-methoxy-phenyl)-ethyl]-2-[3-(4-fluoro-phenyl)-pyrazol-1-yl]-nicotinamide;
- N-[1-(2-Carbamoyl-[1,3]dioxolan-2-yl)-2-phenyl-ethyl]-5-cyano-2-(3-phenyl-pyrazol-1-yl)-nicotinamide;
- N-[1-(2-Carbamoyl-[1,3]dioxolan-2-yl)-2-phenyl-ethyl]-2-(4-methyl-3-phenyl-pyrazol-1-yl)-nicotinamide;
- N-[1-(2-Carbamoyl-[1,3]dioxolan-2-yl)-2-phenyl-ethyl]-2-[3-(2,6-difluoro-phenyl)-pyrazol-1-yl]nicotinamide;
- N-[1-(2-Carbamoyl-[1,3]dioxolan-2-yl)-2-phenyl-ethyl]-2-(3-methyl-4-phenyl-pyrazol-1-yl)-nicotinamide;
- N-[1-(2-Carbamoyl-[1,3]dioxolan-2-yl)-2-phenyl-ethyl]-2-[3-(4-isopropyl-phenyl)-pyrazol-1-yl]-nicotinamide;
- N-[1-(2-Carbamoyl-[1,3]dioxolan-2-yl)-2-phenyl-ethyl]-2-[3-(2-methoxy-phenyl)-pyrazol-1-yl]-nicotinamide;
- N-[1-(2-Carbamoyl-[1,3]dioxolan-2-yl)-2-phenyl-ethyl]-2-[3-(3,5-difluoro-phenyl)-pyrazol-1-yl]nicotinamide;
- N-[1-(2-Carbamoyl-[1,3]dioxolan-2-yl)-2-(4-methoxy-phenyl)-ethyl]-2-[3-(2-fluoro-phenyl)-pyrazol-1-yl]-nicotinamide;
- N-[1-(2-Carbamoyl-[1,3]dioxolan-2-yl)-2-phenyl-ethyl]-2-(3-o-tolyl-pyrazol-1-yl)-nicotinamide;
- N-[1-(2-Carbamoyl-[1,3]dioxolan-2-yl)-2-phenyl-ethyl]-2-[3-(2,4-difluoro-phenyl)-pyrazol-1-yl]-nicotinamide;
- N-[1-(2-Carbamoyl-[1,3]dioxolan-2-yl)-2-phenyl-ethyl]-2-[3-(2,6-dichloro-phenyl)-pyrazol-1-yl]-nicotinamide;
- 2-[3-(3-Benzyloxy-phenyl)-pyrazol-1-yl]-N-[1-(2-carbamoyl-[1,3]dioxolan-2-yl)-2-phenyl-ethyl]-nicotinamide;
- N-[1-(2-Carbamoyl-[1,3]dioxolan-2-yl)-2-(4-methoxy-phenyl)-ethyl]-2-[3-(2,4-difluoro-phenyl)-pyrazol-1-yl]-nicotinamide;
- N-[1-(2-Carbamoyl-[1,3]dioxolan-2-yl)-2-(4-methoxy-phenyl)-ethyl]-2-[3-(2,4-dichloro-phenyl)-pyrazol-1-yl]nicotinamide;
- N-[1-(2-Carbamoyl-[1,3]dioxolan-2-yl)-2-phenyl-ethyl]-2-(4-phenyl-pyrazol-1-yl)-nicotinamide;
- N—[(S)-1-(2-Carbamoyl-[1,3]dioxolan-2-yl)-2-phenyl-ethyl]-2-(3-phenyl-pyrazol-1-yl)-nicotinamide;
- N—[(S)-1-(2-Carbamoyl-[1,3]dioxolan-2-yl)-2-phenyl-ethyl]-2-[3-(4-fluoro-phenyl)-pyrazol-1-yl]-nicotinamide;
- N-[1-(2-Carbamoyl-[1,3]dioxolan-2-yl)-2-phenyl-ethyl]-2-(3-naphthalen-1-yl-pyrazol-1-yl)-nicotinamide;
- N-[1-(2-Carbamoyl-[1,3]dioxolan-2-yl)-2-(4-m ethoxy-phenyl)-ethyl]-2-[3-(2-chloro-4-fluoro-phenyl)-pyrazol-1-yl]-nicotinamide;
- N-[1-(2-Carbamoyl-[1,3]dioxolan-2-yl)-2-phenyl-ethyl]-2-[3-(2,5-dichloro-phenyl)-pyrazol-1-yl]-nicotinamide;
- N-[1-(2-Carbamoyl-[1,3]dioxolan-2-yl)-2-phenyl-ethyl]-2-[3-(2,3-dichloro-phenyl)-pyrazol-1-yl]-nicotinamide;

N-[1-(2-Carbamoyl-[1,3]dioxolan-2-yl)-2-phenyl-ethyl]-2-[3-(2,4,6-trifluoro-phenyl)-pyrazol-1-yl]nicotinamide;

N-[1-(2-Carbamoyl-[1,3]dioxolan-2-yl)-2-phenyl-ethyl]-2-[3-(2,4-dimethoxy-phenyl)-pyrazol-1-yl]-nicotinamide;

N-[1-(2-Carbamoyl-[1,3]dioxolan-2-yl)-2-phenyl-ethyl]-2-[3-(2,3-dichloro-6-fluoro-phenyl)-pyrazol-1-yl]nicotinamide;

N-[1-(2-Carbamoyl-[1,3]dioxolan-2-yl)-2-phenyl-ethyl]-2-[3-(2-methoxy-3,5-dimethyl-phenyl)-pyrazol-1-yl]-nicotinamide;

N-[2-(4-Bromo-phenyl)-1-(2-carbamoyl-[1,3]dioxolan-2-yl)-ethyl]-2-(3-phenyl-pyrazol-1-yl)-nicotinamide;

N-[1-(2-Carbamoyl-[1,3]dioxolan-2-yl)-2-(4-fluoro-phenyl)-ethyl]-2-(3-phenyl-pyrazol-1-yl)-nicotinamide;

N-[1-(2-Carbamoyl-[1,3]dioxolan-2-yl)-2-phenyl-ethyl]-2-[3-(2-trifluoromethoxy-phenyl)-pyrazol-1-yl]-nicotinamide;

N-[1-(2-Carbamoyl-[1,3]dioxolan-2-yl)-2-phenyl-ethyl]-2-[3-(4-fluoro-2-methoxy-phenyl)-pyrazol-1-yl]-nicotinamide;

N-[1-(2-Carbamoyl-[1,3]dioxolan-2-yl)-2-(4-methoxy-phenyl)-ethyl]-2-[3-(3-trifluoromethyl-phenyl)-pyrazol-1-yl]-nicotinamide;

N-[2-(4-Benzyloxy-phenyl)-1-(2-carbamoyl-[1,3]dioxolan-2-yl)-ethyl]-2-(3-phenyl-pyrazol-1-yl)-nicotinamide;

N-[1-(2-Carbamoyl-[1,3]dioxolan-2-yl)-2-phenyl-ethyl]-2-[3-(5-fluoro-2-methoxy-phenyl)-pyrazol-1-yl]-nicotinamide;

N-[1-(2-Carbamoyl-[1,3]dioxolan-2-yl)-2-phenyl-ethyl]-2-[3-(5-chloro-2-methoxy-phenyl)-pyrazol-1-yl]-nicotinamide;

N-[1-(2-Carbamoyl-[1,3]dioxolan-2-yl)-2-(4-trifluoromethoxy-phenyl)-ethyl]-2-(3-phenyl-pyrazol-1-yl)-nicotinamide;

N-[1-(2-Carbamoyl-[1,3]dioxolan-2-yl)-2-(4-methoxy-phenyl)-ethyl]-2-(3-naphthalen-1-yl-pyrazol-1-yl)-nicotinamide;

N-[1-(2-Carbamoyl-[1,3]dioxolan-2-yl)-2-(4-methoxy-phenyl)-ethyl]-2-[3-(4-fluoro-2-methoxy-phenyl)-pyrazol-1-yl]-nicotinamide;

N-[1-(2-Carbamoyl-[1,3]dioxolan-2-yl)-2-phenyl-ethyl]-2-[3-(4-chloro-2-methoxy-phenyl)-pyrazol-1-yl]-nicotinamide;

N-[1-(2-Carbamoyl-[1,3]dioxolan-2-yl)-2-phenyl-ethyl]-2-[3-(2-chloro-3-fluoro-phenyl)-pyrazol-1-yl]nicotinamide;

N-[1-(2-Carbamoyl-[1,3]dioxolan-2-yl)-2-(4-fluoro-phenyl)-ethyl]-2-[3-(3-trifluoromethyl-phenyl)-pyrazol-1-yl]-nicotinamide;

N-[1-(2-Carbamoyl-[1,3]dioxolan-2-yl)-2-phenyl-ethyl]-2-[3-(2,5-dimethoxy-phenyl)-pyrazol-1-yl]-nicotinamide;

N-[1-(2-Carbamoyl-[1,3]dioxolan-2-yl)-2-(4-fluoro-phenyl)-ethyl]-2-[3-(2-trifluoromethoxy-phenyl)-pyrazol-1-yl]-nicotinamide;

N-[1-(2-Carbamoyl-[1,3]dioxolan-2-yl)-2-(4-methoxy-phenyl)-ethyl]-2-[3-(2,3-dichloro-phenyl)-pyrazol-1-yl]-nicotinamide;

N-[1-(2-Carbamoyl-[1,3]dioxolan-2-yl)-2-(4-fluoro-phenyl)-ethyl]-2-[3-(2-chloro-3-fluoro-phenyl)-pyrazol-1-yl]-nicotinamide;

N-[1-(2-Carbamoyl-[1,3]dioxolan-2-yl)-2-(4-methoxy-phenyl)-ethyl]-2-[3-(2-chloro-3-fluoro-phenyl)-pyrazol-1-yl]-nicotinamide;

N-[1-(2-Carbamoyl-[1,3]dioxolan-2-yl)-2-(4-fluoro-phenyl)-ethyl]-2-[3-(2,3-dichloro-phenyl)-pyrazol-1-yl]nicotinamide;

N-[1-(2-Carbamoyl-[1,3]dioxolan-2-yl)-2-(3-fluoro-phenyl)-ethyl]-2-[3-(2-trifluoromethoxy-phenyl)-pyrazol-1-yl]-nicotinamide;

N-[1-(2-Carbamoyl-[1,3]dioxolan-2-yl)-2-phenyl-ethyl]-2-[3-(2-difluoromethoxy-phenyl)-pyrazol-1-yl]nicotinamide;

N-[1-(2-Carbamoyl-[1,3]dioxolan-2-yl)-2-phenyl-ethyl]-2-[3-(3-trifluoromethoxy-phenyl)-pyrazol-1-yl]-nicotinamide;

N-[2-(4-Bromo-phenyl)-1-(2-carbamoyl-[1,3]dioxolan-2-yl)-ethyl]-2-[3-(4-fluoro-phenyl)-pyrazol-1-yl]nicotinamide;

N-[1-(2-Carbamoyl-[1,3]dioxolan-2-yl)-2-phenyl-ethyl]-2-[4-chloro-3-(4-fluoro-phenyl)-pyrazol-1-yl]nicotinamide;

N-[1-(2-Carbamoyl-[1,3]dioxolan-2-yl)-2-phenyl-ethyl]-2-[3-(4-fluoro-phenyl)-4-(methanesulfonylamino-methyl)-pyrazol-1-yl]-nicotinamide;

N-[1-(2-Carbamoyl-[1,3]dioxolan-2-yl)-2-phenyl-ethyl]-5-cyano-2-[3-(2-fluoro-phenyl)-pyrazol-1-yl]-nicotinamide;

N-[1-(2-Carbamoyl-[1,3]dioxolan-2-yl)-2-phenyl-ethyl]-2-(3-cyclohexyl-pyrazol-1-yl)-nicotinamide;

2-(3-Adamantan-1-yl-pyrazol-1-yl)-N-[1-(2-carbamoyl-[1,3]dioxolan-2-yl)-2-phenyl-ethyl]-nicotinamide;

2-(3-tert-Butyl-pyrazol-1-yl)-N-[1-(2-carbamoyl-[1,3]dioxolan-2-yl)-2-phenyl-ethyl]-nicotinamide; and N-[1-(2-Carbamoyl-[1,3]dioxolan-2-yl)-2-phenyl-ethyl]-2-(4-fluoro-3-phenyl-pyrazol-1-yl)-nicotinamide.

* * * * *